United States Patent
Liu et al.

(10) Patent No.: US 7,173,051 B2
(45) Date of Patent: Feb. 6, 2007

(54) INHIBITORS OF CATHEPSIN S

(75) Inventors: Hong Liu, San Diego, CA (US); David Tully, San Diego, CA (US); Phillip Alper, Poway, CA (US); Robert Epple, San Diego, CA (US); Arnab Chatterjee, San Diego, CA (US); Michael Roberts, San Diego, CA (US)

(73) Assignee: IRM, LLC, Hamilton HM LX (BM)

( * ) Notice: Subject to any disclaimer, the term of this patent is extended or adjusted under 35 U.S.C. 154(b) by 62 days.

(21) Appl. No.: 10/868,459

(22) Filed: Jun. 10, 2004

(65) Prior Publication Data

US 2005/0049244 A1   Mar. 3, 2005

Related U.S. Application Data

(60) Provisional application No. 60/478,625, filed on Jun. 13, 2003.

(51) Int. Cl.
| | |
|---|---|
| *A61K 31/423* | (2006.01) |
| *A61K 31/403* | (2006.01) |
| *A61K 31/428* | (2006.01) |
| *C07D 263/58* | (2006.01) |
| *C07D 227/04* | (2006.01) |
| *C07D 417/02* | (2006.01) |
| *C07D 498/02* | (2006.01) |

(52) U.S. Cl. .............. 514/375; 514/410; 514/367; 548/233; 548/219; 548/235; 548/455; 548/159; 548/218

(58) Field of Classification Search ............... 548/161, 548/219, 233, 235, 455, 159; 514/367, 375, 514/410
See application file for complete search history.

(56) References Cited

U.S. PATENT DOCUMENTS

| | | | |
|---|---|---|---|
| 4,499,295 A | 2/1985 | Mueller et al. | |
| 5,374,623 A | 12/1994 | Zimmerman et al. | |
| 5,574,064 A | 11/1996 | Shibata et al. | |
| 5,691,368 A | 11/1997 | Peet et al. | |
| 5,723,469 A | 3/1998 | Shibata et al. | |
| 5,849,711 A | 12/1998 | Tung et al. | |
| 5,858,982 A | 1/1999 | Tung et al. | |
| 5,916,887 A | 6/1999 | Singh et al. | |
| 5,998,470 A | 12/1999 | Halbert et al. | |
| 6,004,933 A | 12/1999 | Spruce et al. | |
| 6,030,946 A | 2/2000 | Klaus et al. | |
| 6,057,362 A | 5/2000 | Yamashita | |
| 6,232,342 B1 | 5/2001 | Carr et al. | |
| 6,274,336 B1 | 8/2001 | Abdel-Meguid et al. | |
| 6,331,542 B1 | 12/2001 | Carr et al. | |
| 6,353,017 B1 | 3/2002 | Altmann et al. | |
| 6,369,077 B1 | 4/2002 | Marquis et al. | |
| 6,395,897 B1 | 5/2002 | Cywin et al. | |
| 6,420,364 B1 | 7/2002 | Emmanuel et al. | |
| 6,455,502 B1 | 9/2002 | Bryant et al. | |

FOREIGN PATENT DOCUMENTS

| | | |
|---|---|---|
| WO | WO 98/00171 A2 | 1/1998 |
| WO | WO 98/50534 A1 | 11/1998 |
| WO | WO 00/48993 A1 | 8/2000 |
| WO | WO 00/51998 A1 | 9/2000 |
| WO | WO 01/09110 A1 | 2/2001 |
| WO | WO 01/19816 A1 | 3/2001 |
| WO | WO 02/14314 A2 | 2/2002 |
| WO | WO 02/14317 A2 | 2/2002 |
| WO | WO 02/14315 A2 | 3/2002 |
| WO | WO 02/051983 A2 | 7/2002 |
| WO | WO 02/069901 A2 | 9/2002 |
| WO | WO02/070517 * | 9/2002 |
| WO | WO 02/070517 A2 | 9/2002 |
| WO | WO 02/070519 A1 | 9/2002 |
| WO | WO 03/013518 A1 | 2/2003 |
| WO | WO 03/020287 A2 | 3/2003 |

OTHER PUBLICATIONS

R. L. Thurmond et al., Jan. 2004, The Journal of Pharmacology and Experimental Therapeutics, vol. 308, No. 1, p. 268-276.*
Bania, J. et al.: "Human cathepsin S, but not cathepsin L, degrades efficiently MHC class II-associated invariant chain in nonprofessional APCs" PNAS; vol. 100, No. 11; pp. 6664-6669 (May 27, 2003).

* cited by examiner

*Primary Examiner*—Joseph K. McKane
*Assistant Examiner*—Yong Chu
(74) *Attorney, Agent, or Firm*—Townsend and Townsend and Crew LLP

(57) ABSTRACT

The present invention provides compounds, compositions and methods for the selective inhibition of cathepsin S. In a preferred aspect, cathepsin S is selectively inhibited in the presence of at least one other cathepsin isozyme. The present invention also provides methods for treating a disease state in a subject by selectively inhibiting cathepsin S.

24 Claims, 1 Drawing Sheet

INHIBITORS OF CATHEPSIN S

CROSS REFERENCE TO RELATED APPLICATIONS

The present application claims priority to U.S. Patent Application No. 60/478,625 filed on Jun. 13, 2003, the disclosure of which is hereby incorporated by reference in its entirety for all purposes.

BACKGROUND OF THE INVENTION

Cysteine proteases represent an enzymatic class of proteins that catalyze the hydrolysis of peptide bonds by a nucleophilic sulfhydryl group of a cysteine residue in the active site of the enzyme. Several normal and disease processes in mammals have been associated with cysteine protease activity and include, but are not limited to: osteoporosis, osteoarthritis (Inui, T., O. Ishibashi, et al. *J Biol Chem* 1997, 272(13), 8109–12; Saftig, P., E. Hunziker, et al. *Adv Exp Med Biol* 2000+ADs 2000, 477, 293–303; Saftig, P., E. Hunziker, et al. *Proc Natl Acad Sci USA* 1998, 95(23), 13453–8), periodontal diseases, Paget's disease, atherosclerosis (Jormsjo, S., D. M. Wuttge, et al. *Am J Pathol* 2002 161(3), 939–45), multiple sclerosis (Beck, H., G. Schwarz, et al. *Eur J Immunol* 2001, 31(12), 3726–36), rheumatoid arthritis (Nakagawa, T. Y., W. H. Brissette, et al. *Immunity* 1999, 10(2), 207–17; Hou, W. S., Z. Li, et al. *Am J Pathol* 2001, 159(6), 2167–77), juvenile onset diabetes, lupus, asthma (Cimerman, N., P. M. Brguljan, et al. *Pflugers Arch* 2001, 442(6 Suppl 1), R204–6), tissue rejection, Alzheimer's disease (Lemere, C. A., J. S. Munger, et al. *Am J Pathol* 1995, 146(4), 848–60), Parkinson's disease (Liu, Y., L. Fallon, et al. *Cell* 2002, 111(2), 209–18), neuronal degeneration, shock (Jaeschke, H., M. A. Fisher, et al. *J Immunol* 1998, 160(7), 3480–6), cancer (Fernandez, P. L., X. Farre, et al. *Int J Cancer* 2001, 95(1), 51–5), malaria (Malhotra, P., P. V. Dasaradhi, et al. *Mol Microbiol* 2002, 45(5), 1245–54), Chagas (Eakin, A. E., A. A. Mills, et al. *J Biol Chem* 1992, 267(11), 7411–20), leishmaniasis, shistosomiasis, and African trypanosomiasis (Caffrey, C. R., S. Scory, et al. *Curr Drug Targets* 2000, 1(2), 155–62; Lalmanach, G., A. Boulange, et al. *Biol Chem* 2002, 383(5), 739–49).

Cathepsins are a subclass of cysteine protease that belong to the enzyme classification EC 3.4.22 (Barrett, A. J., N. D. Rawlings, et al. *Handbook of proteolytic enzymes*. London, Academic Press). Cathepsins play a major role in lysosomal, endosomal, and extracellular protein degradation and have thus been implicated in many disease processes. For example, Cathepsin B [EC 3.4.22.1] has been postulated to play a role in tumor metastasis (Berquin, I. M. and B. F. Sloane *Adv Exp Med Biol* 1996, 389, 281–94).

Cathepsin S [EC 3.4.22.27] is largely expressed in professional antigen presenting cells such as macrophages and dendritic cells. Cathepsin S has been shown to be required for proper MHC class II antigen presentation (Shi, G. P., J. A. Villadangos, et al. *Immunity* 1999, 10(2) 197–206). As a result of its non-redundant role in MHC class II antigen presentation, cathepsin S has been associated with inflammation, arthritis, and atherosclerosis. The selective expression of cathepsin K [EC 3.4.22.38] in osteoclasts coupled with the ability of cathepsin K to degrade type I collagen suggests that it plays a role in normal and pathogenic bone remodeling (Bromme, D., K. Okamoto, et al. *J Biol Chem* 1996, 271(4), 2126–32). There is a need in the art for compounds and methods that selectively inhibit specific cysteine proteases for treating several pathogenic disorders in mammals. The present invention satisfies these and other needs.

SUMMARY OF THE INVENTION

The present invention provides compounds, compositions and methods for the selective inhibition of cathepsin S. The compounds of the present invention are selective for cathepsin S in the presence of other cathepsin isozymes. In a preferred embodiment, the compounds of the present invention are selective for cathepsin S in the presence of cathepsin K, L, B, or combinations thereof. The present invention also provides methods for treating a disease state in a subject by selectively inhibiting cathepsin S in the presence of other cathepsin isozymes. In a preferred aspect, cathepsin S is selectively inhibited in the presence of cathepsin K, L, B, or combinations thereof.

In one aspect, the present invention provides a compound Formula I

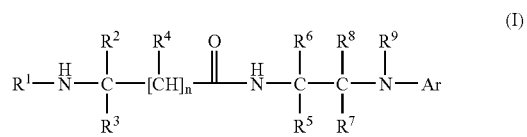

or a pharmaceutically acceptable salt or prodrug thereof, wherein:

$R^1$ is a member selected from the group of $C_6$–$C_{10}$ aryl substituted with 0–3 $R^{1a}$, a 5- to 6-membered monocyclic or 8- to 10-membered bicyclic heteroaryl containing 1 to 4 heteroatoms each independently a member selected from the group of N, O and S, wherein the heteroaryl is substituted with 0–3 $R^{1a}$, and a $C_3$–$C_8$ heterocycle containing 1 to 2 heteroatoms each independently a member selected from the group of N, O and S, wherein the heterocycle is substituted with 0–2 $R^{1a}$;

each $R^{1a}$ is independently a member selected from the group of F, Cl, Br, CN, $NO_2$, $OR^{10}$, $SCH_3$, $S(=O)CH_3$, $S(=O)_2CH_3$, $NR^{11}R^{12}$, acetyl, $C(=O)OR^{18}$, $C(=O)NR^{18}R^{19}$, $S(=O)_2N^{18}R^{19}$, $CF_3$, $OCF_3$, phenyl substituted with 0–3 $R^{14}$, a 5- to 6-membered heteroaryl containing 1 to 4 heteroatoms each independently a member selected from the group of N, O and S, wherein said heteroaryl is substituted with 0–3 $R^{14}$, and a $C_1$–$C_4$ alkyl;

$R^2$ is a member selected from the group of $C_1$–$C_6$ alkyl, a $C_6$–$C_{10}$ aryl substituted with 0–3 $R^{1a}$, a 5- to 6-membered heteroaryl containing 1 to 4 heteroatoms each independently a member selected from the group of N, O and S, wherein said heteroaryl is substituted with 0–3 $R^{1a}$, a $C_1$–$C_4$ alkyl substituted with 1 $R^{2a}$, wherein said $C_1$–$C_4$ alkyl may optionally contain a heteroatom selected from the group of —O—, —S—, —S(=O)— and —S(=O)$_2$—, a $C_3$–$C_7$ cycloalkyl substituted with 0–2 $R^{1b}$, and a $C_6$–$C_{11}$ bicycloalkyl substituted with 0–2 $R^{1b}$, provided that when $R^2$ is $C_1$–$C_6$ alkyl, at least one of $R^5$, $R^6$, $R^7$, $R^8$ and $R^9$ is not H;

each $R^{1b}$ is a member selected from the group of H, OH, F, Cl, acetyl, =O, $C_1$–$C_6$ alkyl, $C_1$–$C_6$ alkoxy, $CF_3$ and $OCF_3$;

each $R^{2a}$ is independently a member selected from the group of a $C_6$–$C_{10}$ aryl substituted with 0–3 $R^{1a}$, a perfluorophenyl, a 5- to 6-membered monocyclic or 8- to 10-membered bicyclic heteroaryl containing 1 to 4 heteroatoms each independently a member selected from the group of N, O and S, wherein said heteroaryl is substituted with 0–3 $R^{1a}$, a $C_3$–$C_8$ cycloalkyl substituted with 0–2 $R^{1b}$, and a $C_6$–$C_{11}$ bicycloalkyl substituted with 0–2 $R^{1b}$;

$R^3$ is a member selected from the group of H and $C_1$–$C_6$ alkyl;

alternatively, $R^2$ and $R^3$ are taken together to form a 5–7 membered ring containing 0–2 heteroatoms each independently a member selected from the group of N, O and S;

subscript n is 0 or 1;

$R^4$ is a member selected from the group of H and $C_1$–$C_6$ alkyl;

alternatively, $R^2$ and $R^4$ are taken together to form a $C_5$–$C_7$ cycloalkyl;

$R^5$ is a member selected from the group of H, C(=O)$OR^{24}$, C(=O)$NR^{25}R^{26}$, phenyl substituted with 0–2 $R^{21}$, 5- to 6-membered heteroaryl containing 1 to 4 heteroatoms each independently a member selected from the group of N, O and S, wherein said heteroaryl is substituted with 0–2 $R^{21}$, $C_3$–$C_7$ cycloalkyl, $C_3$–$C_6$ alkenyl and $C_1$–$C_6$ alkyl substituted with 0–2 $R^{23}$, wherein a methylene of said $C_1$–$C_6$ alkyl may optionally be replaced with a heteroatom selected from the group of —O—, —S—, —S(=O)—, —S(=O)$_2$— and —$NR^{22}$—;

each of $R^6$, $R^7$ and $R^8$ is independently a member selected from the group of H and $C_1$–$C_6$ alkyl;

alternatively, $R^5$ and $R^7$ are taken together to form a $C_5$–$C_7$ cycloalkyl;

$R^9$ is a member selected from the group of H and $C_1$–$C_6$ alkyl;

each $R^{10}$ is independently a member selected from the group of H, $C_3$–$C_7$ cycloalkyl, $C_1$–$C_4$ alkyl, a phenyl substituted with 0–3 $R^{14}$, and benzyl substituted with 0–3 $R^{14}$;

each $R^{11}$ is independently a member selected from the group of H, $^t$BOC, Cbz, $C_3$–$C_8$ cycloalkyl, ($C_1$–$C_6$ alkyl)-C(=O)—, ($C_1$–$C_6$ alkyl)-S(=O)$_2$—, a $C_1$–$C_6$ alkyl, a phenyl substituted with 0–3 $R^{14}$ and a 5- to 6-membered heteroaryl containing 1 to 4 heteroatoms each independently a member selected from the group of N, O and S, wherein said 5- to 6-membered heteroaryl is substituted with 0–3 $R^{14}$;

each $R^{12}$ is independently a member selected from the group of H and $C_1$–$C_4$ alkyl;

each $R^{13}$ is independently a member selected from the group of H, $C_3$–$C_8$ cycloalkyl, a phenyl substituted with 0–3 $R^{14}$, a 5- to 6-membered heteroaryl containing 1 to 4 heteroatoms each independently a member selected from the group of N, O and S, wherein said 5- to 6-membered heteroaryl is substituted with 0–3 $R^{14}$, and a $C_1$–$C_6$ alkyl substituted with 0–1 $R^{17}$;

each $R^{14}$ is independently a member selected from the group of H, OH, F, Cl, Br, CN, NO$_2$, COOR$^8$, C(=O)$NR^{18}R^{19}$, S(=O)$_2NR^{18}R^{19}$, acetyl, —SCH$_3$, —S(=O)CH$_3$, —S(=O)$_2$CH$_3$, $NR^{15}R^{16}$, $C_1$–$C_6$ alkoxy, $C_1$–$C_3$ perfluoroalkyl, $C_1$–$C_3$ perfluoroalkoxy and a $C_1$–$C_6$ alkyl;

each $R^{15}$ is independently a member selected from the group of H, $C_1$–$C_4$ alkyl, ($C_1$–$C_4$ alkyl)-C(=O)— and ($C_1$–$C_4$ alkyl)-S(=O)$_2$—;

each $R^{16}$ is independently a member selected from the group of H and $C_1$–$C_4$ alkyl;

each $R^{17}$ is independently a member selected from the group of H, $C_3$–$C_7$ cycloalkyl, a phenyl substituted with 0–3 $R^{14}$ and a 5- to 6-membered heteroaryl containing 1 to 4 heteroatoms each independently a member selected from the group of N, O and S, wherein said 5- to 6-membered heteroaryl is substituted with 0–3 $R^{14}$;

each of $R^{18}$ and $R^{19}$ is independently a member selected from the group of H, and $C_1$–$C_4$ alkyl;

Ar is a member selected from the group of phenyl substituted with 0–3 $R^{20}$, and 5- to 6-membered heteroaryl containing 1 to 4 heteroatoms each independently a member selected from the group of N, O and S, wherein said heteroaryl is substituted with 0–3 $R^{20}$;

each $R^{20}$ is independently a member selected from the group of H, F, Cl, Br, CN, OR$^{13}$, SCH$_3$, S(=O)CH$_3$, S(=O)$_2$CH$_3$, S(=O)$_2NR^{18}R^{19}$, $NR^{15}R^{16}$, acetyl, C(=O)$NR^{18}R^{19}$, CO$_2R^{18}$, C(=NH)NH$_2$, $C_1$–$C_6$ alkyl, CF$_3$, OCF$_3$ and a 5- to 6-membered heteroaryl containing 1 to 4 heteroatoms each independently a member selected from the group of N, O and S, wherein said heteroaryl is substituted with 0–3 $R^{14}$;

alternatively, $R^9$ and an $R^{20}$ are taken together to form a 5- to 7-membered heterocyclic ring containing 1–2 heteroatoms each independently a member selected from the group consisting of N, O and S, substituted with 0–2 $R^{28}$, wherein said 5- to 7-membered heterocyclic ring is ortho-fused to Ar;

each $R^{21}$ is a member selected from the group of H, F, Cl, Br, I, CN, NO$_2$, COOR$^{18}$, C(=O)$NR^{18}R^{19}$, S(=O)$_2NR^{18}R^{19}$, acetyl, —SCH$_3$, —S(=O)CH$_3$, —S(=O)$_2$CH$_3$, $NR^{15}R^{16}$, $C_1$–$C_4$ alkoxy, $C_1$–$C_4$ alkyl, $C_1$–$C_3$ perfluoroalkyl and $C_1$–$C_3$ perfluoroalkoxy;

$R^{22}$ is independently a member selected from the group of H, $^t$BOC, Cbz, $C_3$–$C_8$ cycloalkyl, ($C_1$–$C_6$ alkyl)-C(=O)—, ($C_1$–$C_6$ alkyl)-S(=O)$_2$—, a $C_1$–$C_6$ alkyl substituted with 0–1 $R^{17}$, a phenyl substituted with 0–3 $R^{14}$ and a 5- to 6-membered heteroaryl containing 1 to 4 heteroatoms each independently a member selected from the group of N, O and S, wherein said 5- to 6-membered heteroaryl is substituted with 0–3 $R^{14}$;

each $R^{23}$ is independently a member selected from the group of H, $OR^{24}$, F, Cl, CN, NO$_2$, C(=O)$OR^{24}$, C(=O)$NR^{25}R^{26}$, $NR^{22}$ $R^{27}$, $C_1$–$C_3$ perfluoroalkyl, $C_1$–$C_3$ perfluoroalkoxy, $C_2$–$C_4$ alkenyl, $C_2$–$C_4$ alkynyl, phenyl substituted with 0–3 $R^{21}$, 5- to 6-membered heteroaryl containing 1 to 4 heteroatoms each independently a member selected from the group of N, O and S, wherein said heteroaryl is substituted with 0–3 $R^{21}$, $C_3$–$C_8$ heterocycle containing 1 to 2 heteroatoms each independently a member selected from the group of N, O and S, wherein said heterocycle is substituted with 0–2 $R^{21}$ and is saturated or partially unsaturated, and $C_3$–$C_8$ cycloalkyl;

each $R^{24}$ is independently a member selected from the group of H, $C_3$–$C_7$ cycloalkyl, $C_1$–$C_4$ alkyl substituted with 0–1 $R^{17}$, a phenyl substituted with 0–3 $R^{14}$, and a 5- to 6-membered heteroaryl containing 1 to 4 heteroatoms each independently a member selected from the group of N, O and S, wherein said heteroaryl is substituted with 0–3 $R^{14}$;

each $R^{25}$ is independently a member selected from the group of H, $C_3$–$C_8$ cycloalkyl, a phenyl substituted with 0–3 $R^{14}$, a 5- to 6-membered heteroaryl containing 1 to 4 heteroatoms each independently a member selected from the group of N, O and S, wherein said 5- to 6-membered heteroaryl is substituted with 0–3 $R^{14}$, and a $C_1$–$C_6$ alkyl substituted with 0–1 $R^{17}$;

each $R^{26}$ is independently a member selected from the group of H and $C_1$–$C_4$ alkyl;

alternatively, $R^{25}$ and $R^{26}$ on the same N atom are taken together to form a $C_5$–$C_7$ heterocycle containing 1–2 heteroatoms each independently a member selected from the group of N, O and S;

each $R^{27}$ is independently a member selected from the group of H and $C_1$–$C_4$ alkyl;

alternatively, $R^{22}$ and $R^{27}$ on the same N atom are taken together to form a $C_5$–$C_7$ heterocycle containing 1–2 heteroatoms each independently a member selected from the group of N, O and S; and each $R^{28}$ is independently a member selected from the group of $C_1$–$C_4$ alkyl, F, Cl and $C_1$–$C_4$ alkoxy, $CF_3$ and $OCF_3$;

alternatively, two $R^{28}$ may be combined to form $C_3$–$C_6$ cycloalkyl.

In a second aspect, the present invention provides a pharmaceutical composition comprising a compound of Formula I, as described above, and a pharmaceutically acceptable excipient.

In a third aspect, the present invention provides a method of selectively inhibiting the cathepsin S activity in a mammal in need thereof, comprising administering to the mammal a therapeutically effective amount of a compound of Formula I, as described above, or a pharmaceutically acceptable salt or prodrug thereof.

DETAILED DESCRIPTION OF THE INVENTION

I. Definitions

Figure 1:
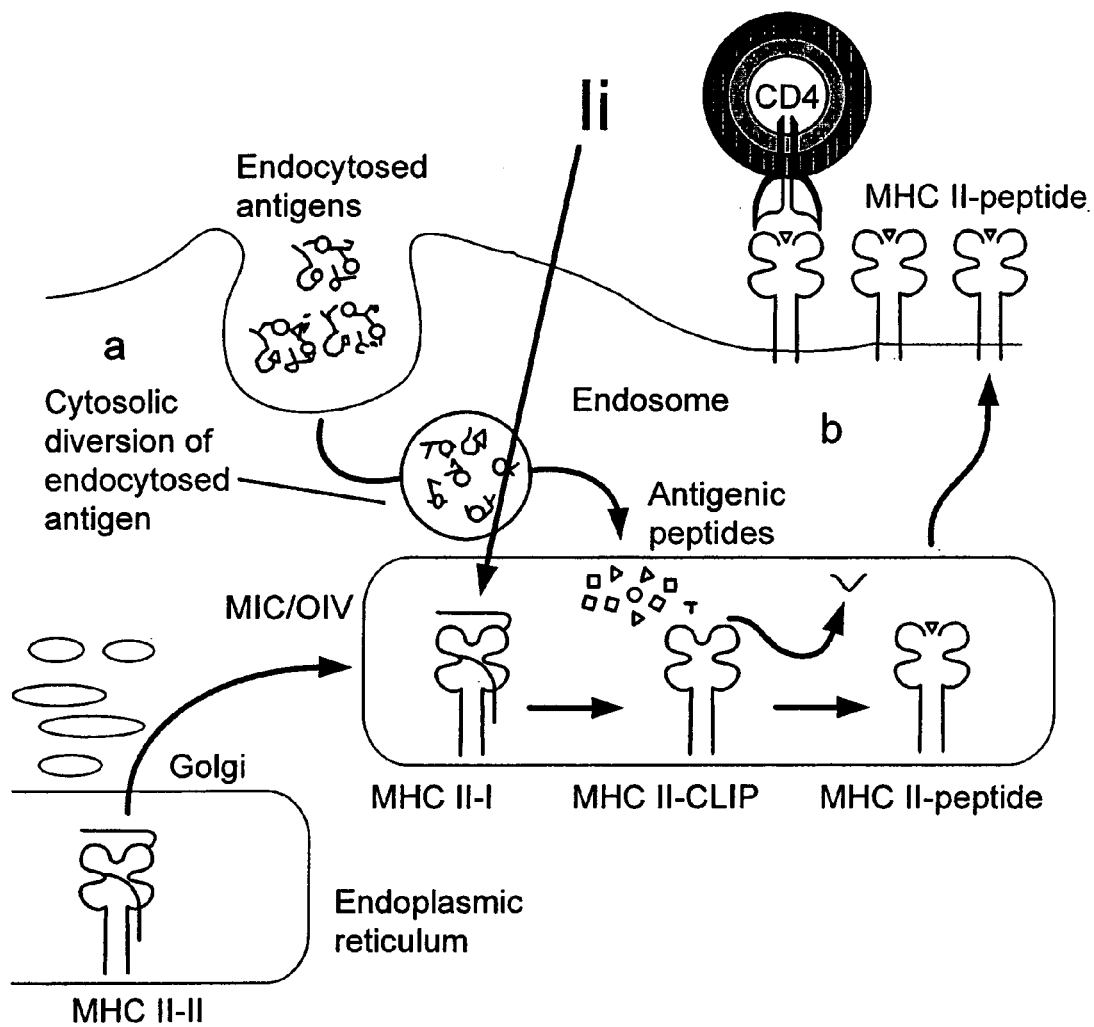
FIG. 1 depicts MHC II antigen presentation.

Unless defined otherwise, all technical and scientific terms used herein generally have the same meaning as commonly understood by one of ordinary skill in the art to which this invention belongs. Generally, the nomenclature used herein and the laboratory procedures for organic and analytical chemistry are those well known and commonly employed in the art.

As used in this disclosure, the following abbreviations and terms have the defined meaning, unless expressly modified in the context in which the term is used:

Ac acetyl
Bn benzyl
Boc t-butoxycarbonyl
Cbz or Z benzyloxycarbonyl
DCC N,N'-dicyclohexylcarbodiimide
DCM dichoromethane
DIBAL diisobutylaluminum hydride
DIC N,N'-diisopropylcarbodiimide
DIEA or DIPEA diisopropylethylamine
DMAP 4-(dimethylamino)pyridine
DMF dimethylformamide
DMSO dimethyl sulfoxide
EDC or EDCI 1-ethyl-3-(dimethylaminopropyl)-carbodiimide
Fmoc 9-fluorenylmethoxycarbonyl
HATU O-(7-azabenzoatriazol-1-yl)-N,N,N',N'-tetramethyluronium hexafluorophosphate
HOBt 1-hydroxybenzotriazole
KHMDS potassium hexamethyldisilazide
LAH lithium aluminum hydride
LDA lithium diisopropylamide
LHMDS lithium hexamethyldisilazide
m-CPBA m-chloroperbenzoic acid
MW microwave
NaHMDS sodium hexamethyldisilazide
PCC pyridinium chlorochromate
PDC pyridinium dichromate
PG protecting group
PTSA p-toluenesulfonic acid
Py pyridine
RT or rt room temperature
TEA triethylamine
Tf trifluoromethanesulfonyl
TFA trifluoroacetic acid
THF tetrahydrofuran
Tol p-tolyl
TPAP tetrapropylammonium perruthenate The term "lower" referred to above and hereinafter in connection with organic radicals or compounds respectively defines a compound or radical which can be branched or unbranched with up to and including 7, preferably up to and including 4 and (as unbranched) one or two carbon atoms.

The term "perfluoro" referred to above and hereinafter in connection with organic radicals or compounds respectively, defines a compound or radical which has at least two available hydrogens substituted with fluorine. For example, perfluorophenyl refers to 1,2,3,4,5-pentafluorophenyl, perfluoromethyl refers to 1,1,1-trifluoromethyl, and perfluoromethoxy refers to 1,1,1-trifluoromethoxy.

An alkyl group is branched or unbranched and contains 1 to 7 carbon atoms, preferably 1–4 carbon atoms. Alkyl represents, for example, methyl, ethyl, propyl, butyl, isopropyl or isobutyl.

Alkenyl represents either straight chain or branched alkenyl of 2 to 7 carbon atoms, preferably 2–4 carbon atoms, e.g. as vinyl, propenyl, isopropenyl, butenyl, isobutenyl or butadienyl.

Alkynyl represents either straight chain or branched alkynyl of 2 to 7 carbon atoms, preferably 2–4 carbon atoms, e.g. as acetylenyl, propynyl, isoprpropynyl, butynyl or isobutynyl.

Alkyl, alkenyl or alkynyl can be substituted by up to 3 substituents selected from alkoxy, aryl, heterocyclyl, hydroxy, halogen, cyano, optionally substituted amino, or optionally substituted amino-oxy or trifluoromethyl.

Alkylene represents either straight chain or branched alkylene of 1 to 7 carbon atoms, i.e. a divalent hydrocarbon radical of 1 to 7 carbon atoms; for instance, straight chain alkylene being the bivalent radical of Formula —$(CH_2)_n$—, where n is 1, 2, 3, 4, 5, 6 or 7. Preferably alkylene represents straight chain alkylene of 1 to 4 carbon atoms, e.g. a methylene, ethylene, propylene or butylene chain, or the methylene, ethylene, propylene or butylene chain monosubstituted by $C_1$–$C_3$-alkyl (preferably methyl) or disubstituted on the same or different carbon atoms by $C_1$–$C_3$-alkyl (preferably methyl), the total number of carbon atoms being up to and including 7.

An alkoxy (or alkyloxy) group preferably contains 1–7 carbon atoms, more preferably 1–6 carbon atoms, and represents for example ethoxy, propoxy, isopropoxy, isobutoxy, preferably methoxy. Alkoxy includes cycloalkyloxy and cycloalkyl-alkyloxy.

Halogen (halo) preferably represents chloro or fluoro, but may also be bromo or iodo.

Aryl represents monocyclic, bicyclic or tricyclic aryl, for example, phenyl or phenyl mono-, di- or tri-substituted by one, two or three radicals selected from alkyl, alkoxy, aryl, hydroxy, halogen, cyano, amino, amino-alkyl, trifluoromethyl, alkylenedioxy and oxy-$C_2$–$C_3$-alkylene; all of which are optionally further substituted, for instance as hereinbefore defined; or 1- or 2-naphthyl; or 1- or 2-phenanthrenyl.

Alkylenedioxy is a divalent substitute attached to two adjacent carbon atoms of phenyl, e.g. methylenedioxy or ethylenedioxy. Oxy-$C_2$–$C_3$-alkylene is also a divalent substituent attached to two adjacent carbon atoms of phenyl, e.g. oxyethylene or oxypropylene. An example for oxy-$C_2$–$C_3$-alkylene-phenyl is 2,3-dihydrobenzofuran-5-yl.

Preferred as aryl is naphthyl, phenyl or phenyl mono- or disubstituted by alkoxy, phenyl, halogen, alkyl or trifluoromethyl, especially phenyl or phenyl-mono- or disubstituted by alkoxy, halogen or trifluoromethyl, and in particular phenyl.

Examples of substituted phenyl groups as R are, e.g. 4-chlorophen-1-yl, 3,4-dichlorophen-1-yl, 4-methoxyphen-1-yl, 4-methylphen-1-yl, 4-aminomethylphen-1-yl, 4-methoxyethylaminomethylphen-1-yl, 4-hydroxyethylaminomethylphen-1-yl, 4-hydroxyethyl-(methyl)-aminomethylphen-1-yl, 3-aminomethylphen-1-yl, 4-N-acetylaminomethylphen-1-yl, 4-aminophen-1-yl, 3-aminophen-1-yl, 2-aminophen-1-yl, 4-phenyl-phen-1-yl, 4-(imidazol-1-yl)-phen-yl, 4-(imidazol-1-ylmethyl)-phen-1-yl, 4-(morpholin-1-yl)-phen-1-yl, 4-(morpholin-1-ylmethyl)-phen-1-yl, 4-(2-methoxyethylaminomethyl)-phen-1-yl and 4-(pyrrolidin-1-ylmethyl)-phen-1-yl, 4-(thiophenyl)-phen-1-yl, 4-(3-thiophenyl)-phen-1-yl, 4-(4-methylpiperazin-1-yl)-phen-1-yl, and 4-(piperidinyl)-phenyl and 4-(pyridinyl)-phenyl optionally substituted in the heterocyclic ring.

Benzyl represents a phenyl-$CH_2$— group. Substituted benzyl means a benzyl group in which the phenyl ring is substituted with one or more ring system substituents. Representative benzyl groups include 4-bromobenzyl, 4-methoxybenzyl, 2,4-dimethoxybenzyl, and the like.

Heteroaryl represents monocyclic or bicyclic heteroaryl, for example pyridyl, pyridyl N-oxide, indolyl, indazolyl, quinoxalinyl, quinolinyl, isoquinolinyl, benzothienyl, benzofuranyl, benzopyranyl, benzothiopyranyl, furanyl, pyrrolyl, thiazolyl, benzothiazolyl, oxazolyl, isoxazolyl, triazolyl, tetrazolyl, pyrazolyl, imidazolyl, thienyl, or any other radicals substituted, especially mono- or di-substituted, by e.g. alkyl, nitro or halogen. Pyridyl represents 2-, 3- or 4-pyridyl, advantageously 2- or 3-pyridyl. Thienyl represents 2- or 3-thienyl. Quinolinyl represents preferably 2-, 3- or 4-quinolinyl. Isoquinolinyl represents preferably 1-, 3- or 4-isoquinolinyl. Benzopyranyl, benzothiopyranyl represents preferably 3-benzopyranyl or 3-benzothiopyranyl, respectively. Thiazolyl represents preferably 2- or 4-thiazolyl, and most preferred, 4-thiazolyl. Triazolyl is preferably 1-, 2- or 5-(1,2,4-triazolyl). Tetrazolyl is preferably 5-tetrazolyl).

Preferably, heteroaryl is pyridyl, pyridyl N-oxide, indolyl, quinolinyl, pyrrolyl, thiazolyl, isoxazolyl, triazolyl, tetrazolyl, pyrazolyl, imidazolyl, thienyl, furanyl, benzothiazolyl, benzofuranyl, isoquinolinyl, benzothienyl, oxazolyl, indazolyl, or any of the radicals substituted, especially mono- or di-substituted.

Biaryl may preferably be, e.g., biphenyl, namely 2, 3 or 4-biphenyl, preferably, 4-biphenyl, each optionally substituted by, e.g., alkyl, alkoxy, halogen, trifluoromethyl or cyano, or heterocyclic-carbocyclic biaryl, preferably, e.g., thienylphenyl, pyrrolylphenyl and pyrazolylphenyl.

Cycloalkyl represents a saturated cyclic hydrocarbon optionally substituted by alkyl which contains 3 to 10 ring carbons and is advantageously cyclopentyl, cyclohexyl, cycloheptyl or cyclooctyl optionally substituted by alkyl.

Bicycloalkyl represents a saturated bicyclic ring group of 7–15 carbon atoms. Exemplary bicycloalkyl rings include [3.3.0]bicyclooctanyl, [2.2.2]bicyclooctanyl, [4.3.0]bicyclononane, [4.4.0]bicyclodecane (decalin), spiro[3.4]octanyl, spiro[2.5]octanyl, and so forth, optionally substituted by alkyl.

Amino can be optionally substituted by, e.g., alkyl.

Carbocyclic represents a saturated or partially unsaturated cyclic hydrocarbon with 5 to 7 ring members, wherein 1 to 2 ring members can optionally be replaced with one of the following groups: —O—, —S—, —S(=O)—, —S(=O)$_2$— and —NR—, wherein R is a radical of the present invention.

Heterocyclyl represents a saturated cyclic hydrocarbon containing one or more, preferably 1 or 2 heteroatoms selected from O, N or S, and from 3 to 10, preferably 5 to 8, ring atoms; for example, tetrahydrofuranyl, tetrahydrothienyl, tetrahydropyrrolyl, piperidinyl, piperazinyl or morpholino; all of which can be optionally substituted, for instance as hereinbefore defined for aryl.

Polycyclic ring systems in which any two adjacent rings have two (e.g., only two), adjacent atoms in common are said to be "ortho-fused". Such ring systems have n common sides and 2n common atoms.

Pharmaceutically acceptable salts of the acidic compounds of the present invention are salts formed with bases, namely cationic salts such as alkali and alkaline earth metal salts, such as sodium, lithium, potassium, calcium, magnesium, as well as ammonium salts, such as ammonium, trimethyl-ammonium, diethylammonium, and tris-(hydroxymethyl)-methyl-ammonium salts.

Similarly acid addition salts, such as of mineral acids, organic carboxylic and organic sulfonic acids, e.g., hydrochloric acid, methanesulfonic acid, maleic acid, are also possible provided a basic group, such as pyridyl, constitutes part of the structure.

"Treat", "treating" and "treatment" refer to a method of alleviating or abating a disease and/or its attendant symptoms.

"Inhibition", "inhibits" and "inhibitor" refer to a compound that prohibits, or a method of prohibiting, a specific action or function.

"Inhibition constant", $K_i$, is the dissociation constant of the enzyme-inhibitor complex, or the reciprocal of the binding affinity of the inhibitor to the enzyme. For classical inhibition the value of $K_i$ is much greater than the enzyme concentration and the $K_i$ can be measured by monitoring the rate of reaction for a competitive substrate at multiple inhibitor concentrations. The inhibited rates are then fit by nonlinear regression to the following equation:

$$v_i/v_o = \frac{K_m + [S]}{K_m(1 + [I]/K_i) + [S]}$$

where $v_o$ is the initial rate of substrate processing in the absence of inhibitor, $v_i$ is the initial rate of substrate processing at a concentration [I] of inhibitor, $K_m$ is the steady state Michaelis constant (Fersht, A. *Structure and Mechanism in Protein Science*. New York, W.H. Freeman and Company, 1999), and [S] is the concentration of competitive substrate.

The assumption being made for the classical inhibition described above is that the free inhibitor concentration is equal to the total inhibitor concentration. For inhibitors that have $K_i$'s that are approximately equal to the enzyme concentration [E], the assumption that the free inhibitor concentration is equal to the total inhibitor concentration is no longer valid and an alternative equation has to be fit for determination of the apparent inhibition constant, $K_i^{app}$ using described methods (Kuzmic, P., K. C. Elrod, et al., *Anal Biochem* 2000, 286(1), 45–50):

$$v_i/v_o = \frac{[E] - [I] - K_i^{app} + SQRT(([E] - [I] - K_i^{app})^2 + 4[E]K_i^{app})}{2[E]}.$$

The inhibition constant, $K_i$, can be determined from the apparent inhibition constant, $K_i^{app}$, for competitive inhibitors by using the following relationship:

$$K_i = \frac{K_i^{app}}{1 + [S]/K_m}.$$

"Therapeutically effective amount" refers to that amount of the compound being administered sufficient to prevent development of or alleviate to some extent one or more of the symptoms of the condition or disorder being treated.

"Composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the Formulation and deleterious to the recipient thereof.

"Subject" refers to animals such as mammals, including, but not limited to, primates (e.g., humans), cows, sheep, goats, horses, dogs, cats, rabbits, rats, mice and the like. In certain aspects, the subject is a human.

"Prodrug" refers to the compounds of this invention which may be modified by appending appropriate functionalities to enhance selective biological properties. Such modifications are known in the art and include those which increase penetration into a given biological compartment (e.g. central nervous system), increase oral bioavailability, increase solubility to allow administration by injection, alter metabolism and alter rate and/or route of excretion. In addition, the compounds may be altered to prodrug form such that the desired compound is created in the body of the patient as the result of the action of metabolic or other biochemical processes on the prodrug.

It will be apparent to one skilled in the art that certain compounds of this invention may exist in tautomeric forms or hydrated forms, all such forms of the compounds being within the scope of the invention.

Structures depicted herein are also meant to include compounds that differ only in the presence of isotopically enriched atoms. For example, compounds having the present structures except for the replacement of a hydrogen by a deuterium are expressly included in the present invention.

II. General

Cathepsin S is a cysteine protease that has been associated with several normal and disease processes in mammals. Specifically, cathepsin S has been directly associated with inflammation, arthritis, and atherosclerosis, as a result of its role in MHC class II antigen presentation. In a preferred aspect, the present invention provides compounds that inhibit the activity of cathepsin S. The present invention also provides methods for treating several disease states in mammals by inhibiting the activity of cathepsin S. In a more preferred aspect, the compounds of the present invention selectively inhibit cathepsin S in the presence of at least one cathepsin isozyme (e.g. cathepsin K).

III. Compounds

A. Preparation of Compounds

In the following schemes 1–4, several methods of preparing the compounds of the present invention are demonstrated. One of skill in the art will appreciate that these methods are representative, and in no way inclusive of all methods of preparing the compounds of the present invention. The radicals in schemes 1–4 are as described in Formula I.

The arylaminoethylamines 1-A (Scheme 1) used in the present invention can be prepared by a decarboxylative ring opening of oxazolidin-2-one with an aromatic amine as described in E. Altman et al. *J Med Chem*. 2002, 45, 2352–54 and references cited therein.

Scheme 1

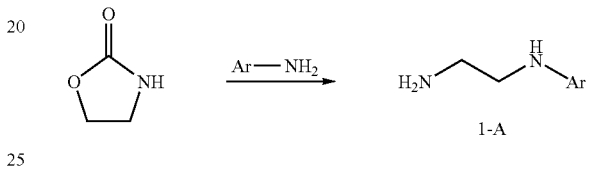

1-A

Synthetic approaches to indolines used in this invention are widely described in the literature and well known to one skilled in the art. The typical methods are illustrated in, but are not limited to, the following references. See: (a) G. W. Gribble et al. *Synthesis* 1977, 859; (b) A. Smith et al. *Chem. Commun.* 1965, 427; (c) G. W. Gribble et al. *J. Am. Chem. Soc.* 1974, 96, 7812; (d) J. G. Berger *Synthesis* 1974, 508; (e) L. J. Dolby et al. *J. Heterocycl. Chem.* 1966, 3, 124; (f) W. A. Remers at al *J. Org. Chem.* 1971, 36, 279; (g) S. O'Brien et al. *J. Chem. Soc.* 1960, 4609; (h) Y. Kikugawa et al. *Synthesis* 1978, 477.

Synthetic approaches to non-commercially available α and β-amino acids used in this invention are widely described in the literature and are well known to one skilled in the art. The typical methods are illustrated in, but are not limited to, the following references. See: (a) D. J. Ager et al. *Current opinion in drug discovery & development* 2001, 4, 800–807; (b) R. O. Duthaler *Tetrahedron* 1994, 50, 1539–1650; (c) M. J. O'Donnell *Aldrichimica Acta* 2001, 34, 3–15; (d) K. B. Sharpless et al. *J. Am. Chem. Soc.* 1998, 120, 1207–17; (e) E. Juaristi et al. *Aldrichimica Acta* 1994, 27, 3–11; (f) D.C. Cole *Tetrahedron* 1994, 50, 9517–9582 and references cited therein.

A synthetic route to compounds of the present invention of general Formula (I), in which $R^5$ and/or $R^6$ are not H, is described in Scheme 2.

Scheme 2

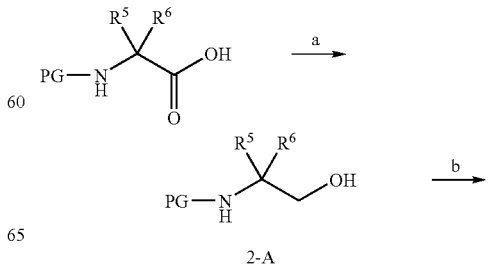

2-A

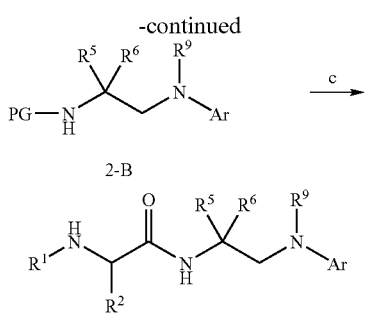

2-B

2-C a) [BH₃·THF, THF 0° C.] or [i) TEA, i-butyl-chloroformate, THF, 0° C.; ii) NaBH₄, H₂O, 0° C. to RT];

b) i) Dess-Martin periodinane, DCM; ii) NHR⁹Ar, NaCNBH₃, AcOH, MeOH;

c) i) removal of PG; ii) amide coupling condition.

A N-protected amino acid can be reduced using either the BH₃ method or NaBH₄ reduction of the corresponding mixed anhydride [see R. C. Larock *A guide to functional group preparations* pp.548–552, Wiley-VCH, 1989] to obtain 2-A (Scheme 2). One can then oxidize the alcohol to the aldehyde and reductively aminate the resulting aldehyde with an amine to afford 2-B. This intermediate can then be deprotected using the appropriate reagents for the PG, such as TFA for Boc, and the resulting amine can be acylated to give access to 2-C.

Compounds of the present invention can also be made via the route shown in Scheme 3.

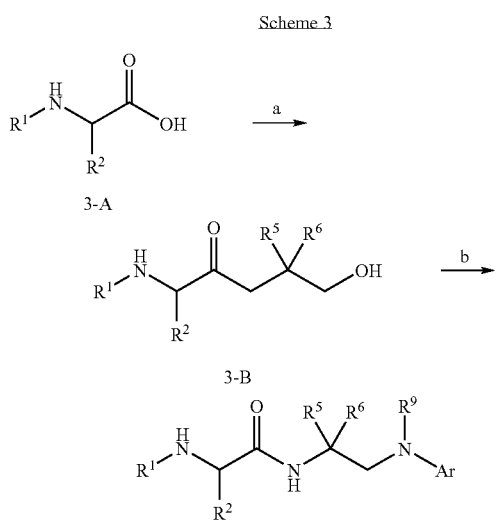

Scheme 3

3-A

3-B

3-C a) [EDC, HOBt, DCM or DMF, then ethanolamine (5 eq.) in DMF or DCM] or [PyBOP (1.0 eq.), TEA (1.0 eq.) NH₂C(R⁵R⁶)CH₂OH in DCM followed by TEA in DCM];

b) i) Dess-Martin periodinane, DCM; ii) NHR⁹Ar, NaCNBH₃, AcOH, MeOH.

Synthetic approaches to N-aryl-α-amino acids and N-aryl-β-amino acids used in this invention are widely described in the literature and well known to one skilled in the art. The typical methods are illustrated in, but are not limited to, the following references. See: (a) Ma, D. et al. *Tetrahedron: asymmetry* 1996, 7, 3075; (b) Ma, D. et al. *J. Am. Chem. Soc.* 1998, 120, 12459; (c) Ma, D. et al. *Org. Lett.* 2001, 3, 2583; (d) Endo, Y. et al. *Chem. Pharm. Bull.* 1984, 32, 358; (e) Kogan, T. P. et al. *Tetrahedron* 1990, 46, 6623; (f) Semmelhack, M. F. et al. *Tetrahedron Lett.* 1993, 34, 1395; (g) Quick, J. et al. *Tetrahedron Lett.* 1994, 35, 8549; (h) Endo, Y. et al. *J. Am. Chem. Soc.* 1996, 118, 1841; (i) Miller, W. H. et al. *Tetrahedron Lett.* 1995, 36, 9433; 0) Leeson, P. D. et al. *Med. Chem. Res.* 1991, 1, 64; (k) Hosokami, T. et al. *Chem. Pharm. Bull.* 1992, 40, 2712; (l) Rudolph, J. *Tetrahedron Lett.* 2000, 56, 3161; (m) Rudolph, J. *J. Med. Chem.* 2001, 44, 619; (n) Lazer, E. S. et. al. *J. Med. Chem.* 1994, 37, 913–923 and references cited therein. A preferred method of preparing the compounds of the present invention is shown in Scheme 4.

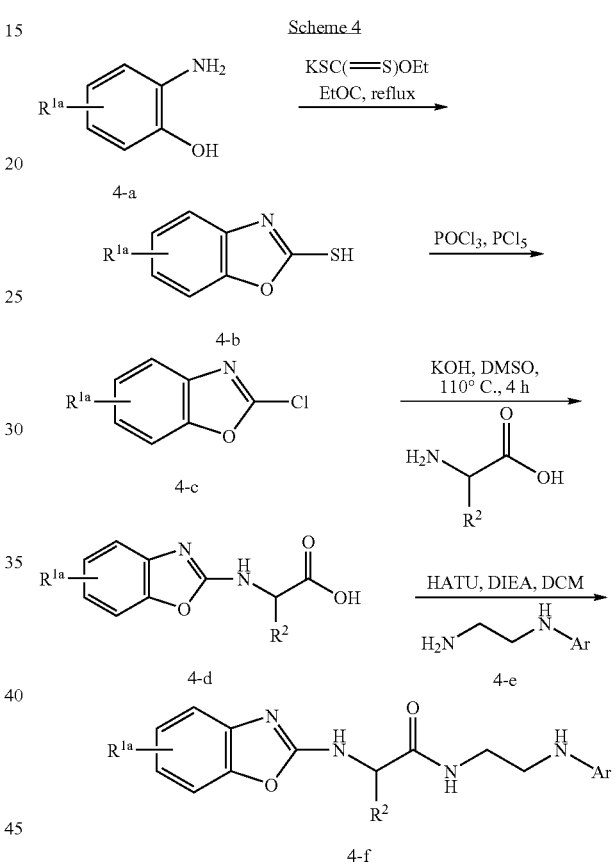

Scheme 4

4-a 4-b 4-c 4-d    4-e 4-f

B. Preferred Compounds

In one aspect, the present invention provides a compound of Formula I:

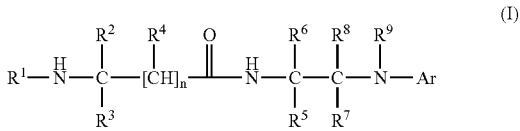

(I)

or a pharmaceutically acceptable salt or prodrug thereof, wherein:

$R^1$ is independently a member selected from the group of $C_6$–$C_{10}$ aryl substituted with 0–3 $R^{1a}$, a 5- to 6-membered monocyclic or 8- to 10-membered bicyclic heteroaryl containing 1 to 4 heteroatoms each independently a member selected from the group of N, O and S, wherein said heteroaryl is substituted with 0–3 $R^{1a}$, and a $C_3$–$C_8$ heterocycle containing 1 to 2 heteroatoms each independently a member selected from the group of N, O and S, wherein said heterocycle is substituted with 0–2 $R^{1a}$;

each $R^{1a}$ is independently a member selected from the group of F, Cl, Br, CN, $NO_2$, $OR^{10}$, $SCH_3$, $S(=O)CH_3$, $S(=O)_2CH_3$, $NR^{11}R^{12}$, acetyl, $C(=O)OR^8$, $C(=O)NR^{18}R^{19}$, $S(=O)_2NR^{18}R^{19}$, $CF_3$, $OCF_3$, phenyl substituted with 0–3 $R^{14}$, a 5- to 6-membered heteroaryl containing 1 to 4 heteroatoms each independently a member selected from the group of N, O and S, wherein said heteroaryl is substituted with 0–3 $R^{14}$, and a $C_1$–$C_4$ alkyl;

$R^2$ is a member selected from the group of $C_1$–$C_6$ alkyl, a $C_6$–$C_{10}$ aryl substituted with 0–3 $R^{1a}$, a 5- to 6-membered heteroaryl containing 1 to 4 heteroatoms each independently a member selected from the group of N, O and S, wherein said heteroaryl is substituted with 0–3 $R^{1a}$, a $C_1$–$C_4$ alkyl substituted with 1 $R^{2a}$, wherein said $C_1$–$C_4$ alkyl may optionally contain a heteroatom selected from the group of —O—, —S—, —S(=O)— and —S(=O)$_2$—, a $C_3$–$C_7$ cycloalkyl substituted with 0–2 $R^{1b}$, and a $C_6$–$C_{11}$ bicycloalkyl substituted with 0–2 $R^{1b}$, provided that when $R^2$ is $C_1$–$C_6$ alkyl, at least one of $R^5$, $R^6$, $R^7$, $R^8$ and $R^9$ is not H;

each $R^{1b}$ is independently a member selected from the group of H, OH, F, Cl, acetyl, =O, $C_1$–$C_6$ alkyl, $C_1$–$C_6$ alkoxy, $CF_3$ and $OCF_3$;

each $R^{2a}$ is independently a member selected from the group of a $C_6$–$C_{10}$ aryl substituted with 0–3 $R^{1a}$, a perfluorophenyl, a 5- to 6-membered monocyclic or 8- to 10-membered bicyclic heteroaryl containing 1 to 4 heteroatoms each independently a member selected from the group of N, O and S, wherein said heteroaryl is substituted with 0–3 $R^{1a}$, a $C_3$–$C_8$ cycloalkyl substituted with 0–2 $R^{1b}$, and a $C_6$–$C_{11}$ bicycloalkyl substituted with 0–2 $R^{1b}$;

$R^3$ is a member selected from the group of H and $C_1$–$C_6$ alkyl;

alternatively, $R^2$ and $R^3$ are taken together to form a 5–7 membered ring containing 0–2 heteroatoms each independently a member selected from the group of N, O and S;

subscript n is 0 or 1;

$R^4$ is a member selected from the group of H and $C_1$–$C_6$ alkyl;

alternatively, $R^2$ and $R^4$ are taken together to form a $C_5$–$C_7$ cycloalkyl;

$R^5$ is a member selected from the group of H, $C(=O)OR^{24}$, $C(=O)NR^{25}R^{26}$, phenyl substituted with 0–2 $R^{21}$, 5- to 6-membered heteroaryl containing 1 to 4 heteroatoms each independently a member selected from the group of N, O and S, wherein said heteroaryl is substituted with 0–2 $R^{21}$, $C_3$–$C_7$ cycloalkyl, $C_3$–$C_6$ alkenyl and $C_1$–$C_6$ alkyl substituted with 0–2 $R^{23}$, wherein said $C_1$–$C_6$ alkyl may optionally contain a heteroatom selected from the group of —O—, —S—, —S(=O)—, —S(=O)$_2$— and —$NR^{22}$—;

each of $R^6$, $R^7$ and $R^8$ is independently a member selected from the group of H and $C_1$–$C_6$ alkyl;

alternatively, $R^5$ and $R^7$ are taken together to form a $C_5$–$C_7$ cycloalkyl;

$R^9$ is a member selected from the group of H and $C_1$–$C_6$ alkyl;

each $R^{10}$ is independently a member selected from the group of H, $C_3$–$C_7$ cycloalkyl, $C_1$–$C_4$ alkyl, a phenyl substituted with 0–3 $R^{14}$, and benzyl substituted with 0–3 $R^{14}$;

each $R^{11}$ is independently a member selected from the group of H, $^t$BOC, Cbz, $C_3$–$C_8$ cycloalkyl, ($C_1$–$C_6$ alkyl)-C(=O)—, ($C_1$–$C_6$ alkyl)-S(=O)$_2$—, a $C_1$–$C_6$ alkyl, a phenyl substituted with 0–3 $R^{14}$ and a 5- to 6-membered heteroaryl containing 1 to 4 heteroatoms each independently a member selected from the group of N, O and S, wherein said 5- to 6-membered heteroaryl is substituted with 0–3 $R^{14}$;

each $R^{12}$ is independently a member selected from the group of H and $C_1$–$C_4$ alkyl;

each $R^{13}$ is independently a member selected from the group of H, $C_3$–$C_8$ cycloalkyl, a phenyl substituted with 0–3 $R^{14}$, a 5- to 6-membered heteroaryl containing 1 to 4 heteroatoms each independently a member selected from the group of N, O and S, wherein said 5- to 6-membered heteroaryl is substituted with 0–3 $R^{14}$, and a $C_1$–$C_6$ alkyl substituted with 0–1 $R^{17}$;

each $R^{14}$ is independently a member selected from the group of H, OH, F, Cl, Br, CN, $NO_2$, $COOR^{18}$, $C(=O)NR^{18}R^{19}$, $S(=O)_2NR^{18}R^{19}$, acetyl, —$SCH_3$, —$S(=O)CH_3$, —$S(=O)_2CH_3$, $NR^{15}R^{16}$, $C_1$–$C_6$ alkoxy, $C_1$–$C_3$ perfluoroalkyl, $C_1$–$C_3$ perfluoroalkoxy and a $C_1$–$C_6$ alkyl;

each $R^{15}$ is independently a member selected from the group of H, $C_1$–$C_4$ alkyl, ($C_1$–$C_4$ alkyl)-C(=O)— and ($C_1$–$C_4$ alkyl)-S(=O)$_2$—;

each $R^{16}$ is independently a member selected from the group of H and $C_1$–$C_4$ alkyl;

each $R^{17}$ is independently a member selected from the group of H, $C_3$–$C_7$ cycloalkyl, a phenyl substituted with 0–3 $R^{14}$ and a 5- to 6-membered heteroaryl containing 1 to 4 heteroatoms each independently a member selected from the group of N, O and S, wherein said 5- to 6-membered heteroaryl is substituted with 0–3 $R^{14}$;

each of $R^{18}$ and $R^{19}$ is independently a member selected from the group of H, and $C_1$–$C_4$ alkyl;

Ar is a member selected from the group of phenyl substituted with 0–3 $R^{20}$, and 5- to 6-membered heteroaryl 1 to 4 heteroatoms each independently a member selected from the group of N, O and S, wherein said heteroaryl is substituted with 0–3 $R^{20}$;

each $R^{20}$ is independently a member selected from the group of H, F, Cl, Br, CN, $OR^{13}$, $SCH_3$, $S(=O)CH_3$, $S(=O)_2CH_3$, $S(=O)_2NR^{18}R^{19}$, $NR^{15}R^{16}$, acetyl, $C(=O)NR^{18}R^{19}$, $CO_2R^{18}$, $C(=NH)NH_2$, $C_1$–$C_6$ alkyl, $CF_3$, $OCF_3$ and a 5- to 6-membered heteroaryl containing 1 to 4 heteroatoms each independently a member selected from the group of N, O and S, wherein said heteroaryl is substituted with 0–3 $R^{14}$;

alternatively, $R^9$ and an $R^{20}$ are taken together to form a 5- to 7-membered heterocyclic ring containing 1–2 heteroatoms each independently a member selected from the group consisting of N, O and S, substituted with 0–2 $R^{28}$, wherein said 5- to 7-membered heterocyclic ring is ortho-fused to Ar;

each $R^{21}$ is a member selected from the group of H, F, Cl, Br, I, CN, $NO_2$, $COOR^{18}$, $C(=O)NR^{18}R^{19}$, $S(=O)_2NR^{18}R^{19}$, acetyl, —$SCH_3$, —$S(=O)CH_3$, —$S(=O)_2CH_3$, $NR^{15}R^{16}$, $C_1$–$C_4$ alkoxy, $C_1$–$C_4$ alkyl, $C_1$–$C_3$ perfluoroalkyl and $C_1$–$C_3$ perfluoroalkoxy;

$R^{22}$ is independently a member selected from the group of H, $^t$BOC, Cbz, $C_3$–$C_8$ cycloalkyl, ($C_1$–$C_6$ alkyl)-C(=O)—, ($C_1$–$C_6$ alkyl)-S(=O)$_2$—, a $C_1$–$C_6$ alkyl substituted with 0–1 $R^{17}$, a phenyl substituted with 0–3 $R^{14}$ and a 5- to 6-membered heteroaryl containing 1 to 4 heteroatoms each independently a member selected from the group of N, O and S, wherein said 5- to 6-membered heteroaryl is substituted with 0–3 $R^{14}$;

each $R^{23}$ is independently a member selected from the group of H, $OR^{24}$, F, Cl, CN, $NO_2$, $C(=O)OR^{24}$, $C(=O)NR^{25}R^{26}$, $NR^{22}R^{27}$, $C_1$–$C_3$ perfluoroalkyl, $C_1$–$C_3$ perfluoroalkoxy, $C_2$–$C_4$ alkenyl, $C_2$–$C_4$ alkynyl, phenyl substituted with 0–3 $R^{21}$, 5- to 6-membered heteroaryl containing 1 to 4 heteroatoms each independently a member selected from the group of N, O and S, wherein said heteroaryl is substituted with 0–3 $R^{21}$, $C_3$–$C_8$ heterocycle containing 1 to 2 heteroatoms each independently a member selected from the group of N, O and S, wherein said heterocycle is substituted with 0–2 $R^{21}$ and is saturated or partially unsaturated, and $C_3$–$C_8$ cycloalkyl;

each $R^{24}$ is independently a member selected from the group of H, $C_3$–$C_7$ cycloalkyl, $C_1$–$C_4$ alkyl substituted with 0–1 $R^{17}$, a phenyl substituted with 0–3 $R^{14}$, and a 5- to 6-membered heteroaryl containing 1 to 4 heteroatoms each independently a member selected from the group of N, O and S, wherein said heteroaryl is substituted with 0–3 $R^{14}$;

each $R^{25}$ is independently a member selected from the group of H, $C_3$–$C_8$ cycloalkyl, a phenyl substituted with 0–3 $R^{14}$, a 5- to 6-membered heteroaryl containing 1 to 4 heteroatoms each independently a member selected from the group of N, O and S, wherein said 5- to 6-membered heteroaryl is substituted with 0–3 $R^{14}$, and a $C_1$–$C_6$ alkyl substituted with 0–1 $R^{17}$;

each $R^{26}$ is independently a member selected from the group of H and $C_1$–$C_4$ alkyl;

alternatively, $R^{25}$ and $R^{26}$ on the same N atom are taken together to form a $C_5$–$C_7$ heterocycle containing 1–2 heteroatoms each independently a member selected from the group of N, O and S;

each $R^{27}$ is independently a member selected from the group of H and $C_1$–$C_4$ alkyl;

alternatively, $R^{22}$ and $R^{27}$ on the same N atom are taken together to form a $C_5$–$C_7$ heterocycle containing 1–2 heteroatoms each independently a member selected from the group of N, O and S; and each $R^{28}$ is independently a member selected from the group of $C_1$–$C_4$ alkyl, F, Cl and $C_1$–$C_4$ alkoxy, $CF_3$ and $OCF_3$;

alternatively, two $R^{28}$ may be combined to form $C_3$–$C_6$ cycloalkyl.

In a preferred aspect, the present invention provides a compound according to Formula Ia:

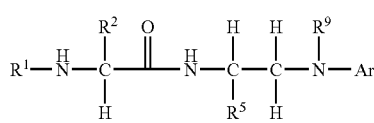

(Ia)

wherein:

$R^1$ is a member selected from the group of a 5- to 6-membered monocyclic or 8- to 10-membered bicyclic heteroaryl containing 1 to 4 heteroatoms each independently a member selected from the group of N, O and S, wherein at least one of said heteroatoms is nitrogen, and wherein said heteroaryl is substituted with 0–3 $R^{1a}$, and a $C_3$–$C_8$ heterocycle containing 1 to 2 heteroatoms each independently a member selected from the group of N, O and S, and wherein said heterocycle is substituted with 0–2 $R^{1a}$.

In certain preferred aspects, the present invention provides a compound wherien:

$R^1$ is a member selected from the group of pyridyl substituted with 0–3 $R^{1a}$, pyrazolyl substituted with 0–2 $R^{1a}$, thiazolyl substituted with 0–2 $R^{1a}$, isothiazolyl substituted with 0–2 $R^{1a}$, benzothiazolyl substituted with 0–3 $R^{1a}$, indolyl substituted with 0–3 $R^{1a}$, quinolinyl substituted with 0–3 $R^{1a}$, isoquinolinyl substituted with 0–3 $R^{1a}$, quinoxalinyl substituted with 0–3 $R^{1a}$, quinazolinyl substituted with 0–3 $R^{1a}$, phthalazinyl substituted with 0–3 $R^{1a}$, cinnolinyl substituted with 0–3 $R^{1a}$, pteridinyl substituted with 0–3 $R^{1a}$, furazanyl substituted with 0–1 $R^{1a}$, pyrrolyl substituted with 0–3 $R^{1a}$, oxazolyl substituted with 0–2 $R^{1a}$, isoxazolyl substituted with 0–2 $R^{1a}$, benzooxazolyl, substituted with 0–3 $R^{1a}$, indazolyl substituted with 0–3 $R^{1a}$, pyrimidinyl substituted with 0–3 $R^{1a}$, pyrazinyl substituted with 0–3 $R^{1a}$, pyridazinyl=substituted with 0–3 $R^{1a}$, purinyl with 0–3 $R^{1a}$, naphthpyridinyl substituted with 0–3 $R^{1a}$, imidazolyl substituted with 0–3 $R^{1a}$, oxazolo[4,5-b]pyridinyl substituted with 0–3 $R^{1a}$, oxazolo[4,5-c]pyridinyl substituted with 0–3 $R^{1a}$, oxazolo[5,4-b]pyridinyl substituted with 0–3 $R^{1a}$ and oxazolo[5,4-c]pyridinyl substituted with 0–3 $R^{1a}$.

In certain other preferred aspects, the present invention provides a compound wherien:

R is a member selected from the group of benzooxazolyl substituted with 0–3 $R^{1a}$, benzothiazolyl substituted with 0–3 $R^{1a}$, thiazolyl substituted with 0–2 $R^{1a}$, isoquinolinyl substituted with 0–3 $R^{1a}$, quinolinyl substituted with 0–3 $R^{1a}$, and pyrazinyl substituted with 0–3 $R^{1a}$.

In yet other preferred aspects, the present invention provides a compound wherien:

$R^2$ is a member selected from the group of a $C_1$–$C_4$ alkyl substituted with 1 $R^{2a}$, wherein said $C_1$–$C_4$ alkyl may optionally contain a heteroatom selected from the group of —O—, —S—, —S(=O)— and —S(=O)$_2$—, a $C_3$–$C_7$ cycloalkyl substituted with 0–2 $R^{1b}$, a $C_6$–$C_{11}$ bicycloalkyl substituted with 0–2 $R^{1b}$, tert-butyl-$CH_2$— and tert-butyl-$CH_2$—$CH_2$—; and each $R^{2a}$ is independently a member selected from the group of a $C_6$–$C_{10}$ aryl substituted with 0–3 $R^{1a}$, a $C_3$–$C_8$ cycloalkyl substituted with 0–2 $R^{1b}$, and a $C_6$–$C_{11}$ bicycloalkyl substituted with 0–2 $R^{1b}$.

In certain other preferred aspects, the present invention provides a compound wherien:

$R^2$ is a member selected from the group of a $C_1$–$C_2$ alkyl substituted with 1 $R^{2a}$, tert-butyl-$CH_2$—, and tert-butyl-$CH_2$—$CH_2$—; and each $R^{2a}$ is a $C_3$–$C_8$ cycloalkyl substituted with 0–2 $R^{1b}$.

In other preferred aspects, the present invention provides a compound wherien:

$R^5$ is a member selected from the group of H, C(=O)$OR^{24}$, C(=O)$NR^{25}R^{26}$, phenyl substituted with 0–2 $R^{21}$, $C_3$–$C_7$ cycloalkyl, and $C_1$–$C_6$ alkyl substituted with 0–1 $R^{23}$, wherein said $C_1$–$C_6$ alkyl may optionally contain a heteroatom selected from the group of —O—, —S—, —S(=O)—, —S(=O)$_2$— and $NR^{22}$—; and each $R^{23}$ is independently a member selected from the group of H, C(=O)$OR^{24}$, C(=O)$NR^{25}R^{26}$, $NR^{22}R^{27}$, $C_1$–$C_4$ alkoxy, phenyl substituted with 0–3 $R^{21}$, $C_3$–$C_8$ heterocycle containing 1 to 2 heteroatoms each independently a member selected from the group of N, O and S, wherein said heterocycle is substituted with 0–2 $R^{21}$ and is saturated or partially unsaturated, and $C_3$–$C_8$ cycloalkyl.

In a preferred aspect, the present invention provides a compound according to Formula Ib:

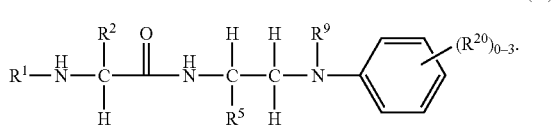

(Ib)

In another preferred aspect, the present invention provides a compound according to Formula Ic:

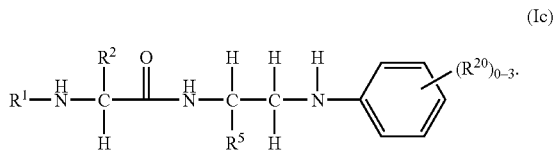

(Ic)

In yet another preferred aspect, the present invention provides a compound according to Formula Id:

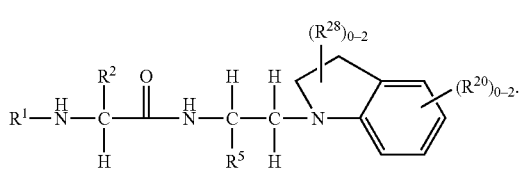

(Id)

In yet another preferred aspect, the present invention provides a compound wherein:
$R^2$ is a member selected from the group of tert-butyl-$CH_2$— and tert-butyl-$CH_2$—$CH_2$— and at least one of $R^5$, $R^6$, $R^7$, $R^8$ and $R^9$ is not H.

In certain other preferred aspects, the present invention provides wherein:
$R^1$ is a member selected from the group of benzooxazolyl substituted with 0–2 $R^{1a}$, benzothiazolyl substituted with 0–2 $R^{1a}$, thiazolyl substituted with 0–2 $R^{1a}$, isoquinolinyl substituted with 0–2 $R^{1a}$, quinolinyl substituted with 0–3 $R^{1a}$, and pyrazinyl substituted with 0–2 $R^{1a}$;
each $R^{1a}$ is independently a member selected from the group of F, Cl, Br, $C_1$–$C_4$ alkoxy, $SCH_3$, $S(=O)CH_3$, $S(=O)_2CH_3$, acetyl, $C(=O)OCH_3$, $CF_3$, $OCF_3$, phenyl substituted with 0–1 $R^{14}$, and a $C_1$–$C_4$ alkyl;
$R^2$ is a $C_1$–$C_2$ alkyl substituted with 1 $R^{2a}$;
each $R^{2a}$ is independently a member selected from the group of a $C_3$–$C_8$ cycloalkyl;
each of $R^3$, $R^6$, $R^7$, $R^8$ is H;
n is 0;
$R^5$ is a member selected from the group of H, and $C_1$–$C_6$ alkyl substituted with 0–1 $R^{23}$, wherein said $C_1$–$C_6$ alkyl may optionally contain a heteroatom selected from the group of —O—, —S—, and —S(=O)$_2$—;
$R^9$ is a member selected from the group of H and $C_1$–$C_6$ alkyl, Ar is a member selected from the group of phenyl substituted with 0–3 $R^{20}$, and 5-membered heteroaryl containing 1 to 2 heteroatoms each independently a member selected from the group of N, O and S, wherein said heteroaryl is substituted with 0–2 $R^{20}$;
each $R^{20}$ is independently a member selected from the group of H, F, Cl, Br, CN, $C_1$–$C_4$ alkoxy, OPh, OBn, $SCH_3$, $S(=O)CH_3$, $S(=O)_2CH_3$, $S(=O)_2N^{18}R^{19}$, $NR^{15}R^{16}$, acetyl, $C(=O)NR^{18}R^{19}$, $CO_2R^{18}$, $C(=NH)NH_2$, $C_1$–$C_6$ alkyl, $CF_3$, $OCF_3$ and
alternatively, $R^{20}$ and $R^9$ are taken together to form a 5-membered heterocyclic ring containing 1 nitrogen atom, wherein said heterocyclic ring is substituted with 0–2 $R^{28}$;
each $R^{23}$ is independently a member selected from the group of H, OH, F, Cl, CN, $C(=O)OR^{24}$, $C(=O)NR^{25}R^{26}$, $N^{22}R^{27}$, phenyl substituted with 0–3 $R^{21}$, $C_3$–$C_8$ heterocycle containing 1 to 2 heteroatoms each independently a member selected from the group of N, O and S, wherein said heterocycle is substituted with 0–2 $R^{21}$ and is saturated or partially unsaturated, and $C_3$–$C_8$ cycloalkyl;
$R^{22}$ is independently a member selected from the group of H, $^t$BOC, Cbz, ($C_1$–$C_6$ alkyl)-C(=O)—, ($C_1$–$C_6$ alkyl)-S(=O)$_2$—, a $C_1$–$C_6$ alkyl;
each $R^{24}$ is independently a member selected from the group of H, $C_1$–$C_4$ alkyl, a phenyl substituted with 0–3 $R^{14}$, and a benzyl substituted with 0–3 $R^{14}$;
each $R^{28}$ is independently a member selected from the group of F and $C_1$–$C_2$ alkyl;
alternatively, two $R^{28}$ on the same carbon may be combined to form $C_3$–$C_4$ cycloalkyl.

Compounds of the present invention are cathepsin S inhibitors. In particularly preferred aspects, the cathepsin S inhibitors are selective over cathepsin K, L, B, or combinations thereof.

In a further aspect, the present invention provides a compound according to Formula I, wherein $R^1$ has the following formula:

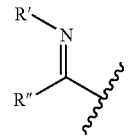

and R' and R" are each hydrogen, substituted or unsubstituted alkyl, substituted or unsubstituted aryl, substituted or unsubstituted heterocycle, substituted or unsubstituted cycloalkyl, or can be linked together to form a substituted or unsubstituted $C_5$–$C_8$ heterocycle containing 1–3 heteroatoms each independently selected from the group of N, O and S, and a substituted or unsubstituted $C_5$–$C_{10}$ heteroaryl containing 1–3 heteroatoms each independently selected from the group of N, O and S.

Preferred compounds of Formula I are set forth below in Table I:

TABLE I 1. (S)-2-(Benzooxazol-2-ylamino)-3-cyclohexyl-N-[2-(5-fluoro-2,3-dihydro-indol-1-yl)-ethyl]-propionamide;
2. (S)-2-(Benzooxazol-2-ylamino)-3-cyclohexyl-N-[2-(4-methoxy-phenylamino)-ethyl]-propionamide;

TABLE I-continued 3. 3-(S)-[2-(S)-(Benzooxazol-2-ylamino)-4,4-dimethyl-pentanoylamino]-4-(5-fluoro-2,3-dihydro-indol-1-yl)-butyric acid tert-butyl ester;
4. 3-(S)-[2-(S)-(Benzooxazol-2-ylamino)-4,4-dimethyl-pentanoylamino]-4-(5-fluoro-2,3-dihydro-indol-1-yl)-butyric acid;
5. 2-(S)-(Benzooxazol-2-ylamino)-4,4-dimethyl-pentanoic acid [1-(S)-(5-fluoro-2,3-dihydro-indol-1-ylmethyl)-3-methanesulfonyl-propyl]-amide;
6. 2-(S)-(Benzooxazol-2-ylamino)-4,4-dimethyl-pentanoic acid (R)-[1-benzyloxymethyl-2-(5-fluoro-2,3-dihydro-indol-1-yl)-ethyl]-amide;
7. 2-(S)-(Benzooxazol-2-ylamino)-4,4-dimethyl-pentanoic acid [2-(5-fluoro-2,3-dihydro-indol-1-yl)-1-(R)-hydroxymethyl-ethyl]-amide;
8. 2-(S)-(Benzooxazol-2-ylamino)-3-cyclohexyl-N-[2-(5-fluoro-2,3-dihydro-indol-1-yl)-1-(S)-methyl-ethyl]-propionamide;
9. 3-(S)-[2-(S)-(Benzooxazol-2-ylamino)-3-cyclohexyl-propionylamino]-4-(5-fluoro-2,3-dihydro-indol-1-yl)-butyric acid tert-butyl ester;
10. 2-(S)-(Benzooxazol-2-ylamino)-N-[1-(R)-(benzyloxymethyl-2-(5-fluoro-2,3-dihydro-indol-1-yl)-ethyl]-3-cyclohexyl-propionamide;
11. 2-(S)-(Benzooxazol-2-ylamino)-N-[1-(R)-benzyloxymethyl-2-(4-fluoro-phenylamino)-ethyl]-3-cyclohexyl-propionamide;
12. (S)-2-(Benzooxazol-2-ylamino)-4,4-dimethyl-pentanoic acid (R)-[2-(5-fluoro-2,3-dihydro-indol-1-yl)-1-methanesulfonylmethyl-ethyl]-amide;
13. 2-(S)-(5-Chloro-benzooxazol-2-ylamino)-3-cyclohexyl-N-[2-(4-fluoro-phenylamino)-ethyl]-propionamide;
14. 2-(S)-(6-Chloro-benzooxazol-2-ylamino)-3-cyclohexyl-N-[2-(4-fluoro-phenylamino)-ethyl]-propionamide;
15. 2-(S)-(7-Chloro-benzooxazol-2-ylamino)-3-cyclohexyl-N-[2-(4-fluoro-phenylamino)-ethyl]-propionamide;
16. 2-(S)-(Benzothiazol-2-ylamino)-3-cyclohexyl-N-[2-(5-fluoro-2,3-dihydro-indol-1-yl)-ethyl]-propionamide;
17. 2-(S)-(Benzothiazol-2-ylamino)-3-cyclohexyl-N-[2-(4-methoxy-phenylamino)-ethyl]-propionamide;
18. 4,4-Dimethyl-2-(S)-(pyrazin-2-ylamino)-pentanoic acid [2-(5-fluoro-2,3-dihydro-indol-1-yl)-ethyl]-amide;
19. 2-(S)-(Isoquinolin-1-ylamino)-4,4-dimethyl-pentanoic acid [2-(5-fluoro-2,3-dihydro-indol-1-yl)-ethyl]-amide;
20. (S)-3-Cyclohexyl-N-[2-(5-fluoro-2,3-dihydro-indol-1-yl)-ethyl]-2-(5-methyl-4-phenyl-thiazol-2-ylamino)-propionamide;
21. 2-(S)-(6-Chloro-benzothiazol-2-ylamino)-3-cyclohexyl-N-[2-(4-fluoro-phenylamino)-ethyl]-propionamide;
22. 3-Cyclohexyl-2-(S)-(6-fluoro-benzooxazol-2-ylamino)-N-[2-(4-fluoro-phenylamino)-ethyl]-propionamide;
23. 3-Cyclohexyl-2-(S)-(5-fluoro-benzooxazol-2-ylamino)-N-[2-(4-fluoro-phenylamino)-ethyl]-propionamide;
24. (S,S)2-{2-Cyclohexyl-1-[2-(4-fluoro-phenylamino)-1-methyl-ethylcarbamoyl]-ethylamino}-benzooxazole-6-carboxylic acid methyl ester;
25. 2-(S)-(7-Chloro-benzooxazol-2-ylamino)-3-cyclohexyl-N-[1-(S)-methyl-2-(5-methyl-isoxazol-3-ylamino)-ethyl]-propionamide;
26. 3-(S)-([2-(S)-(6-Chloro-benzooxazol-2-ylamino)-3-cyclohexyl-propionylamino]-4-(5-fluoro-2,3-dihydro-indol-1-yl)-butyric acid;
27. 3-(S)-[2-(S)-(6-Chloro-benzooxazol-2-ylamino)-3-cyclohexyl-propionylamino]-4-(5-fluoro-2,3-dihydro-indol-1-yl)-butyric acid ethyl ester;
28. 3-(S)-[2-(S)-(6-Chloro-benzooxazol-2-ylamino)-3-cyclohexyl-propionylamino]-4-(5-fluoro-2,3-dihydro-indol-1-yl)-butyric acid tert-butyl ester;
29. 3-(S)-[2-(S)-(6-Chloro-benzothiazol-2-ylamino)-3-cyclohexyl-propionylamino]-4-(5-fluoro-2,3-dihydro-indol-1-yl)-butyric acid;
30. 3-(S)-[2-(S)-(6-Chloro-benzothiazol-2-ylamino)-3-cyclohexyl-propionylamino]-4-(5-fluoro-2,3-dihydro-indol-1-yl)-butyric acid ethyl ester;
31. (S,S)-2-(6-Chloro-benzooxazol-2-ylamino)-3-cyclohexyl-N-[1-(5-fluoro-2,3-dihydro-indol-1-ylmethyl)-3-methanesulfonyl-propyl]-propionamide;
32. 2-(S)-(7-Chloro-benzooxazol-2-ylamino)-3-cyclohexyl-N-[2-(5-fluoro-2,3-dihydro-indol-1-yl)-1-(S)-methyl-ethyl]-propionamide;
33. 2-(S)-(6-Chloro-benzooxazol-2-ylamino)-3-cyclohexyl-N-[2-(5-fluoro-2,3-dihydro-indol-1-yl)-1-(S)-methyl-ethyl]-propionamide;
34. 2-(S)-(6-Chloro-benzothiazol-2-ylamino)-3-cyclohexyl-N-[2-(5-fluoro-2,3-dihydro-indol-1-yl)-1-(S)-methyl-ethyl]-propionamide;
35. 2-(S)-(7-Chloro-benzooxazol-2-ylamino)-3-cyclohexyl-N-[2-(4-methoxy-phenylamino)-1-(S)-methyl-ethyl]-propionamide;
36. 2-(S)-(7-Chloro-benzooxazol-2-ylamino)-3-cyclohexyl-N-[2-(4-methanesulfonyl-phenylamino)-1-(S)-methyl-ethyl]-propionamide;
37. 2-(S)-(7-Chloro-benzooxazol-2-ylamino)-3-cyclohexyl-N-[2-(3-methanesulfonyl-phenylamino)-1-(S)-methyl-ethyl]-propionamide;
38. 3-(S)-[2-(S)-(Benzooxazol-2-ylamino)-3-cyclohexyl-propionylamino]-4-(5-fluoro-2,3-dihydro-indol-1-yl)-butyric acid;
39. 2-(S)-(7-Chloro-benzooxazol-2-ylamino)-3-cyclopentyl-N-[1-(S)-methyl-2-(4-trifluoromethoxy-phenylamino)-ethyl]-propionamide;
40. 2-{2-Cyclohexyl-1-(S)-[2-(4-fluoro-phenylamino)-ethylcarbamoyl]-ethylamino}-benzooxazole-6-carboxylic acid methyl ester;
41. 2-(S)-(7-Chloro-benzooxazol-2-ylamino)-4,4-dimethyl-pentanoic acid [1-(S)-methyl-2-(4-trifluoromethoxy-phenylamino)-ethyl]-amide;

TABLE I-continued 42. 2-(S)-(Benzooxazol-2-ylamino)-3-cyclohexyl-N-[2-(4-fluoro-phenylamino)-ethyl]-propionamide;
43. 2-(S)-(7-Chloro-benzooxazol-2-ylamino)-3-cyclopropyl-N-[1-(S)-methyl-2-(4-trifluoromethoxy-phenylamino)-ethyl]-propionamide;
44. 2-(S)-(7-Chloro-benzooxazol-2-ylamino)-3-cyclohexyl-N-[2-(5-fluoro-3,3-dimethyl-2,3-dihydro-indol-1-yl)-1-(S)-methyl-ethyl]-propionamide;
45. 2-(S)-(7-Chloro-benzooxazol-2-ylamino)-3-cyclohexyl-N-[2-(5-fluoro-2,2-dimethyl-2,3-dihydro-indol-1-yl)-1-(S)-methyl-ethyl]-propionamide;

Compounds of the present invention are either obtained in the free form, or as a salt thereof if salt forming groups are present, or as esters if ester forming groups are present.

Compounds of the present invention that have acidic groups can be converted into salts with pharmaceutically acceptable bases, e.g., an aqueous alkali metal hydroxide, advantageously in the presence of an ethereal or alcoholic solvent, such as a lower alkanol. Resulting salts can be converted into the free compounds, e.g., by treatment with acids. These, or other salts can also be used for purification of the compounds obtained. Ammonium salts are obtained by reaction with the appropriate amine, e.g., diethylamine, and the like.

In certain aspects, compounds of the present invention having basic groups can be converted into acid addition salts, especially pharmaceutically acceptable salts. These are formed, for example, with inorganic acids, such as mineral acids, for example, sulfuric acid, a phosphoric or hydrohalic acid, or with organic carboxylic acids, such as ($C_1$–$C_4$) alkane carboxylic acids which, for example, are unsubstituted or substituted by halogen, for example, acetic acid, such as saturated or unsaturated dicarboxylic acids, for example, oxalic, succinic, maleic or fumaric acid, such as hydroxycarboxylic acids, for example, glycolic, lactic, malic, tartaric or citric acid, such as amino acids, for example, aspartic or glutamic acid, or with organic sulfonic acids, such as ($C_1$–$C_4$)-alkylsulfonic acids (for example, methanesulfonic acid) or arylsulfonic acids which are unsubstituted or substituted (for example, by halogen). Preferred are salts formed with hydrochloric acid, methanesulfonic acid and maleic acid.

In view of the close relationship between the free compounds and the compounds in the form of their salts or esters, whenever a compound is referred to in this context, a corresponding salt or ester is also intended, provided such is possible or appropriate under the circumstances.

The compounds, including their salts, can also be obtained in the form of their hydrates, or include other solvents used for their crystallization.

The compounds of the present invention that comprise free hydroxyl groups may also exist in the form of pharmaceutically acceptable, physiologically cleavable esters, and as such are included within the scope of the invention. Such pharmaceutically acceptable esters are preferably prodrug ester derivatives, such being convertible by solvolysis or cleavage under physiological conditions to the corresponding compounds of the present invention which comprise free hydroxyl groups. Suitable pharmaceutically acceptable prodrug esters are those derived from a carboxylic acid, a carbonic acid monoester or a carbamic acid, preferably esters derived from an optionally substituted lower alkanoic acid or an arylcarboxylic acid.

As will be apparent to one of skill in the art, certain compounds of the present invention possess asymmetric carbon atoms (optical centers) or double bonds; the racemates, diastereomers, enantiomers, geometric isomers and individual isomers are all intended to be encompassed within the scope of the present invention.

The present invention provides compounds which inhibit cathepsin S selectively. In certain preferred aspects, the present invention provides compounds which selectively inhibit cathepsin S in the presence of cathepsin isozymes, such as cathepsin A, B, C, D, E, F, G, H, K, L, M, O, P, Q, R, V, W, X and combinations thereof.

Compounds of the present invention useful for treating cathepsin S dependent conditions, preferably have cathepsin S inhibition constants less than 10 µM. More preferably, compounds of the present invention useful for treating cathepsin S dependent conditions have cathepsin S inhibition constants of less than 1.0 µM. Most preferably, compounds of the present invention useful for treating cathepsin S dependent conditions have cathepsin S inhibition constants of less than 0.1 µM.

In a preferred aspect, compounds of the present invention that selectively inhibit cathepsin S in the presence of a cathepsin isozyme (e.g. cathepsin K), have a cathepsin isozyme inhibition constant at least 10 times greater than their cathepsin S inhibition constant. In a more preferred aspect, compounds of the present invention that selectively inhibit cathepsin S in the presence of cathepsin isozyme, have a cathepsin isozyme inhibition constant at least 100 times greater than their cathepsin S inhibition constant. In a most preferred aspect, compounds of the present invention that selectively inhibit cathepsin S in the presence of cathepsin isozyme, have a cathepsin isozyme inhibition constant at least 1000 times greater than their cathepsin S inhibition constant.

IV. Compositions

The pharmaceutical compositions according to the invention are those suitable for enteral, such as oral or rectal, transdermal, topical, and parenteral administration to mammals, including humans, to inhibit cathepsin S activity, and for the treatment of cathepsin S dependent disorders, in particular neuropathic pain (see, WO 03/020287), Alzheimer's disease and certain autoimmune disorders, including, but not limited to, juvenile onset diabetes, multiple sclerosis, pemphigus vulgaris, Graves' disease, myasthenia gravis, systemic lupus erythemotasus, rheumatoid arthritis and Hashimoto's thyroiditis; allergic disorders, including, but not limited to, asthma; and allogeneic immune responses, including, but not limited to, rejection of organ transplants or tissue grafts.

More particularly, the pharmaceutical compositions comprise an effective cathepsin S inhibiting amount of a compound of the present invention.

The pharmacologically active compounds of the present invention are useful in the manufacture of pharmaceutical compositions comprising an effective amount thereof in conjunction or mixture with excipients or carriers suitable for either enteral or parenteral application.

Preferred are tablets and gelatin capsules comprising the active ingredient together with a) diluents, e.g., lactose, dextrose, sucrose, mannitol, sorbitol, cellulose and/or glycine; b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and or polyvinylpyrrolidone; if desired d) disintegrants, e.g., starches, agar, alginic acid or its sodium salt, or effervescent mixtures; and/or e) absorbents, colorants, flavors and sweeteners. Injectable compositions are preferably aqueous isotonic solutions or suspensions, and suppositories are preferably prepared from fatty emulsions or suspensions. The compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. The compositions are prepared according to conventional mixing, granulating or coating methods, respectively, and contain about 0.1 to 75%, preferably about 1 to 50%, of the active ingredient.

Tablets may be either film coated or enteric coated according to methods known in the art.

Suitable formulations for transdermal application include an effective amount of a compound of the present invention with carrier. Preferred carriers include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin. Matrix transdermal formulations may also be used.

Suitable formulations for topical application, e.g., to the skin and eyes, are preferably aqueous solutions, ointments, creams or gels well-known in the art. Such may contain solubilizers, stabilizers, tonicity enhancing agents, buffers and preservatives.

The pharmaceutical formulations contain an effective cathepsin S inhibiting amount of a compound of the present invention as defined above, either alone or in combination with another therapeutic agent.

In conjunction with another active ingredient, a compound of the present invention may be administered either simultaneously, before or after the other active ingredient, either separately by the same or different route of administration or together in the same pharmaceutical formulation.

The dosage of active compound administered is dependent on the species of warm-blooded animal (mammal), the body weight, age and individual condition, and on the form of administration. A unit dosage for oral administration to a mammal of about 50 to 70 kg may contain between about 5 and 500 mg of the active ingredient.

In a preferred aspect, the pharmaceutical composition of the present invention provides a compound according to Formula I.

In one aspect of the present invention, compositions of the present invention that comprise compounds of the present invention and pharmaceutically acceptable excipients, selectively inhibit cathepsin S in the presence of other cathepsin isozymes (e.g. cathepsin K).

In another aspect of the present invention, compositions of the present invention useful for treating cathepsin S dependent conditions, preferably have cathepsin S inhibition constants less than 10 µM. More preferably, compositions of the present invention useful for treating cathepsin S dependent conditions have cathepsin S inhibition constants of less than 1.0 µM. Most preferably, compositions of the present invention useful for treating cathepsin S dependent conditions have cathepsin S inhibition constants of less than 0.1 µM.

In a preferred aspect, compositions of the present invention utilize compounds that selectively inhibit cathepsin S in the presence of a cathepsin isozyme (e.g. cathepsin K), have a cathepsin isozyme inhibition constant at least 10 times greater than their cathepsin S inhibition constant. In a more preferred aspect, compounds of the present invention that selectively inhibit cathepsin S in the presence of cathepsin isozyme, have a cathepsin isozyme inhibition constant at least 100 times greater than their cathepsin S inhibition constant. In a most preferred aspect, compounds of the present invention that selectively inhibit cathepsin S in the presence of cathepsin isozyme, have a cathepsin isozyme inhibition constant at least 1000 times greater than their cathepsin S inhibition constant.

V. Methods

In view of their activity as inhibitors of cathepsin S, compounds of the present invention are particularly useful in mammals as agents for treatment and prophylaxis of diseases and medical conditions involving elevated levels of cathepsin S. For example, the compounds of the present invention are useful in treating Alzheimer's disease and certain autoimmune disorders, including, but not limited to juvenile onset diabetes, multiple sclerosis, pemphigus vulgaris, Graves' disease, myasthenia gravis, systemic lupus erythemotasus, rheumatoid arthritis and Hashimoto's thyroiditis; allergic disorders, including, but not limited to asthma; and allogeneic immune responses, including, but not limited to, rejection of organ transplants or tissue grafts.

Beneficial effects are evaluated in vitro and in vivo pharmacological tests generally known in the art, and as illustrated herein.

The above cited properties are demonstrable in vitro and in vivo tests, using advantageously mammals, e.g., rats, mice, dogs, rabbits, monkeys or isolated organs and tissues, as well as mammalian enzyme preparations, either natural or prepared by, e.g., recombinant technology. Compounds of the present invention can be applied in vitro in the form of solutions, e.g., preferably aqueous solutions or suspensions, and in vivo either enterally or parenterally, preferably orally, e.g., as a suspension or in aqueous solution, or as a solid capsule formulation. The dosage in vitro may range between about $10^{-5}$ molar and $10^{-9}$ molar concentrations. The dosage in vivo may range, depending on the route of administration, between about 0.1 and 100 mg/kg.

The antiarthritic efficacy of the compounds of the present invention for the treatment of rheumatoid arthritis can be determined using models such as, or similar to, the rat model of adjuvant arthritis, as described previously (R. E. Esser, et al., *J. Rheumatology* 1993, 20, 1176). The efficacy of the compounds of the present invention for the treatment of osteoarthritis can be determined using models such as, or similar to, the rabbit partial lateral meniscectomy model, as described previously (Colombo et al., *Arth. Rheum.* 1993, 26, 875–886). The efficacy of the compounds in the model can be quantified using histological scoring methods, as described previously (O'Byrne et al., *Inflamm. Res.* 1995, 44, S 177–S118).

The present invention also relates to methods of using compounds of the present invention and their pharmaceutically acceptable salts, or pharmaceutical compositions thereof, in mammals for inhibiting cathepsin S, and for the treatment of cathepsin S dependent conditions, such as the cathepsin S dependent conditions described herein, e.g., inflammation, rheumatoid arthritis and osteoarthritis.

In a preferred aspect, the present invention relates to a method of treating rheumatoid arthritis, osteoarthritis, and inflammation (and other diseases as identified above) in mammals comprising administering to a mammal in need thereof, a correspondingly effective amount of a compound of the present invention.

In a preferred aspect, the method of the present invention provides a compound according to Formula I.

Methods of the present invention useful for treating cathepsin S dependent conditions, preferably use compounds that have cathepsin S inhibition constants less than 10 µM. More preferably, methods of the present invention useful for treating cathepsin S dependent conditions use compounds that have cathepsin S inhibition constants of less than 1.0 µM. Most preferably, methods of the present invention useful for treating cathepsin S dependent conditions use compounds that have cathepsin S inhibition constants of less than 0.1 µM.

Moreover, the present invention relates to a method of selectively inhibiting cathepsin S activity in a mammal which comprises administering to a mammal in need thereof, an effective cathepsin S inhibiting amount of a compound of the present invention. In a preferred aspect, the methods of the present invention use compounds that selectively inhibit cathepsin S in the presence of a cathepsin isozyme, such as cathepsin A, B, C, D, E, F, G, H, K, L, M, O, P, Q, R, V, W, X and combinations thereof.

In a preferred aspect, methods of the present invention use compounds that selectively inhibit cathepsin S in the presence of a cathepsin isozyme (e.g. cathepsin K), have a cathepsin isozyme inhibition constant at least 10 times greater than their cathepsin S inhibition constant. In a more preferred aspect, compounds of the present invention that selectively inhibit cathepsin S in the presence of cathepsin isozyme, have a cathepsin isozyme inhibition constant at least 100 times greater than their cathepsin S inhibition constant. In a most preferred aspect, compounds of the present invention that selectively inhibit cathepsin S in the presence of cathepsin isozyme, have a cathepsin isozyme inhibition constant at least 1000 times greater than their cathepsin S inhibition constant.

VI. EXAMPLES

A. Compounds

General Procedure. All solvents stated as anhydrous were purchased that way from the manufacturer and used as received. All other purchased reagents were used as received. Unless otherwise stated, all reactions were carried out under a positive pressure of nitrogen. Silica gel chromatography was performed using pre-packed cartridges and an instrument for making a linear solvent gradient along with automated fraction collection. $^1$H NMR spectral data were reported as follows: chemical shift on the δ scale (using residual protio solvent as the internal standard), multiplicity (s=singlet, d=doublet, t=triplet, q=quartet, m=multiplet), integration and coupling constant in hertz. $^{13}$C spectra were recorded as APT experiments and were reported in ppm with residual solvent for internal standard.

Preparation 1. Synthesis of 2,2-dimethyl-5-fluoroindoline.

Step A: A solution of N-Boc-4-fluoroaniline (9.02 g, 42.7 mmol) in THF (112 mL) was cooled to −60° C. using a cryocool instrument. The solution was treated with 1.7 M t-BuLi in pentane (63 mL, 106.7 mmol) dropwise. After the first equivalent of base was consumed, a yellow solution formed. The reaction was allowed to warm to −20° C. and was stirred at that temperature for 2.5 hours. The reaction was then treated with a solution of methallyl bromide (5.67 g, 42.7 mmol) in THF (35 mL) dropwise and stirred for an additional 1.5 hours at −20° C. The reaction was then quenched by addition of water. After coming to room temperature, the reaction was treated with ethyl acetate and extracted with water and brine, dried over MgSO$_4$ and filtered. The solvent was then removed and the residue was purified on silica gel using a gradient of 0–25% ethyl acetate in hexane to afford 11.3 g (80% yield) of [4-Fluoro-2-(2-methyl-allyl)-phenyl]-carbamic acid tert-butyl ester as a white solid; $^1$H NMR (CDCl$_3$, 400 MHz) δ 1.50 (s, 9H), 1.72 (s, 3H), 3.28 (s, 2H), 4.71 (s, 1H), 4.92 (s, 1H), 6.32–6.50 (m, 1H), 6.86 (dd, 1H, J$_1$=3.0, J$_2$=9.1), 6.93 (ddd, 1H, J$_1$=3.0, J$_2$=8.5, J$_3$=11.5), 7.65–7.82 (m, 1H); HPLC-MS calcd. for C$_{15}$H$_{20}$FNO$_2$ (M+H$^+$−tBu) 210.1. found 210.3.

Step B: A sample of [4-Fluoro-2-(2-methyl-allyl)-phenyl]-carbamic acid tert-butyl ester (1.10 g, 4.14 mmol) was treated with anisole (5 mL), dichloromethane (5 mL) and trifluoroacetic acid (5 mL) and stirred for 4 hours. The solvent was removed and the reaction was transferred to a microwave reaction vial using methanesulfonic acid (3 mL). The reaction was heated to 170° C. for 10 minutes. The reaction was cooled to room temperature and quenched into excess stirring 1 M NaOH. The aqueous phase was extracted twice with ethyl acetate and the combined organics were dried over MgSO$_4$ and filtered. The resulting oil was purified on silica gel using a gradient of 0–70% t-butyl ethyl ether and hexane to afford 450 mg (66% yield) of 2,2-dimethyl-5-fluoroindoline; $^1$H NMR (CDCl$_3$, 400 MHz) δ 1.08 (s, 6H), 2.58 (s, 2H), 6.24 (dd, 1H, J$_1$=4.4, J$_2$=8.4), 6.43–6.48 (m, 1H), 6.53–6.56 (m, 1H); HPLC-MS calcd. for C$_{10}$H$_{12}$FN (M+H$^+$) 166.1. found 166.4.

Preparation 2. Synthesis of 3,3-dimethyl-5-fluoroindoline.

According to the procedure described in S. Coulton et al. WO9925709 with the following modifications. N-(4-Fluorophenyl)-N-(2-methyl-allyl)-acetamide (5 grams, 24.12 mmol) was added to a microwave tube with aluminum trichloride (7 grams, 52.4 mmol). The tube was capped and heated to 150° C. for 20 minutes under microwave. The slurry was worked up with water and ethyl acetate, the organic layer was extracted with 3 washes of saturated sodium bicarbonate solution and the organic layer was dried over magnesium sulfate. The solution was then filtered and rotary evaporated to yield pure 1-(5-Fluoro-3,3-dimethyl-2,3-dihydro-indol-1-yl)-ethanone in quantitative yield. This was converted to the free indoline by suspending the entire 5 grams of product in 20 mL of 6 M HCl and heating in a microwave to 200° C. for 10 minutes. The resulting 5-Fluoro-3,3-dimethyl-2,3-dihydro-1H-indole crystallized on cooling as the hydrochloride salt in quantitative yield. This material was identical to the previously reported compound.

Preparation 3. Synthesis of (S)-[1-Cyclopropyl-2-(5-fluoro-3,3-dimethyl-2,3-dihydro-indol-1-yl)-ethyl]-carbamic acid benzyl ester.

Step A: (S)-cyclopropyl glycine was prepared according to a modified procedure from that reported in D. J. Bayston et al. U.S. Pat. No. 6,191,306. A sample of (R)-phenethyl-(S)-cyclopropyl glycine (16.8 g, 76.7 mmol) was treated with THF (200 mL), water (100 mL) and 10% Pd/C (4.76 g). To the stirring mixture was added formic acid (17 mL) and the reaction was stirred overnight. The catalyst was then removed by filtration through a pad of celite and the solvent was removed by rotary evaporation. The material was co-evaporated with methanol several times and dried under vacuum to afford 4.75 g (54% yield) of the desired material as a solid which was used without further purification.

The material from the previous step (4.75 g, 41 mmol) was dissolved in 130 mL of 1 N NaOH and treated with benzyl chloroformate (5.92 g, 49.5 mmol) with vigorous stirring. The reaction was stirred overnight and then extracted with dichloromethane twice. The organics were discarded and the aqueous phase was acidified with conc. HCl and extracted with dichloromethane three times. The combined organics were dried over $MgSO_4$ and the solvent was removed to afford 7.38 g (72% yield) of the (S)-benzyloxycarbonylamino-cyclopropyl-acetic acid as a white solid.

Step B: A solution of (S)-benzyloxycarbonylamino-cyclopropyl-acetic acid (3.2 g, 12.8 mmol) in THF (20 mL) was cooled in an ice/water bath and treated with a 1 M solution of $BH_3$ in THF (16.7 mL, 16.7 mmol). The reaction was stirred for 4 hours and then treated with 1 M HCl until the bubbling ceased. The reaction was stirred overnight and the organic solvent was removed by rotary evaporation. The residue was treated with ethyl acetate and transferred to a separatory funnel. The aqueous phase was discarded and the organics were washed twice with 1 M NaOH, dried over $MgSO_4$ and the solvent was removed. The residue was purified on silica gel using a gradient of 0–100% ethyl acetate in hexane to afford 1.5 g (50% yield) of (S)-(1-Cyclopropyl-2-hydroxy-ethyl)-carbamic acid benzyl ester as a white solid; $^1H$ NMR ($CDCl_3$, 400 MHz) δ 0.26–0.37 (m, 1H), 0.34–0.44 (m, 1H), 0.47–0.61 (m, 2H), 0.83–0.94 (m, 1H), 2.95–3.04 (m, 1H), 3.70 (dd, 1H, $J_1$=5.8, $J_2$=11.1), 3.79–3.88 (m, 1H), 5.00–5.12 (m, 1H), 5.10 (s, 2H), 7.29–7.31 (m, 5H); HPLC-MS calcd. for $C_{13}H_{17}NO_3$ (M+H$^+$) 236.1. found 236.3.

Step C: (S)-[1-Cyclopropyl-2-(5-fluoro-3,3-dimethyl-2,3-dihydro-indol-1-yl)-ethyl]-carbamic acid benzyl ester was prepared in 67% yield an analogous manner to example 12, except that the alcohol from the previous step and 1 equivalent of 3,3-dimethyl-5-fluoroindoline (WO 9925709) were used as coupling partners; HPLC-MS calcd. for $C_{23}H_{27}FN_2O_2$ (M+H$^+$) 383.2. found 383.4.

Preparation 4. Synthesis of (S)-[1-Cyclopropyl-2-(5-fluoro-3,3-spirocycloprpyl-indol-1-yl)-ethyl]-carbamic acid benzyl ester.

Step A: A solution of 5-fluoroisatin (5 g, 30.2 mmol) in DMF (60 mL) was cooled in an ice/water bath and treated with sodium hydride (1.44 g, 60.6 mmol) portionwise. The reaction was stirred for 15 minutes after the addition of the last portion and then treated with p-methoxybenzyl chloride (5.32 g, 45.3 mmol) and allowed to stir for 1 hour. The reaction was then quenched by slow addition of excess methanol. After bubbling had stopped, the reaction was poured into water (100 mL) and extracted twice with ethyl acetate. The organics were combined, dried over $MgSO_4$ and the solvent was removed. The residue was purified by silica gel chromatography using a gradient of 0–100% ethyl acetate in hexane to afford 7.1 g (82%) of 5-Fluoro-1-(4-methoxy-benzyl)-1H-indole-2,3-dione; $^1H$ NMR ($CDCl_3$, 400 MHz) δ 3.79 (s, 3H), 4.86 (s, 2H), 6.75 (dd, 1H, $J_1$=3.6, $J_2$=8.6), 6.84–6.90 (m, 2H), 7.19 (ddd, 1H, $J_1$=$J_2$=8.6, $J_3$=3.6), 7.22–7.27 (m, 1H), 7.26–7.31 (m, 2H); HPLC-MS calcd. for $C_{16}H_{12}FNO_3$ (M+H$^+$) 286.1. found 286.3.

Step B: A solution of 5-fluoro-1-(4-methoxy-benzyl)-1H-indole-2,3-dione (7.1 g, 24.9 mmol) in hydrazine hydrate (35 mL) and ethanol (15 mL) was refluxed overnight, diluted with water and extracted twice with ethyl acetate. The combined organics were dried over $Na_2SO_4$, filtered and concentrated. The residue was purified by silica gel chromatography using a gradient of 0–100% ethyl acetate in hexane to afford 6.1 g (90%) of 5-fluoro-1-(4-methoxy-benzyl)-1,3-dihydro-indol-2-one; $^1H$ NMR ($CDCl_3$, 400 MHz) δ 3.59 (s, 2H), 3.77 (s, 3H), 4.83 (s, 2H), 6.63 (dd, 1H, $J_1$=4.2, $J_2$=8.6), 6.82–6.91 (m, 3H), 6.96–7.01 (m, 1H), 7.19–7.23 (m, 1H), 7.27–7.31 (m, 1H); HPLC-MS calcd. for $C_{16}H_{14}FNO_2$ (M+H$^+$) 272.1. found 272.3.

Step C: A solution of 5-fluoro-1-(4-methoxy-benzyl)-1,3-dihydro-indol-2-one (6.12 g, 22.6 mmol) in DMF (65 mL) was cooled in an ice/water bath and treated with dibromoethane (6.35 g, 33.8 mmol) followed by sodium hydride (1.09 g, 45 mmol) portionwise. After stirring at 0° C. for 1 hour, the reaction was cooled to −78° C. and treated with excess methanol. After bubbling had stopped, the reaction was poured into water (100 mL) and extracted twice with ethyl acetate. The organics were combined, dried over $Na_2SO_4$ and the solvent was removed. The residue was purified by silica gel chromatography using a gradient of 0–100% ethyl acetate in hexane to afford 4.1 g (61%) of 5-fluoro-1-(4-methoxy-benzyl)-siprocyclopropyloxindole; $^1H$ NMR ($CDCl_3$, 400 MHz) δ 1.54 (dd, 2H, J1=4.0, $J_2$=7.8), 1.83 (dd, 2H, $J_1$=4.3, $J_2$=8.1), 3.77 (s, 3H), 4.91 (s, 2H), 6.57 (dd, 1H, $J_1$=2.5, $J_2$=8.0), 6.69 (dd, 1H, $J_1$=4.2, $J_2$=8.5), 6.81 (dd, 1H, $J_1$=2.5, $J_2$=9.3), 6.83–6.87 (m, 2H), 7.22–7.25 (m, 2H); HPLC-MS calcd. for $C_{18}H_{16}FNO_2$ (M+H$^+$) 298.1. found 298.3.

Step D: A solution of 5-fluoro-1-(4-methoxy-benzyl)-siprocyclopropyloxindole (3.38 g, 11.4 mmol) in TFA (20 mL) was stirred at 60° C. overnight. The solvent was then removed and the reaction was diluted with ethyl acetate and washed with saturated aqueous $NaHCO_3$ until the washings were neutral. The organic phase was then washe with brine, dried over $Na_2SO_4$ and the solvent was removed. The residue was purified by silica gel chromatography using a gradient of 0–100% ethyl acetate in hexane to afford 1.94 g (96%) of 5-fluoro-siprocyclopropyloxindole; $^1H$ NMR (MeOD, 400 MHz) δ 1.76–1.86 (m, 4H), 6.91–6.94 (m, 1H), 7.07–7.11 (m, 2H); HPLC-MS calcd. for $C_{10}H_8FNO$ (M+H$^+$) 178.2. found 178.3.

Step E: A sample of 5-fluoro-siprocyclopropyloxindole (172 mg, 97 μmol) was cooled in an ice/water bath and treated with a 1.0 M solution of LAH (1.94 ml, 1.9 mmol). The reaction was stirred at room temperature for 15 minutes and then at 50° C. for 3 hours and finally was cooled back down with an ice/water bath. The reaction was treated with 1 M NaOH (1.9 mL) followed by water (1.9 mL). The reaction was filtered over celite and dried over $MgSO_4$. After filtration, the solvent was removed and the crude material of 5-fluoro-siprocyclopropylindoline was used as the indoline partner to prepare [1-Cyclopropyl-2-(5-fluoro-3,3-spirocycloprpyl-indol-1-yl)-ethyl]-carbamic acid benzyl ester in 62% yield in an analogous manner to example 12, step A; HPLC-MS calcd. for $C_{23}H_{25}FN_2O_2$ (M+H$^+$) 381.2. found 381.4.

In addition, synthesis of other 3,3-spiro-cycloalkylindolines are also described in (1) Jackson, A. H. et al. Tetrahedron (1968), 24(1), 403–13; (2) Jansen, A. B. A. et al. Tetrahedron (1965), 21(6), 1327–31; (3) Bermudez, J. et al. J.Med. Chem. (1990), 33(7), 1929–32; (4) Nishio, T. et al. Helv. Chim. Acta (1990), 73(6), 1719–23; (5) Nishio, T. et al. J. Chem. Soc., Perkin Trans 1 (1991), (1), 141–3; (6) Kucerovy, A. et al. Synth. Commun. (1992), 22(5), 729–33; (7) Kato, M. et al. Chem. Pharm. Bull. (1995), 43(8), 1351-7.

Preparation 6. Synthesis of (S)-2-(4-Methoxy-phenylamino)-1-methyl ethyl amine.

Step A: Preparation of (S)-2-(tert-Butoxycarbonylamino)-propionaldehyde. (S)-(−)-2-(tert-Butoxycarbonylamino)-1-propanol (523 mg, 2.98 mmol, 1.0 equiv.) was dissolved in 45 mL methylene chloride in a 100 mL r.b. flask with a magnetic stir bar. To this clear homogeneous solution, Dess-Martin periodinane (1.523 g, 3.591 mmol, 1.2 equiv.) was added in one part and the cloudy white reaction mixture was allowed to stir at room temperature for 2 h. Thin-layer chromotography monitored the reaction to completion. The reaction mixture was diluted with 100 mL ethyl acetate. Sodium bisulfite solution (2 M, 20 mL) was added to the reaction mixture and the organic layer was separated. The aqueous layer was washed with 3×30 mL EtOAc. The combined organic layers were washed with 50 mL 1 M NaOH, followed by saturated NaCl (30 mL) and dried over $MgSO_4$. Filtration and rotary evaporation produced the desired product as a yellow oil (475 mg, 92% yield, Rf=0.63, 1:1 hexanes/ethyl acetate).

Step B: Preparation of [2-(4-methoxy-phenylamino)-(1S)-methyl-ethyl]-carbamic acid tert-butyl ester.

(S)-2-(tert-Butoxycarbonylamino)-propionaldehyde (473 mg, 2.74 mmol) and p-anisidine (1.031 g, 8.371 mmol, 3.0 equiv.) was dissolved in 45 mL of MeOH at 0° C. in a 100 mL r.b. flask with a magnetic stir bar. Optionally, acetic acid (469 μL, 8.21 mmol, 3.0 equiv.) can be added via syringe to assist in the reaction. To the stirring dark colored solution was added sodium cyanoborohydride (326 mg, 5.82 mmol, 1.89 equiv.). Gas evolution and disappearance of color were observed. The reaction was allowed to slowly warm to room temperature with stirring over 30 minutes and the reaction was monitored by LC/MS. At the completion of the reaction, the mixture was quenched with 1 M NaOH, and extracted 3×50 mL ethyl acetate. The resulting organics were washed with 50 mL saturated $NaHCO_3$, 40 mL saturated NaCl, and dried over $MgSO_4$. Evaporation of ethyl acetate provided 728 mg of a brown oil. Purification by automated ISCO chromatography provided a clear oil of [2-(4-methoxy-phenylamino)-(1S)-methyl-ethyl]-carbamic acid tert-butyl ester (583 mg, 2.079 mmol, 76% yield). HPLC-MS calcd. for $C_{15}H_{24}N_2O_3$ (M+H+) 281.2. found 281.5. 1H NMR ($CDCl_3$, 400 MHz) δ 1.21 (d, 6H, J=6.6 Hz), 1.47 (s, 9H), 3.05 (dd, 1H, J=12.2, 7.3 Hz), 3.13 (dd, 1H, J=12.2, 4.6 Hz), 3.76 (s, 3H), 3.93 (broad s, 1H), 4.62 (broad s, 1H), 6.60 (d, 2H, J=6.8 Hz), 6.80 (2H, d, J=6.8 Hz).

Step C: [2-(4-Methoxy-phenylamino)-(1S)-methyl-ethyl]-carbamic acid tert-butyl ester (383 mg, 1.37 mmol) was added to 10 mL of a trifluroacetic acid solution (10 v/v % in methylene chloride) at room temperature in a 25 mL r.b. flask with a magnetic stirbar. The reaction turns dark purple/black in color after 5 minutes. The reaction is allowed to stir at room temperature until the reaction is judged complete by HPLC/MS. The solvent is removed by evaporation and to provide 2-(4-Methoxy-phenylamino)-(1S)-methyl-ethyl-ammonium trifluoroacetate salt as a brown oil (394 mg, 1.34 mmol, 98% yield) and used directly in the next reaction. HPLC-MS calcd. for $C_{10}H_{16}N_2O$ (M+H+) 181.1. found 181.5.

Preparation 7. (R)-3-Benzyloxy-N-1-(4-methoxy-phenyl)-propane-1,2-diamine.

Step A: N-Boc-OBn-Serine (750 mg, 2.54 mmol), p-anisidine (344 mg, 2.79 mmol) and HOBt (377 mg, 2.79 mmol) were charged to a 50 mL roundbottom flask and treated with $CH_2Cl_2$ (6 mL). The reaction was then treated with EDCI (535 mg, 2.79 mmol) and allowed to stir for 2 hours. The reaction was then diluted with ethyl acetate and extracted twice with water, twice with 1 M HCl and twice with 1 M NaOH. The organics were then dried over $MgSO_4$ and the solvent was removed to afford 450 mg (44%) of a white solid: $^1$H NMR ($CDCl_3$, 400 MHz) δ 1.49 (s, 9H), 3.63–3.72 (m, 1H), 3.81 (s, 3H), 4.00–4.08 (m, 1H), 4.47–4.50 (m, 1H), 4.55–4.70 (m, 2H), 5.45–5.60 (m, 1H), 6.87 (d, 2H, J=8.8), 7.30–7.41 (m, 7H), 8.20–8.33 (m, 1H); HPLC-MS calcd. for $C_{22}H_{28}N_2O_5$ (M+H+) 401.2. found 401.4.

Step B: The product from Step A (400 mg, 1.00 mmol) was added to an ice cold solution of borane (1 M) in THF. The cooling bath was removed and the reaction was allowed to stir for 24 h at which point the excess reagent was quenched using 5% NaHSO4. The reaction was diluted with ethyl acetate and extracted twice with 1 M NaOH. The organics were dried over $MgSO_4$ and the solvent was removed. The resulting residue contained material that was missing the Boc group and some material that still had it (by HPLC-MS). The oil was treated with MeOH (2 mL) and 4 M HCl (2 mL) and stirred for 3 hours. The solvent was then removed and the reaction was partitioned between ethyl acetate and 1 M NaOH. The aqueous phase was extracted twice more with ethyl acetate and the combined organics were dried over MgSO4 and the solvent was removed.

Preparation 8. Synthesis of (S)-N-1-(4-trifluoromethoxy-phenyl)-propane-1,2-diamine.

Step A: (S)-2-(benzylcarbonylamino)-propionaldehyde. (S)-2-(benzylcarbonylamino)-propanol (5 g, 23.9 mmol) was dissolved in $CH_2Cl_2$ (200 mL) and treated with Dess-Martin periodinane (12.26 g, 1.1 eq). The mixture was stirred for 2 hours, then quenched with sodium thiosulphate, and the solvent removed in vacuo. The residue was then separated between sodium hydroxide (1M, 500 mL) and ethyl acetate (500 mL). The organics were washed with brine, dried ($MgSO_4$) and evaporated in vacuo to yield a clear oil which was used immediately in the next step without further purification.

Step B:[1-(S)-Methyl-2-(4-trifluoromethoxy-phenylamino)-ethyl]-carbamic acid benzyl ester.

(S)-2-(benzylcarbonylamino)-propionaldehyde was dissolved in methanol (300 mL). Acetic acid (4 mL, 2.9 eq) was added and the mixture treated with 4-trifluoromethoxy aniline (9.6 mL, 3 eq) and stirred for 15 minutes then sodium cyanoborohydride (4.36 g, 2.9 eq) was added with some effervescence. The mixture was stirred for 3 hours, and then the solvent reduced in vacuo. This was then separated between hydrochloric acid (1M, 500 mL×2) and ethyl acetate (500 mL). The organics were washed with sodium bicarbonate (500 mL), brine (500 mL), dried ($MgSO_4$) and evaporated in vacuo to give a clear oil which was purified by silica gel chromatography eluted with a gradient of 0–100% ethyl acetate/hexane.

Step C: (S)-N-1-(4-Trifluoromethoxy-phenyl)-propane-1,2-diamine.

[1-(S)-Methyl-2-(4-trifluoromethoxy-phenylamino)-ethyl]-carbamic acid benzyl ester (23.9 mmol) was dissolved in ethanol (200 mL) then placed under nitrogen. 10% Palladium on carbon was added (0.5 g) and the mixture was stirred under hydrogen (atmospheric pressure) overnight. When reaction was complete, the mixture was filtered through celite. The celite was washed with ethanol (5×50 ml) then evaporated in vacuo to give a brown oil (4.03 g, 17.21 mmol, 72% yield over 3 steps).

Preparation 9. Synthesis of 2,2,5-trifluoroindoline.

Step A: 5-Fluoro-1H-indole-2,3-dione (956 mg, 5.79 mmol, 1 eq) was added as a solution in dry DMF to a stirred slurry of sodium hydride (278 mg, 11.6 mmol, 2 eq) in dry DMF drop wise over 15 minutes under an inert atmosphere with adequate pressure release to accommodate $H_2$ evolution. The resulting mixture was stirred for 1 hour and p-methoxybenzyl chloride was added via syringe to the reaction. The solution was then stirred for 2 hours and worked up by addition of water followed by extraction into ethyl acetate. The organic layer was washed twice with water and then dried over $MgSO_4$. Column chromatography with ethyl acetate/hexane afforded 5-Fluoro-1-(4-methoxy-benzyl)-1H-indole-2,3-dione as a red solid (1.3 g, 80% yield). $^1$H NMR (CDCl$_3$) δ (ppm): 7.3–7.24 (m, 3H), 7.20 (td, J=8.7, 2.7 Hz, 1H), 6.9–6.86 (m, 2H), 6.76 (dd, J=8.6, 3.6Hz, 1H), 3.81 (s, 2H), 3.78 (s, 3H). LC/MS=286.1 (M+1).

Step B: The product from step A (200 mg, 0.701 mmol, 1 eq) was dissolved in 10 mL of dry DCM and placed under and inert atmosphere. DAST (339 mg, 2.103 mmol, 3 eq) was added via syringe and the reaction was stirred overnight. The reaction was worked up by addition of saturated aqueous sodium bicarbonate and the organic layer was dried over $MgSO_4$, filtered, and rotary evaporated to dryness. The resulting crude material was purified by flash chromatography using ethyl acetate/hexane as a solvent system. $^1$H NMR (CDCl$_3$) δ (ppm): 7.3–7.28 (m, 1H), 7.22 (d, J=8.7 Hz, 2H), 7.09 (td, J=8.7, 1.3 Hz, 1H), 6.87 (d, J=8.7 Hz, 2H), 6.73 (m, 1H), 4.83 (s, 2H), 3.79 (s, 3H). LC/MS=308.1(M+1).

Step C: The product from step B (1.178 g, 3.83 mmol, 1 eq) was dissolved in 75 mL of dry THF and placed under an inert atmosphere. LiAlH$_4$ (291 mg, 7.66 mmol, 2 eq) was added as a solid under a positive pressure of $N_2$ at −78° C. The reaction was allowed to stir at this temperature for 30 min and then allowed to warm to room temp over a period of 6 hours. The reaction was worked up by addition of water dropwise followed by 4 equivalents of aqueous KOH. The slurry was diluted with 500 mL of water and extracted with 2×200 mL portions of ethyl acetate. The organic layers were combined, dried over $MgSO_4$, filtered, and rotary evaporated to dryness. The resulting crude material was purified by flash chromatography using ethyl acetate/hexane as a solvent system yielding 320 mg of pure material (28%). $^1$H NMR (CD3OD) δ (ppm): 7.21 (d, J=8.8 Hz, 2H), 7.06 (dd, J=8.2, 1.3 Hz, 1H), 6.89 (m, 1H), 6.84 (d, J=8.7 Hz, 2H), 6.77 (dd, J=8.6, 4.3 Hz, 1H), 4.83 (s, 2H), 3.73 (s, 3H), 3.12 (s, 2H). LC/MS=294.1(M+1).

Step D: The product from step C (50 mg, 0.1704 mmol, 1 eq) was taken up in 1 mL of TFA. The solution was placed in a microwave tube, sealed, and heated to 175° C. for 5 minutes. The resulting black solution was neutralized with saturated sodium bicarbonate and extracted with 2×50 mL portions of ethyl acetate. The organic layers were dried over $MgSO_4$, filtered, and rotary evaporated to dryness. The resulting solid was dissolved in a 50:50 mix of DMSO/MeOH and purified by prep HPLC. Yield 23.8 mg of white solid (81%). $^1$H NMR (DMSO D6) δ (ppm): 10.41 (s, 1H), 7.13 (dd, J=8.6, 2.4 Hz, 1H), 7.01 (td, J=8.6, 2.7 Hz, 1H), 6.8 (dd, J=8.5, 4.5 Hz, 1H), 3.5 (s, 2H).

Example 1

(S)-2-(Benzooxazol-2-ylamino)-3-cyclohexyl-N-[2-(5-fluoro-2,3-dihydro-indol-1-yl)-ethyl]-propionamide. The title compound was prepared from 2-(S)-(benzooxazol-2-ylamino)-3-cyclohexyl propionic acid and 2-(5-fluoro-2,3-dihydro-indol-1-yl)-ethylamine using the procedure analogous to that described in example 2. HPLC-MS calcd. for $C_{26}H_{31}FN_4O_2$ (M+H$^+$) 451.24. found 451.5.

Example 2

(S)-2-(Benzooxazol-2-ylamino)-3-cyclohexyl-N-[2-(4-methoxy-phenylamino)-ethyl]-propionamide Step A. A slurry of L-cyclohexylalanine (2.44 g, 14.3 mmol) and powdered NaOH (1.14 g, 28.6 mmol) in DMSO (20 mL) was heated to 100° C. for 20 min until the mixture viscosity decreased and stirring was enabled. 2-Chlorobenzoxazole (1.99 g, 13.0 mmol) was added, and the solution was stirred at 100° C. for 4 h. Upon cooling to room temperature, the solution was poured into 1 M HCl. The precipitate was filtered and dried to afford 2-(S)-(benzooxazol-2-ylamino)-3-cyclohexyl propionic acid was isolated as a white powder (1.69 g, 41%).

Step B. To a stirring solution of 2-(S)-(benzooxazol-2-ylamino)-3-cyclohexyl propionic acid (288 mg, 1.0 mmol), N1-(4-methoxy-phenyl)-ethane-1,2-diamine.2HCl (239 mg, 1.0 mmol), and $^i$Pr$_2$NEt (0.87 mL, 5.0 mmol) in dichloromethane (4 mL) was added HATU (418 mg, 1.1 mmol). The solution was stirred at room temperature for 4 hours and then evaporated to dryness. The crude material was chromatographed over silica gel (Hexanes/EtOAc) to afford the title compound as a white powder (243 mg, 56%). HPLC-MS calcd. for $C_{25}H_{32}N_4O_3$ (M+H$^+$) 437.25. found 437.5.

Example 3

3-(S)-[2-(S)-(Benzooxazol-2-ylamino)-4,4-dimethyl-pentanoylamino]-4-(5-fluoro-2,3-dihydro-indol-1-yl)-butyric acid tert-butyl ester Step A. 2-(S)-(Benzooxazol-2-ylamino)-4,4-dimethyl-pentanoic acid: (S)-t-Bu-alanine (1.00 g, 6.9 mmol), 2-chlorobenzoxazole (1.16 g, 7.6 mmol), potassium hydroxide (850 mg, 15.2 mmol) and 18-crown-6 (1.82 g, 6.9 mmol) were treated with DMSO (10 mL) and dipped into a preheated 100° C. oil bath. The reaction was allowed to stir for 2 h and then cooled to room temperature. The reaction solution was poured into a 200 mL of 1 M HCl. The resulting solution was filtered, saturated with NaCl and extracted with ethyl acetate 3 times and discarded. The combined ethyl acetate portions were extracted with 1 M NaOH 3 times and discarded. The basic aqueous extracts were made acidic with concentrated HCl and extracted twice with ethyl acetate. The combined ethyl acetate portions were dried over $MgSO_4$ and the solvent was removed. The resulting oil was crystallized from diethyl ether to obtain 850 mg of material (47%): $^1$H NMR (CDCl$_3$, 400 MHz) δ 1.03 (s, 9H), 1.73 (dd, 1H, $J_1$=9.5, $J_2$=14.4), 1.91 (dd, 1H, $J_1$=2.4, $J_2$=14.4), 4.45 (dd, 1H, $J_1$=2.4, $J_2$=9.5), 7.01–7.06 (m, 1H), 7.12–7.17 (m, 1H), 7.23–7.30 (m, 2H); HPLC-MS calcd. for $C_{14}H_{18}N_2O_3$ (M+H$^+$) 263.1. found 263.4.

Step B. (S)-3-Benzyloxycarbonylamino-4-(5-fluoro-2,3-dihydro-indol-1-yl)-butyric acid tert-butyl ester. This material was prepared in an analogous manner to example 12, step C using N-Cbz-OtBu-Asp amino alcohol and 5-fluoroindoline in 71% yield. HPLC-MS calcd. for $C_{24}H_{29}FN_2O_4$ (M+H$^+$) 429.2. found 429.4.

Step C. 3-(S)-[2-(S)-(Benzooxazol-2-ylamino)-4,4-dimethyl-pentanoylamino]-4-(5-fluoro-2,3-dihydro-indol-1-yl)-butyric acid tert-butyl ester. The title compound of step B (105 mg, 246 μmol) was dissolved in methanol (2 mL) and treated with 10% Pd/C (10 mg). The atmosphere in the reaction was then exchanged for hydrogen by sparging the solution with a long needle for 3 minutes. The reaction was then stirred under an atmosphere of hydrogen for 3 hours. The atmosphere in the vessel was swapped back to nitrogen by sparging with a long needle for 3 minutes. The catalyst was removed by filtration through celite and the solvent was removed. The resulting oil was coevaporated with dichloromethane 3 times. To the residue was added the title compound of step A (71 mg, 270 μmol), HATU (112 mg, 294 μmol), dry dichloromethane (2 mL) and diisopropylethylamine (63 mg, 492 μmol). The reaction was allowed to stir overnight. The reaction contents were then poured into a separatory funnel and treated with saturated sodium bicarbonate solution. The aqueous solution was extracted twice with dichloromethane and the combined organics were dried over MgSO$_4$ and the solvent was removed. The residue was purified by automated silica gel chromatography using a linear gradient of 0 to 100% ethyl acetate in hexane to afford the title compound as a solid (97 mg, 73%): $^1$H NMR (CDCl$_3$, 400 MHz) δ 0.89 (s, 9H), 1.30 (s, 9H), 1.54 (dd, 1H, $J_1$=8.9, $J_2$=14.6), 1.85 (dd, 1H, $J_1$=3.3, $J_2$=14.6), 2.44 (dd, 1H, $J_1$=5.9, $J_2$=16.1), 2.54 (dd, 1H, $J_1$=5.3, $J_2$=16.1), 2.65–2.82 (m, 2H), 2.99 (dd, 1H, $J_1$=7.2, $J_2$=13.8), 3.13 (dd, 1H, $J_1$=6.3, $J_2$=13.8), 3.22 (dd, 1H, $J_1$=8.5, $J_2$=16.9), 3.29 (dd, 1H, $J_1$=8.7, $J_2$=16.3), 4.25–4.40 (m, 2H), 5.84–5.95 (m, 1H), 6.27 (dd, 1H, $J_1$=4.1, $J_2$=8.5), 6.53–6.60 (m, 1H), 6.62–6.68 (m, 1H), 6.95 (dd, 1H, $J_1$=$J_2$=7.7), 7.03–7.15 (m, 3H), 7.25 (d, 1H, $J_1$=7.7); HPLC-MS calcd. for $C_{30}H_{39}FN_4O_4$ (M+H$^+$) 539.3. found 539.5.

Example 4

3-(S)-[2-(S)-(Benzooxazol-2-ylamino)-4,4-dimethyl-pentanoylamino]-4-(5-fluoro-2,3-dihydro-indol-1-yl)-butyric acid. The title compound of Example 3 (90 mg, 167 μmol) was treated with 2 mL of a solution containing 45% trifluoroacetic acid, 45% dichloromethane and 10% water. The material was allowed to stand overnight and the solvent was removed to afford the TFA salt of the title compound as an oil (95 mg, 95%): $^1$H NMR (CD$_3$OD, 400 MHz) δ 0.96 (s, 9H), 1.67 (dd, 1H, $J_1$=8.9, $J_2$=14.6), 1.81 (dd, 1H, $J_1$=3.4, $J_2$=14.6), 2.63 (d, 2H, $J_1$=6.8), 2.71–2.89 (m, 2H), 3.03 (dd, 1H, $J_1$=5.6, $J_2$=13.7), 3.21–3.33 (m, 2H), 3.41–3.51 (m, 1H), 4.35 (dd, 1H, $J_1$=3.3, $J_2$=8.9), 4.43–4.52 (m, 1H), 6.42 (dd, 1H, $J_1$=4.2, $J_2$=8.5), 6.57–6.64 (m, 1H), 6.67–6.73 (m, 1H), 7.13–7.18 (m, 1H), 7.22–7.28 (m, 1H), 7.28–7.33 (m, 1H), 7.35 (d, 1H, $J_1$=8.0); HPLC-MS calcd. for $C_{26}H_{31}FN_4O_4$ (M+H$^+$) 483.2. found 483.5.

Example 5

2-(S)-(Benzooxazol-2-ylamino)-4,4-dimethyl-pentanoic acid [1-(S)-(5-fluoro-2,3-dihydro-indol-1-ylmethyl)-3-methanesulfonyl-propyl]-amide Step A. (S)-[1-(5-Fluoro-2,3-dihydro-indol-1-ylmethyl)-3-methanesulfonyl-propyl]-carbamic acid tert-butyl ester. This material was prepared in 72% yield in an analogous manner to Example 12: $^1$H NMR (CD$_3$OD, 400 MHz) δ 1.56 (s, 9H), 2.01–2.16 (m, 1H), 2.32–2.43 (m, 1H), 3.06 (s, 3H), 3.07 (dd, 2H, $J_1$=$J_2$=4.0), 3.13–3.23 (m, 2H), 3.23–3.34 (m, 2H), 3.95–4.06 (m, 1H), 4.70–4.79 (m, 1H), 6.48 (dd, 1H, $J_1$=4.1, $J_2$=8.5), 6.84–6.92 (m, 1H), 6.93–6.97 (m, 1H); HPLC-MS calcd. for $C_{18}H_{27}FN_2O_4S$ (M+H$^+$) 387.2. found 387.4.

Step B. {1-(S)-[1-(S)-(5-Fluoro-2,3-dihydro-indol-1-ylmethyl)-3-methanesulfonyl-propylcarbamoyl]-3,3-dimethyl-butyl}-carbamic acid tert-butyl ester. The intermediate from Step A (500 mg, 1.29 mmol) was treated with 2 mL of a solution containing 45% trifluoroacetic acid, 45% dichloromethane and 10% water. The material was allowed to stand overnight and the solvent was removed. The resulting oil was treated with Boc-(L)-tBu-Ala (350 mg, 1.42 mmol), HATU (540 mg, 1.42 mmol) and dichloromethane (5 mL). The resulting suspension was treated with diisopropylethylamine (836 mg, 6.47 mmol) and allowed to stir overnight. The reaction contents were then poured into a separatory funnel and treated with saturated aqueous sodium bicarbonate solution. The aqueous layer was extracted with dichloromethane a total of 2 times and discarded. The comined organics were dried over MgSO$_4$ and the solvent was removed. The residue was purified by automated silica gel chromatography using a linear gradient of 0 to 100% ethyl acetate in hexane to afford the title compound as a solid (506 mg, 76%): $^1$H NMR (CDCl$_3$, 400 MHz) δ 0.74 (s, 9H), 1.41 (dd, 1H, $J_1$=8.3, $J_2$=14.5), 1.70 (dd, 1H, $J_1$=4.4, $J_2$=14.5), 2.57–2.72 (m, 2H), 2.85 (dd, 1H, $J_1$=6.8, $J_2$=13.6), 3.02 (dd, 1H, $J_1$=7.7, $J_2$=13.6), 3.07 (dd, 1H, $J_1$=8.7, $J_2$=17.4), 3.17–3.26 (m, 1H), 3.48 (dd, 1H, $J_1$=4.5, $J_2$=11.4), 3.55 (dd, 1H, $J_1$=3.4, $J_2$=11.4), 3.60 (s, 3H), 3.88–3.98 (m, 1H), 4.43 (ddd, 1H, $J_1$=4.3, $J_2$=8.1, $J_3$=12.3), 6.16 (dd, 1H, $J_1$=4.1, $J_2$=8.5), 6.41 (d, 1H, $J_1$=7.7), 6.48 (ddd, 1H, $J_1$=2.6, $J_2$=$J_3$=9.0), 6.52–6.56 (m, 1H), 6.75–6.79 (m, 1H), 6.78–6.84 (m, 1H), 6.98–7.10 (m, 3H); HPLC-MS calcd. for $C_{25}H_{40}FN_3O_5S$ (M+H$^+$) 514.3. found 514.5.

Step C. 2-(S)-(Benzooxazol-2-ylamino)-4,4-dimethyl-pentanoic acid [1-(S)-(5-fluoro-2,3-dihydro-indol-1-ylmethyl)-3-methanesulfonyl-propyl]-amide. The intermediate from step B (80 mg, 156 μmol) was treated with 2 mL of a solution containing 45% trifluoroacetic acid, 45% dichloromethane and 10% water. The material was allowed to stand overnight and the solvent was removed. The resulting material was partitioned between dichloromethane and 1 M NaOH. The organic phase was collected and the aqueous phase was extracted one more time with dichloromethane and discarded. The combined organics were dried over MgSO$_4$ and the solvent was removed. The resulting oil was treated with 2-chlorobenzoxazole (58 mg, 379 μmol), diisopropylethylamine (74 mg, 570 μmol) and n-butanol (2 mL). The reaction was then sealed and heated to 180° C. for 5 minutes using a microwave reactor. The reaction was almost over by HPLC-MS analysis but another 5 minute heating session was necessary. The reaction contents were then poured into a separatory funnel and treated with 5% aqueous sodium bisulfate solution. The aqueous layer was extracted with dichloromethane a total of 3 times and discarded. The comined organics were dried over MgSO$_4$ and the solvent was removed. The residue was purified by automated silica gel chromatography using a linear gradient of 0 to 100% ethyl acetate in hexane to afford the title compound as a solid (37.7 mg, 46%): $^1$H NMR (CDCl$_3$, 400 MHz) δ 0.88 (s, 9H), 1.61 (dd, 1H, J$_1$=9.0, J$_2$=14.6), 1.84 (dd, 1H, J$_1$=3.4, J$_2$=14.6), 1.89–2.02 (m, 1H), 2.11–2.22 (m, 2H), 2.46 (s, 3H), 2.73–2.87 (m, 2H), 2.86–3.05 (m, 3H), 3.11 (dd, 1H, J$_1$=6.2, J$_2$=13.9), 3.21–3.38 (m, 2H), 4.11–4.22 (m, 1H), 4.18–4.28 (m, 1H), 6.27 (dd, 1H, J$_1$=4.1, J$_2$=8.5), 6.42–6.53 (m, 1H), 6.57 (ddd, 1H, J$_1$=2.5, J$_2$=9.0, J$_3$=11.3), 6.69 (dd, 1H, J$_1$=2.4, J$_2$=8.2), 6.90 (d, 1H, J$_1$=8.6), 6.94–6.99 (m, 1H), 7.07–7.13 (m, 1H), 7.14 (d, 1H, J$_1$=8.0), 7.29 (d, 1H, J$_1$=7.7); HPLC-MS calcd. for C$_{27}$H$_{35}$FN$_4$O$_4$S (M+H$^+$) 531.3. found 531.5.

Example 6

2-(S)-(Benzooxazol-2-ylamino)-4,4-dimethyl-pentanoic acid (R)-[1-benzyloxymethyl-2-(5-fluoro-2,3-dihydro-indol-1-yl)-ethyl]-amide (R)-[1-Benzyloxymethyl-2-(5-fluoro-2,3-dihydro-indol-1-yl)-ethyl]-carbamic acid tert-butyl ester was prepared in an analogous manner to example 12, steps A and C using N-Boc-OBn-serinol and 5-fluoroindoline in 70% yield. HPLC-MS calcd. for C$_{23}$H$_{29}$FN$_2$O$_3$S (M+H$^+$) 401.2. found 401.5.

2-(S)-(Benzooxazol-2-ylamino)-4,4-dimethyl-pentanoic acid (R)-[1-benzyloxymethyl-2-(5-fluoro-2,3-dihydro-indol-1-yl)-ethyl]-amide was prepared in 40% overall yield in an analgous manner to example 3 except that the displacement of the chlorobenzoxazole was carried out overnight at 130° C. $^1$H NMR (CDCl$_3$, 400 MHz) δ 1.00 (s, 9H), 1.67 (dd, 1H, J$_1$=8.7, J$_2$=14.6), 1.96 (dd, 1H, J$_1$=3.7, J$_2$=14.6), 2.80–2.88 (m, 2H), 3.11–3.24 (m, 2H), 3.29–3.37 (m, 2H), 3.50 (dd, 1H, J$_1$=4.5, J$_2$=9.4), 3.65 (dd, 1H, J$_1$=3.2, J$_2$=9.4), 4.25–4.34 (m, 1H), 4.39–4.51 (m, 3H), 6.14–6.37 (m, 1H), 6.40 (dd, 1H, J$_1$=4.2, J$_2$=8.5), 6.66 (ddd, 1H, J$_1$=2.6, J$_2$=8.9, J$_3$=11.3), 6.73–6.77 (m, 1H), 6.89–6.94 (m, 1H), 7.03–7.10 (m, 1H), 7.16–7.24 (m, 2H), 7.24–7.39 (m, 6H); HPLC-MS calcd. for C$_{32}$H$_{37}$FN$_4$O$_3$ (M+H$^+$) 545.3. found 545.5.

Example 7

2-(S)-(Benzooxazol-2-ylamino)-4,4-dimethyl-pentanoic acid [2-(5-fluoro-2,3-dihydro-indol-1-yl)-1-(R)-hydroxymethyl-ethyl]-amide. The title compound of example 6 (34 mg, 70 μmol) was dissolved in MeOH (3 mL) and treated with 4 M HCl in dioxane (0.5 mL). The reaction was then treated with 10% Pd/C (7 mg) and the atmosphere was exchanged for hydrogen by sparging the solution with a needle and a balloon. After 2 h under a hydrogen balloon, the atmosphere was exchanged back to nitrogen and the catalyst was removed by filtration through celite. The solvent was removed and the residue was purified by preperative reverse phase HPLC to afford the title compound as a gum (18.6 mg, 47%); $^1$H NMR (CDCl$_3$, 400 MHz) δ 0.97 (s, 9H), 1.69 (dd, 1H, J$_1$=9.0, J$_2$=14.5), 1.81 (dd, 1H, J$_1$=3.4, J$_2$=14.5), 2.71–2.90 (m, 2H), 3.04–3.16 (m, 1H), 3.19–3.31 (m, 2H), 3.40–3.50 (m, 1H), 3.66 (d, 1H, J$_1$=5.2), 4.13–4.21 (m, 1H), 4.38 (dd, 1H, J$_1$=3.4, J$_2$=9.0), 6.44–6.52 (m, 1H), 6.59–6.66 (m, 1H), 6.70–6.74 (m, 1H), 7.14 (dd, 1H, J$_1$=J$_2$=7.7), 7.23 (dd, 1H, J$_1$=J$_2$=7.6), 7.30 (d, 1H, J=7.8), 7.33 (d, 1H, J=8.0); HPLC-MS calcd. for C$_{25}$H$_{31}$FN$_4$O$_3$ (M+H$^+$) 455.2. found 455.5.

Example 8

2-(S)-(Benzooxazol-2-ylamino)-3-cyclohexyl-N-[2-(5-fluoro-2,3-dihydro-indol-1-yl)-1-(S)-methyl-ethyl]-propionamide. Following the procedure of Example 12, the title compound, as a mono-trifluoroacetate salt, was obtained as a white solid (18 mg, 31 μmol, 12%): $^1$H NMR (CDCl$_3$, 400 MHz) δ 0.74–0.77 (m, 2H), 0.93–1.03 (m, 4H), 1.06 (d, 3H, J=6.8 Hz), 1.26–1.28 (m, 1H), 1.42–1.61 (m, 6H), 2.62–2.75 (m, 3H), 2.98–3.08 (m, 2H), 3.14–3.26 (m, 2H), 3.31–3.37 (1H, m), 4.03–4.08 (m, 1H), 4.15 (dd, 1H, J=8.8, 6.0 Hz), 6.24–6.28 (m, 1H), 6.46–6.48 (m, 1H), 6.56–6.58 (1H, m), 6.93–6.97 (m, 1H), 7.03–7.07 (m, 1H), 7.10–7.16 (m, 2H); HPLC-MS calcd. for C$_{27}$H$_{33}$FN$_4$O$_2$ (M+H$^+$) 465.3. found 465.5.

Example 9

3-(S)-[2-(S)-(Benzooxazol-2-ylamino)-3-cyclohexyl-propionylamino]-4-(5-fluoro-2,3-dihydro-indol-1-yl)-butyric acid tert-butyl ester. Following the procedure of Example 3, the title compound was obtained as a off-white solid (38 mg, 27%): $^1$H NMR (CDCl$_3$, 400 MHz) δ 0.90–0.98 (m, 2H), 1.11–1.48 (m, 5H), 1.32 (s, 9H), 1.79–1.59 (m, 6H), 2.47–2.59 (m, 2H), 2.78–2.83 (m, 2H), 2.96 (dd, 1H, J=14.0, 6.0 Hz), 3.14–3.26 (m, 2H), 3.41–3.47 (1H, m), 4.32 (dd, 1H, J=8.4, 6.4 Hz), 4.52 (dd, 1H, J=15.2, 6.4 Hz), 6.38–6.41 (m, 1H), 6.59–6.64 (m, 1H), 6.71–6.73 (1H, m), 6.53–6.60 (m, 1H), 7.03 (t, 1H, J=7.6 Hz), 7.13–7.17 (m, 1H), 7.03–7.15 (m, 3H), 7.24–7.26 (m, 1H), 8.06 (d, 1H, J=8.8 Hz); HPLC-MS calcd. for C$_{32}$H$_{41}$FN$_4$O$_4$ (M+H$^+$) 565.3. found 565.5.

Example 10

2-(S)-(Benzooxazol-2-ylamino)-N-[1-(R)-(benzyloxymethyl-2-(5-fluoro-2,3-dihydro-indol-1-yl)-ethyl]-3-cyclohexyl-propionamide. Following the procedure of Example 12, the title compound, mono-trifluoroacetate salt, was obtained as a off-white solid, (42 mg, 74 μmol, 17%): $^1$H NMR (CDCl$_3$, 400 MHz) δ 0.90–0.99 (m, 2H), 1.12–1.33 (m, 4H), 1.45 (m, 1H), 1.62–1.79 (m, 6H), 2.84 (m, 2H), 3.11 (m, 1H), 3.35 (m, 1H), 3.44 (m, 1H), 3.61 (m, 2H), 4.35–4.45 (2H, m), 4.51 (dd, 1H, J=21.2, 12.0 Hz), 6.44 (m, 1H), 6.63 (m, 1H), 6.75 (m, 1H), 7.13–7.17 (m, 1H), 7.23–7.38 (m, 8H); HPLC-MS calcd. for C$_{34}$H$_{39}$FN$_4$O$_3$ (M+H$^+$) 571.3. found 571.5.

Example 11

2-(S)-(Benzooxazol-2-ylamino)-N-[1-(R)-benzyloxymethyl-2-(4-fluoro-phenylamino)-ethyl]-3-cyclohexyl-propionamide. The title compound was synthesized by the following route:

Step A. (S)-N-tert-butoxycarbonyl-O-benzyloxy serine (available from Chem-Impex Incorporated, 430 mg, 1.53 mmol) was treated with 5 mL of a solution containing 45% trifluoroacetic acid, 45% dichloromethane and 10% water. The material was allowed to stand overnight and the solvent was removed. The resulting oil was evaporated and treated with 2-(S)-(benzooxazol-2-ylamino)-3-cyclohexyl-propionic acid (460 mg, 1.595 mmol) and HATU (530 mg, 1.61 mmol). The reagents were dissolved in dry dichloromethane (10 mL) and treated with diisopropylethylamine (800 μL, 4.59 mmol). The reaction was allowed to stir overnight. The reaction contents were then directly purified by automated flash chromatography. Compound 11a was obtained as a clear oil (530 mg, 1.173 mmol, 77%): $^1$H NMR (CDCl$_3$, 400 MHz) δ 0.80–0.98 (m, 2H), 1.08–1.23 (m, 4H), 1.35–1.45 (m, 1H), 1.53–1.76 (m, 6H), 3.46–3.55 (m, 4H), 3.98–4.02 (m, 1H), 4.19–4.33 (m, 1H), 4.38 (d, 1H, J=4.0 Hz), 4.42 (d, 1H, J=2.4 Hz), 6.66–6.75 (m, 2H), 7.09–7.25 (6H, m), 7.59–7.63 (1H, m); HPLC-MS calcd. for C$_{26}$H$_{33}$N$_3$O$_4$ (M+H$^+$) 452.3. found 452.5.

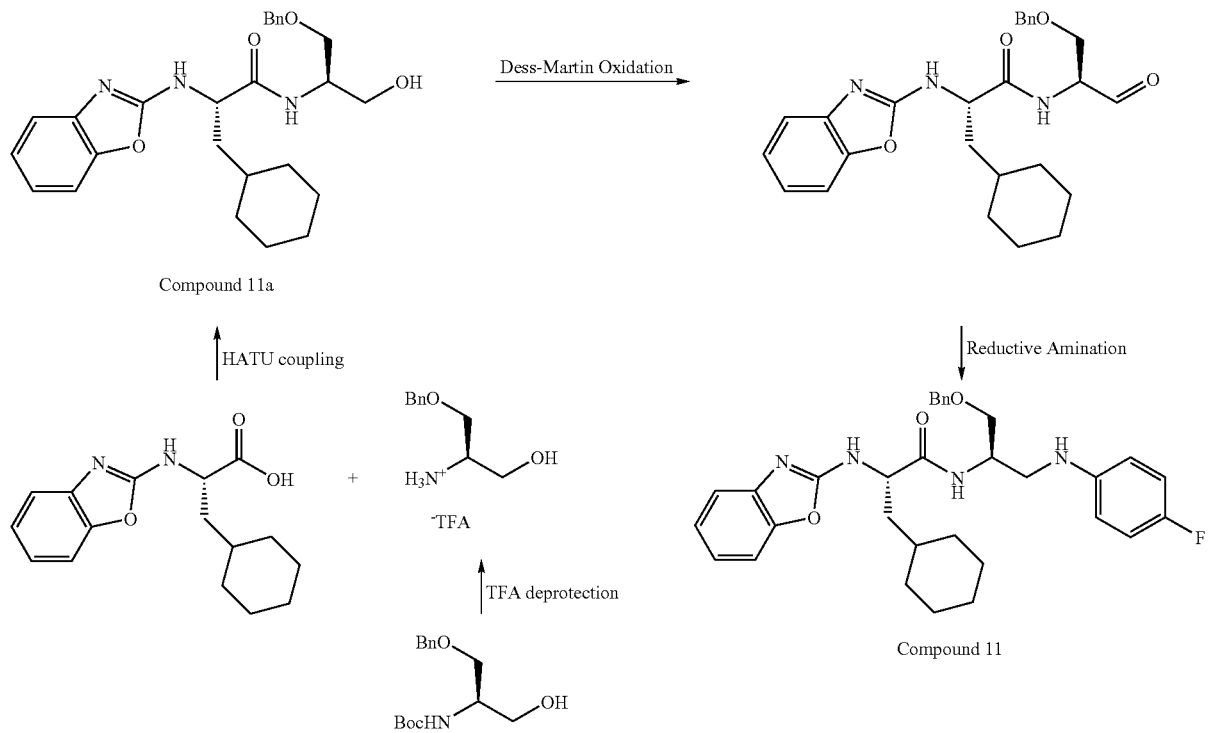

Step B. Compound 11a was dissolved in DCM (5 mL) and treated with the Dess-Martin periodinane (120 mg, 0.28 mmol). The reaction was allowed to stir for 2 hours and the reaction was monitored to completion by TLC ($R_f$=0.42, 1:1 hexanes:ethyl acetate). The reaction mixture was then diluted with DCM and extracted with 1 M $Na_2S_2O_3$ solution (1×) and saturated aqueous $NaHCO_3$ solution (1×). The organics were dried and the solvent was removed. The resulting oil was used directly for reductive amination as described below: A 65 mg (0.15 mmol) portion of the material prepared as above along with $NaCNBH_3$ (27 mg, 0.43 mmol) and 4-fluoroaniline (48 mg, 0.43 mmol) were dissolved in MeOH (3 mL) and treated with acetic acid (24 μL, 0.43 mmol). The resulting solution was allowed to stand overnight at room temperature and MeOH was evaporated. The resulting solid diluted with ethyl acetate. The organic portion was extracted with 1M NaOH solution (1×), saturated aq. NaCl (1×), dried over $MgSO_4$ and evaporated. The resulting oil was purified by prep-LC/MS to afford the title compound (38 mg, 40%) as a off-white mono-trifluoroacetate salt: $^1$H NMR ($CDCl_3$, 400 MHz) δ 0.90–1.06 (m, 2H), 1.14–1.29 (m, 4H), 1.44–1.51 (m, 1H), 1.64–1.86 (m, 6H), 3.29–3.32 (m, 1H), 3.32–3.42 (m, 1H), 3.54–3.64 (m, 2H), 4.27–4.31 (m, 1H), 4.36–4.40 (m, 1H), 4.46–4.53 (m, 2H), 6.84–6.88 (m, 2H), 6.92–6.96 (m, 2H), 7.10–7.14 (m, 1H), 7.19–7.23 (m, 1H), 7.24–7.35 (m, 7H); HPLC-MS calcd. for $C_{32}H_{37}FN_4O_3$ (M+H$^+$) 545.3. found 545.5.

Example 12

(S)-2-(Benzooxazol-2-ylamino)-4,4-dimethyl-pentanoic acid (R)-[2-(5-fluoro-2,3-dihydro-indol-1-yl)-1-methanesulfonylmethyl-ethyl]-amide.

Step A. (R)-(2-Hydroxy-1-methylsulfanylmethyl-ethyl)-carbamic acid tert-butyl ester. This material was prepared in 55% yield from the commercially available (R)-2-tert-butoxycarbonylamino-3-methylsulfanyl-propionic acid via the sodium borohydride reduction of the corresponding mixed anyhydride with i-butyl chloroformate.

Step B. (R)-(2-Hydroxy-1-methanesulfonylmethyl-ethyl)-carbamic acid tert-butyl ester. The intermediate from Step A (1.04 g; 4.42 mmol; 1.0 equiv) was treated with 10 mL of dichloromethane followed by mCPBA (3.0 g; 13.3 mmol; 3.0 equiv) after cooling in ice/water for 15 minutes. The oxidation completed after one hour. The reaction was quenched with $Me_2S$ to convert excess mCPBA to benzoic acid. The mixture was diluted with dichloromethane and excess benzoic acid was removed by Amberlyst A-21 ion-exchange resin since the desired oxidized product was water soluble. The solvent was removed to afford the title compound as an oil (1.11 g; 93%). HPLC-MS calcd. for Boc-deprotected material $C_4H_{11}NO_3S$ (M+H$^+$) 154.1. found 154.3.

Step C. (R)-[2-(5-Fluoro-2,3-dihydro-indol-1-yl)-1-methanesulfonylmethyl-ethyl]-carbamic acid tert-butyl ester. The intermediate from Step B (1.11 g; 4.38 mmol; 1.0 equiv) was treated with 5 mL of dichloromethane followed by Dess-Martin periodinane (2.8 g; 6.6 mmol; 1.5 equiv). After 1 hour, the homogeneous solution was quenched with methanol and concentrated. In the same reaction flask, the oxidized material was treated with methanol followed by 5-fluoro-indoline (0.73 g; 5.32 mmol; 1.2 equiv), acetic acid (1.57 g; 26.1 mmol; 6.0 equiv) and sodium cyanoborohydride (0.84 g; 13.4 mmol; 3.0 equiv). The reaction completed after 4 hours at room temperature. Methanol was removed by rotary evaporation. Diluted the reductive ammi-nated material with ethyl acetate and extracted with 1 M sodium hydroxide. The organics were collected and precipitates was observed. The material was crystallized in metha- Step D. (S)-2-(Benzooxazole-2-ylamino)-4,4-dimethyl-pentanoic acid (R)-[2-(5-fluoro-2,3-dihydro-indol-1-yl)-1-methanesulfonylmethyl-ethyl]-amide. The intermediate from Step C (157 mg, 0.421 mmol) was treated with 2 mL of a solution containing 45% trifluoroacetic acid, 45% dichloromethane and 10% water. The material was allowed to stand for 1 hour and the solvent was removed. The resulting oil was treated with 2-(S)-(benzooxazol-2-ylamino)-4,4-dimethyl-pentanoic acid (287 mg; 1.09 mmol; 1.3 equiv), HATU (482 mg; 1.27 mmol; 1.5 equiv) and DMF (2 mL). The resulting suspension was treated with diisopropylethylamine (371 mg, 2.87 mmol; 3.41 equiv) and allowed to stir overnight. The reaction contents were then poured into a separatory funnel and diluted with ethyl acetate and extracted with water twice. The organics were extracted with 1 M sodium hydroxide. The organics were collected and dried over $MgSO_4$ and concentrated. The residue was purified by automated silica gel chromatography using a linear gradient of 0 to 100% ethyl acetate in hexane to afford the title compound as a solid (18 mg, 8%): HPLC-MS calcd. for $C_{26}H_{33}FN_4O_4S$ (M+H$^+$) 517.2. found 517.5.

Example 13

2-(S)-(5-Chloro-benzooxazol-2-ylamino)-3-cyclohexyl-N-[2-(4-fluoro-phenylamino)-ethyl]-propionamide. The title compound was prepared from 2,5-dichlorobenzooxazole, L-cyclohexylalanine and N1-(4-fluoro-phenyl)-ethane-1,2-diamine-2HCl using the procedure analogous to that described in example 2. $^1$H NMR (DMSO-$d_6$, 400 MHz) a 8.35 (d, 1H, J=8 Hz), 8.18 (t, 1H, J=5.8 Hz), 7.30 (d, 1H, J=8.4 Hz), 7.18 (d, 1H, J=2.0 Hz), 6.90 (dd, 1H, J=8.4 Hz, J=2.0 Hz), 6.84 (m, 2H), 6.51 (m, 2H), 4.19(m, 1H), 3.15(m, 2H), 2.98(m, 2H), 1.55(m, 7H), 1.30(m, 1H), 1.05(m, 3H), 0.83(m, 2H). HPLC-MS calcd. for $C_{24}H_{28}ClFN_4O_2$(M+H$^+$) 459.19. found 459.4.

Example 14

2-(S)-(6-Chloro-benzooxazol-2-ylamino)-3-cyclohexyl-N-[2-(4-fluoro-phenylamino)-ethyl]-propionamide. The title compound was prepared from 2,6-dichlorobenzooxazole, L-cyclohexylalanine and N1-(4-Fluoro-phenyl)-ethane-1,2-diamine.2HCl using the procedure analogous to that described in example 2. $^1$H NMR (DMSO-$d_6$, 400 MHz) δ 8.30 (d, 1H, J=8.4 Hz), 8.17 (t, 1H, J=5.2 Hz), 7.46 (d, 1H, J=2.0 Hz), 7.13 (d, 1H, J=8.4 Hz), 7.08 (dd, 1H, J=8.4 Hz, J=2.0 Hz), 6.84(m, 2H), 6.51(m, 2H), 4.19(m, 1H), 3.15(m, 2H), 2.98(m, 2H), 1.55(m, 7H), 1.30(m, 1H), 1.05(m, 3H), 0.83(m, 2H). HPLC-MS calcd. for $C_{24}H_{28}ClFN_4O_2$(M+H$^+$) 459.19. found 459.4.

Example 15

2-(S)-(7-Chloro-benzooxazol-2-ylamino)-3-cyclohexyl-N-[2-(4-fluoro-phenylamino)-ethyl]-propionamide. The title compound was prepared from 2,7-dichlorobenzooxazole, L-cyclohexylalanine and N1-(4-Fluoro-phenyl)-ethane-1,2-diamine-2HCl using the procedure analogous to that described in example 2. $^1$H NMR (DMSO-$d_6$, 400 MHz) δ 8.45 (d, 1H, J=8.0 Hz), 8.17 (t, 1H, J=5.6 Hz), 7.13 (dd, 1H, J=1.2 Hz, J=7.6 Hz), 7.06 (dd, 1H, J=7.6 Hz), 7.00 (dd, 1H, J=7.6 Hz, J=1.2 Hz), 6.84(m, 2H), 6.51(m, 2H), 4.19(m, 1H), 3.15(m, 2H), 2.98(m, 2H), 1.55(m, 7H), 1.30(m, 1H), 1.05(m, 3H), 0.83(m, 2H). HPLC-MS calcd. for $C_{24}H_{28}ClFN_4O_2$(M+H$^+$) 459.19. found 459.5.

Example 16

2-(S)-(Benzothiazol-2-ylamino)-3-cyclohexyl-N-[2-(5-fluoro-2,3-dihydro-indol-1-yl)-ethyl]-propionamide. The title compound was prepared from 2-chlorobenzothiazole, L-cyclohexylalanine and 2-(5-fluoro-2,3-dihydro-indol-1-yl)-ethylamine using the procedure analogous to that described in example 2. HPLC-MS calcd. for $C_{26}H_{31}FN_4OS$ (M+H$^+$) 467.22. found 467.5.

Example 17

2-(S)-(Benzothiazol-2-ylamino)-3-cyclohexyl-N-[2-(4-methoxy-phenylamino)-ethyl]-propionamide. The title compound was prepared from 2-chlorobenzothiazole, L-cyclohexylalanine and N1-(4-methoxy-phenyl)-ethane-1,2-diamine.2HCl using the procedure analogous to that described in example 2. HPLC-MS calcd. for $C_{25}H_{32}N_4O_2S$ (M+H$^+$) 453.22. found 453.5.

Example 18

(S)-4,4-Dimethyl-2-(pyrazin-2-ylamino)-pentanoic acid [2-(5-fluoro-2,3-dihydro-indol-1-yl)-ethyl]-amide (S)-2-Amino-4,4-dimethyl-pentanoic acid [2-(5-fluoro-2,3-dihydro-indol-1-yl)-ethyl]-amide (20 mg, 0.066 mmol) was dissolved in DMF (0.7 mL) containing equimolar amounts of 2-chloropyrazine (6 μL, 0.066 mmol), 0.1 equivalents of CuI (1.3 mg, 0.006 mmol), and 1.5 equivalents of potassium carbonate (13.9 mg, 0.099 mmol). The mixture was stirred and heated by microwave to 240° C. for 30 minutes. After completion the mixture was purified by reverse phase LC to afford (S)-4,4-Dimethyl-2-(pyrazin-2-ylamino)-pentanoic acid [2-(5-fluoro-2,3-dihydro-indol-1-yl)-ethyl]-amide 2 (8.3 mg, 0.02 mmol, 32%): $^1$H-NMR (400 MHz, CD$_3$OD) δ=8.37 (m, 2H), 6.82–6.41 (m, 4H), 4.57 (dd, J=9.2, J=3.2, 1H), 3.42 (t, J=6.2, 2H), 3.36 (t, J=8.2, 2H), 3.14 (m, 2H), 2.88 (t, J=8.2, 2H), 1.83–1.62 (m, 2H), 0.96 (s, 9H). MS calcd. for $C_{21}H_{29}FN_5O$ (M+H$^+$) 386.23. found 386.5.

Example 19

2-(S)-(Isoquinolin-1-ylamino)-4,4-dimethyl-pentanoic acid [2-(5-fluoro-2,3-dihydro-indol-1-yl)-ethyl]-amide Following the procedure of Example 18, except substituting 1-chloroisoquinoline for chloropyrazine (11 mg, 0.066 mmol), the title compound was prepared (2.2 mg, 0.005 mmol, 7%): $^1$H-NMR (400 MHz, CD3OD) δ=8.52–6.31 (m, 9H), 4.56 (t, J=6.2, 1H), 3.49 (m, 2H), 3.32 (m, 2H), 3.15 (m, 2H), 2.82 (m, 2H), 2.08 (d, J=6.3, 2H), 0.99 (s, 9H). MS calcd. for $C_{26}H_{32}FN_4O$ (M+H$^+$) 435.25. found 435.5.

Example 20

(S)-3-Cyclohexyl-N-[2-(5-fluoro-2,3-dihydro-indol-1-yl)-ethyl]-2-(5-methyl-4-phenyl-thiazol-2-ylamino)-propionamide Step A. 2-(S)-Amino-3-cyclohexyl-N-[2-(5-fluoro-2,3-dihydro-indol-1-yl)-ethyl]-propionamide (500 mg, 1.50 mmol) was treated with 20 mL dichloromethane and diisopropylethylamine (313.0 μL, 1.80 mmol) followed by thiophosgene (205.2 μL, 1.8 mmol). After 1 h, the reaction mixture was charged with 50 mL of 0.5 M ammonia in dioxane.

Ammonia gas was bubbled into the reaction mixture for 20 min. After 2 h, the reaction contents were poured into a separatory funnel and diluted with dichloromethane. The organic layer was washed with 5% aq. sodium bisulfate, water (2×) and brine. The resulting solution was dried over magnesium sulfate and concentrated. The residue was purified by automated silica gel chromatography using linear gradient of 0–50% ethyl acetate in hexane to afford 3-Cyclohexyl-N-[2-(5-fluoro-2,3-dihydro-indol-1-yl)-ethyl]-2-(S)-thioureido-propionamide as a yellowish oil (60 mg; 17% yield). HPLC-MS calcd. for $C_{20}H_{29}FN_4OS$ (M+H$^+$) 393.54. found 393.5.

Step B. The intermediate from step A (30 mg, 0.076 mmol) was treated with 2 mL of ethoxyethanol, followed by 2-bromopropiophenone (19.5 mg, 0.918 mmol). The reaction mixture was allowed to be stirred at 65° C. for 16 h. The ethoxyethanol was removed by rotary evaporation. The mixture was diluted with ethyl acetate. The organic layer was washed with 5% aq. sodium bisulfate, water (2×) and brine. The solution was dried over magnesium sulfate and concentrated. The residue was purified by prep-HPLC to afford the title compound as a yellowish oil (13 mg; 52% yield). HPLC-MS calcd. for $C_{29}H_{35}FN_4OS$ (M+H$^+$) 507.68. found 507.5.

Example 21

2-(S)-(6-Chloro-benzothiazol-2-ylamino)-3-cyclohexyl-N-[2-(4-fluoro-phenylamino)-ethyl]-propionamide. The title compound was prepared from 2,6-dichlorobenzothiazole, L-cyclohexylalanine and N1-(4-fluoro-phenyl)-ethane-1,2-diamine.2HCl using the procedure analogous to that described in example 2. $^1$H NMR (DMSO-d$_6$, 400 MHz) δ 8.30 (d, 1H, J=8.0 Hz), 8.17 (t, 1H, J=5.6 Hz), 7.72 (d, 1H, J=2.4 Hz), 7.23 (d, 1H, J=8.4 Hz), 7.15 (dd, 1H, J=8.4 Hz, J=2.4 Hz), 6.84(m, 2H), 6.50(m, 2H), 4.40(m, 1H), 3.16(m, 2H), 2.97(m, 2H), 1.55(m, 7H), 1.30(m, 1H), 1.05(m, 3H), 0.83(m, 2H). HPLC-MS calcd. for $C_{24}H_{28}ClFN_4OS$ (M+H$^+$)475.17. found 475.3.

Example 22

3-Cyclohexyl-2-(S)-(6-fluoro-benzooxazol-2-ylamino)-N-[2-(4-fluoro-phenylamino)-ethyl]-propionamide. The title compound was prepared from 2-chloro-6-fluorobenzoxazole, L-cyclohexylalanine and N1-(4-fluoro-phenyl)-ethane-1,2-diamine.2HCl using the procedure analogous to that described in example 2. $^1$H NMR (DMSO-d$_6$, 400 MHz) δ 8.18(m, 2H), 7.30(dd, 1H, J=2.4 Hz, J=8.6 Hz), 7.11(dd, 1H, J=4.8 Hz, J=8.4 Hz), 6.89(m, 1H), 6.84(m, 2H), 6.51(m, 2H), 4.28 (m, 1H), 3.15(m, 2H), 2.95(m, 2H), 1.55(m, 7H), 1.30(m, 1H), 1.05(m, 3H), 0.83(m, 2H). HPLC-MS calcd. for $C_{24}H_{28}F_2N_4O_2$ (M+H$^+$)443.22. found 443.4.

Example 23

3-Cyclohexyl-2-(S)-(5-fluoro-benzooxazol-2-ylamino)-N-[2-(4-fluoro-phenylamino)-ethyl]-propionamide. The title compound was prepared from 2-chloro-5-fluorobenzoxazole, L-cyclohexylalanine and N1-(4-fluoro-phenyl)-ethane-1,2-diamine.2HCl using the procedure analogous to that described in example 2. $^1$H NMR (DMSO-d$_6$, 400 MHz) δ 8.29 (d, 1H, J=8.0 Hz), 8.16 (t, 1H, J=5.6 Hz), 7.27 (dd, 1H, J=4.4 Hz, J=8.4 Hz), 6.97 (dd, 1H, J=2.6 Hz, J=9.4 Hz), 6.80 (m, 2H), 6.72(m, 1H), 6.46(m, 2H), 5.42(m, 1H), 4.20 (m, 1H), 3.15(m, 2H), 2.95(m, 2H), 1.55(m, 7H), 1.30(m, 1H), 1.05(m, 3H), 0.83(m, 2H). HPLC-MS calcd. for $C_{24}H_{28}F_2N_4O_2$(M+H$^+$) 443.22. found 443.5.

Example 24

(S,S)2-{2-Cyclohexyl-1-[2-(4-fluoro-phenylamino)-1-methyl-ethylcarbamoyl]-ethylamino}-benzooxazole-6-carboxylic acid methyl ester; HPLC-MS for $C_{27}H_{33}FN_4O_4$ (M+H$^+$) 497.5.

Example 25

2-(S)-(7-Chloro-benzooxazol-2-ylamino)-3-cyclohexyl-N-[1-(S)-methyl-2-(5-methyl-isoxazol-3-ylamino)-ethyl]-propionamide; HPLC-MS for $C_{23}H_{30}ClN_5O_3$ (M+H$^+$) 460.5.

Example 26

3-(S)-([2-(S)-(6-Chloro-benzooxazol-2-ylamino)-3-cyclohexyl-propionylamino]-4-(5-fluoro-2,3-dihydro-indol-1-yl)-butyric acid
$^1$H NMR (CD$_3$OD, 400 MHz) δ 0.83–0.96 (m, 2H), 1.07–1.20 (m, 3H), 1.35–1.47 (m, 1H), 1.52–1.77 (m, 7H), 2.59 (d, 2H, J=6.6), 2.78–2.86 (m, 2H), 2.99 (dd, 1H, J=5.5, 13.6 Hz), 3.19–3.26 (m, 1H), 3.43–3.52 (m, 1H), 4.26 (dd, 1H, J=5.7, 9.2 Hz), 6.41 (dd, 1H, J=4.2, 8.6 Hz), 6.58 (ddd, 1H, J=2.5, 8.9, 11.5 Hz), 6.68–6.73 (m, 1H), 7.29–7.32 (m, 1H); HPLC-MS calcd. for $C_{28}H_{32}ClFN_4O_4$ (M+H$^+$) 543.2. found 543.3.

Example 27

3-(S)-[2-(S)-(6-Chloro-benzooxazol-2-ylamino)-3-cyclohexyl-propionylamino]-4-(5-fluoro-2,3-dihydro-indol-1-yl)-butyric acid ethyl ester; HPLC-MS calcd. for $C_{30}H_{36}ClFN_4O_4$ (M+H$^+$) 571.2. found 571.5.

Example 28

3-(S)-[2-(S)-(6-Chloro-benzooxazol-2-ylamino)-3-cyclohexyl-propionylamino]-4-(5-fluoro-2,3-dihydro-indol-1-yl)-butyric acid tert-butyl ester; $^1$H NMR (CD$_3$OD, 400 MHz) δ 0.83–0.97 (m, 2H), 1.07–1.18 (m, 3H), 1.30 (s, (m, 1H), 1.52–1.77 (m, 7H), 2.46 (dd, 2H, J=7.2, 15.5), 2.52 (dd, 2H, J=6.2, 15.6), 2.67–2.72 (m, 2H), 2.91 (dd, 1H, J=5.7, 13.7 Hz), 3.09–3.20 (m, 2H), 3.35–3.44 (m, 1H), 4.40 (dd, 1H, J=6.1, 8.7 Hz), 4.41–4.50 (m, 1H), 6.34 (dd, 1H, J=4.2, 8.6 Hz), 6.54–6.61 (m, 1H), 6.65–6.70 (m, 1H), 7.19 (dd, 1H, J=2.2, 8.6 Hz), 7.30 (d, 1H, J$_1$=8.6), 7.55 (d, 1H, J=2.1); HPLC-MS calcd. for $C_{32}H_{40}ClFN_4O_3S$ (M+H$^+$) 615.2. found 615.5.

Example 29

3-(S)-[2-(S)-(6-Chloro-benzothiazol-2-ylamino)-3-cyclohexyl-propionylamino]-4-(5-fluoro-2,3-dihydro-indol-1-yl)-butyric acid; HPLC-MS calcd. for $C_{28}H_{32}ClFN_4O_3S$ (M+H$^+$) 559.2. found 559.5.

Example 30

3-(S)-[2-(S)-(6-Chloro-benzothiazol-2-ylamino)-3-cyclohexyl-propionylamino]-4-(5-fluoro-2,3-dihydro-indol-1-yl)-butyric acid ethyl ester; $^1$H NMR (CD$_3$OD, 400 MHz) δ 0.83–0.97 (m, 2H), 1.06 (dd, 3H, J=7.1, 7.1), 3H), 1.35–1.47

(m, 1H), 1.52–1.77 (m, 7H), 2.51–2.63 (m, 2H), 2.69–2.78 (m, 1H), 2.94 (dd, 1H, J=5.9, 13.7), 3.12–3.21 (m, 2H), 3.86–3.99 (m, 2H), 4.38 (dd, 1H, J=6.1, 8.7), 4.44–4.52 (m, 1H), 6.34 (dd, 1H, J=4.2, 8.5 Hz), 6.54–6.61 (m, 1H), 6.65–6.70 (m, 1H), 7.19 (dd, 1H, J=2.2, 8.6 Hz), 7.31 (d, 1H, J=8.6), 7.56 (d, 1H, J=2.1); HPLC-MS calcd. for $C_{30}H_{36}ClFN_4O_3S$ (M+H$^+$) 587.2. found 587.5.

Example 31

(S,S)-2-(6-Chloro-benzooxazol-2-ylamino)-3-cyclohexyl-N-[1-(5-fluoro-2,3-dihydro-indol-1-ylmethyl)-3-methanesulfonyl-propyl]-propionamide; HPLC-MS calcd. for $C_{29}H_{36}ClFN_4O_4S$ (M+H$^+$) 591.2. found 591.4.

Example 32

2-(S)-(7-Chloro-benzooxazol-2-ylamino)-3-cyclohexyl-N-[2-(5-fluoro-2,3-dihydro-indol-1-yl)-1-(S)-methyl-ethyl]-propionamide; HPLC-MS for $C_{27}H_{32}ClFN_4O_2$ (M+H$^+$) 499.5.

Example 33

2-(S)-(6-Chloro-benzooxazol-2-ylamino)-3-cyclohexyl-N-[2-(5-fluoro-2,3-dihydro-indol-1-yl)-1-(S)-methyl-ethyl]-propionamide; HPLC-MS for $C_{27}H_{32}ClFN_4O_2$ (M+H$^+$) 499.5.

Example 34

2-(S)-(6-Chloro-benzothiazol-2-ylamino)-3-cyclohexyl-N-[2-(5-fluoro-2,3-dihydro-indol-1-yl)-1-(S)-methyl-ethyl]-propionamide; HPLC-MS for $C_{27}H_{32}ClFN_4OS$ (M+H$^+$) 514.6.

Example 35

2-(S)-(7-Chloro-benzooxazol-2-ylamino)-3-cyclohexyl-N-[2-(4-methoxy-phenylamino)-1-(S)-methyl-ethyl]-propionamide; HPLC-MS for $C_{26}H_{33}ClN_4O_3$ (M+H$^+$) 485.5.

Example 36

2-(S)-(7-Chloro-benzooxazol-2-ylamino)-3-cyclohexyl-N-[2-(4-methanesulfonyl-phenylamino)-1-(S)-methyl-ethyl]-propionamide; HPLC-MS for $C_{26}H_{33}ClN_4O_4S$ (M+H$^+$) 533.5.

Example 37

2-(S)-(7-Chloro-benzooxazol-2-ylamino)-3-cyclohexyl-N-[2-(3-methanesulfonyl-phenylamino)-1-(S)-methyl-ethyl]-propionamide; HPLC-MS for $C_{26}H_{33}ClN_4O_4S$ (M+H$^+$) 533.5.

Example 38

3-(S)-[2-(S)-(Benzooxazol-2-ylamino)-3-cyclohexyl-propionylamino]-4-(5-fluoro-2,3-dihydro-indol-1-yl)-butyric acid. The title compound was prepared in 70% yield in an analgous manner to example 4. HPLC-MS calcd. for Example 39

2-(S)-(7-Chloro-benzooxazol-2-ylamino)-3-cyclopentyl-N-[1-(S)-methyl-2-(4-trifluoromethoxy-phenylamino)-ethyl]-propionamide; HPLC-MS for $C_{25}H_{28}ClF_3N_4O_3$ (M+H$^+$) 524.5.

Example 40

2-{2-Cyclohexyl-1-(S)-[2-(4-fluoro-phenylamino)-ethyl-carbamoyl]-ethylamino}-benzooxazole-6-carboxylic acid methyl ester. The title compound was prepared from 2-Chloro-benzooxazole-6-carboxylic acid methyl ester, L-cyclohexylalanine and N1-(4-fluoro-phenyl)-ethane-1,2-diamine.2HCl using the procedure analogous to that described in example 2. HPLC-MS calcd. for $C_{26}H_{31}FN_4O_4$ (M+H$^+$)483.23. found 483.5.

Example 41

2-(S)-(7-Chloro-benzooxazol-2-ylamino)-4,4-dimethyl-pentanoic acid [1-(S)-methyl-2-(4-trifluoromethoxy-phenylamino)-ethyl]-amide; HPLC-MS for $C_{24}H_{28}ClF_3N_4O_3$ (M+H$^+$) 513.5.

Example 42

2-(S)-(Benzooxazol-2-ylamino)-3-cyclohexyl-N-[2-(4-fluoro-phenylamino)-ethyl]-propionamide. The title compound was prepared from 2-chlorobenzoxazole, L-cyclohexylalanine and N1-(4-fluoro-phenyl)-ethane-1,2-diamine.2HCl using the procedure analogous to that described in example 2. $^1$H NMR (DMSO-d$_6$, 400 MHz) δ 8.16(m, 2H), 7.30(m, 1H) 7.16(m, 1H), 7.04(m, 1H), 6.92 (m, 1H), 6.84(m, 2H), 6.50(m, 2H), 4.24 (m, 1H), 3.15(m, 2H), 2.97(m, 2H), 1.55(m, 7H), 1.30(m, 1H), 1.05(m, 3H), 0.83(m, 2H). HPLC-MS calcd. for $C_{24}H_{29}FN_4O_2$ (M+H$^+$) 424.23. found 425.5.

Example 43

2-(S)-(7-Chloro-benzooxazol-2-ylamino)-3-cyclopropyl-N-[1-(S)-methyl-2-(4-trifluoromethoxy-phenylamino)-ethyl]-propionamide; HPLC-MS for $C_{23}H_{24}ClF_3N_4O_3$ (M+H$^+$) 597.5.

Example 44

2-(S)-(7-Chloro-benzooxazol-2-ylamino)-3-cyclohexyl-N-[2-(5-fluoro-3,3-dimethyl-2,3-dihydro-indol-1-yl)-1-(S)-methyl-ethyl]-propionamide; $^1$H NMR (CDCl$_3$, 400 MHz) δ 1.04–1.25 (m, 2H), 1.28–1.45 (m, 3H), 1.45 (s, 3H, J=6.6), 1.49 (s, 3H), 1.59–1.71 (m, 1H), 1.80–1.94 (m, 6H), 1.97–2.06 (m, 1H), 3.18 (dd, 1H, J=5.7, 13.7 Hz), 3.30 (d, 1H, J=8.4 Hz), 3.37 (dd, 1H, J=7.1, 13.7 Hz), 3.44 (d, 1H, J=8.4 Hz), 6.56–6.67 (m, 2H), 6.89–6.96 (m, 2H), 7.126 (dd, 1H, J=1.0, 8.1 Hz), 7.76 (dd, 1H, J=7.9, 7.9 Hz), 7.45 (dd, 1H, J=1.0, 7.8); HPLC-MS calcd. for $C_{29}H_{36}ClFN_4O_2$ (M+H$^+$) 527.3. found 527.5.

Example 45

2-(S)-(7-Chloro-benzooxazol-2-ylamino)-3-cyclohexyl-N-[2-(5-fluoro-2,2-dimethyl-2,3-dihydro-indol-1-yl)-1-(S)-methyl-ethyl]-propionamide; $^1$H NMR (CDCl$_3$, 400 MHz) δ 0.75–0.92 (m, 2H), 0.98–1.13 (m, 3H), 1.04 (s, 3H, J=7.5), 1.12 (s, 3H), 1.28–1.40 (m, 1H), 1.48–1.76 (m, 7H), 2.57–2.59 (m, 2H), 2.66 (dd, 1H, J=8.3, 14.0 Hz), 2.95 (dd, 1H, J=5.7, 14.0 Hz), 3.98–4.11 (m, 1H), 4.28–4.36 (m, 1H), 5.80–5.92 (m, 1H), 6.23–6.30 (m, 1H), 6.37–6.43 (m, 1H), 6.58–6.66 (m, 2H), 6.95 (dd, 1H, J=1.1, 8.1 Hz), 7.01 (dd, 1H, J=7.9, 7.9 Hz), 7.15 (dd, 1H, J=1.1, 7.7); HPLC-MS calcd. for $C_{29}H_{36}ClFN_4O_2$ (M+H$^+$) 527.3. found 527.5.

B. Assays for Cathepsin Inhibitory Activity

Cathepsin S

The optimal substrate for cathepsin S, acetyl-histidine-proline-valine-lysine-amino carbamoyl coumarin, was identified from screening a combinatorial library of fluorogenic peptide substrates (Harris, J. L., B. J. Backes, et al. *Proc Natl Acad Sci USA* 2000, 97(14), 7754–9). Kinetic measurements are performed in a total reaction volume of 30 μl in 384-well microtiter plates. Cathepsin S, at a final concentration of 0.3–3 nM (active site), is incubated with the compounds at twelve varying concentrations in a buffer containing 100 mM NaAc (pH5.5), 1 mM EDTA, 100 mM NaCl, 0.01% Brij-35 for 20 minutes at room temperature. Control reactions in the absence of inhibitor are performed in replicates of 24. The reactions are initiated by adding the substrate, acetyl-histidine-proline-valine-lysine-amino carbamoyl coumarin, to a final concentration of 50 μM. The rate of substrate hydrolysis is measured by monitoring the increase in fluorescence at an excitation wavelength of 380 nm and an emission wavelength of 450 nm that results from cleavage of the aniline bond in the substrate by the enzyme. The apparent inhibition constants for the compounds are determined from the enzyme progress curves (Kuzmic, P., K. C. Elrod, et al. *Anal Biochem* 2000, 286(1), 45–50) and are then used to calculate the inhibition constants for competitive inhibitors.

Cathepsin K

The optimal substrate for cathepsin K, acetyl-lysine-histidine-proline-lysine-amino carbamoyl coumarin, was identified from screening a combinatorial library of fluorogenic peptide substrates (Harris, J. L., B. J. Backes, et al. *Proc Natl Acad Sci USA* 2000, 97(14), 7754–9). Kinetic measurements are performed in a total reaction volume of 30 μl in 384-well microtiter plates. Cathepsin K, at a final concentration of 3.5 nM (active site), is incubated with the compounds at twelve varying concentrations in a buffer containing 100 mM NaAc (pH5.5), 1 mM EDTA, 100 mM NaCl, 0.01% Brij-35 for 20 minutes at room temperature. Control reactions in the absence of inhibitor are performed in replicates of 24. The reactions are initiated by adding the substrate, acetyl-lysine-histidine-proline-lysine-amino carbamoyl coumarin, to a final concentration of 40 μM. The rate of substrate hydrolysis is measured by monitoring the increase in fluorescence at an excitation wavelength of 380 nm and an emission wavelength of 450 nm that results from cleavage of the aniline bond in the substrate by the enzyme. The apparent inhibition constants for the compounds are determined from the enzyme progress curves (Kuzmic, P., K. C. Elrod, et al. *Anal Biochem* 2000, 286(1), 45–50) and are then used to calculate the inhibition constants for competitive inhibitors.

Cathepsin L

The optimal substrate for cathepsin L, acetyl-histidine-lysine-phenylalanine-lysine-amino carbamoyl coumarin, was identified from screening a combinatorial library of fluorogenic peptide substrates (Harris, J. L., B. J. Backes, et al. *Proc Natl Acad Sci USA* 2000, 97(14), 7754–9). Kinetic measurements are performed in a total reaction volume of 30 μl in 384-well microtiter plates. Cathepsin L, at a final concentration of 0.1 nM (active site), is incubated with the compounds at twelve varying concentrations in a buffer containing 100 mM NaAc (pH5.5), 1 mM EDTA, 100 mM NaCl, 0.01% Brij-35 for 20 minutes at room temperature. Control reactions in the absence of inhibitor are performed in replicates of 24. The reactions are initiated by adding the substrate, acetyl-histidine-lysine-phenylalanine-lysine-amino carbamoyl coumarin, to a final concentration of 20 μM. The rate of substrate hydrolysis is measured by monitoring the increase in fluorescence at an excitation wavelength of 380 nm and an emission wavelength of 450 nm that results from cleavage of the aniline bond in the substrate by the enzyme. The apparent inhibition constants for the compounds are determined from the enzyme progress curves (Kuzmic, P., K. C. Elrod, et al. *Anal Biochem* 2000, 286(1), 45–50) and are then used to calculate the inhibition constants for competitive inhibitors.

Cathepsin B

The optimal substrate for cathepsin B, acetyl-histidine-proline-valine-lysine-amino carbamoyl coumarin, was identified from screening a combinatorial library of fluorogenic peptide substrates (Harris, J. L., B. J. Backes, et al. *Proc Natl Acad Sci USA* 2000, 97(14), 7754–9). Kinetic measurements are performed in a total reaction volume of 30 μL in 384-well microtiter plates. Cathepsin B, at a final concentration of 1.5 nM (active site), is incubated with the compounds at twelve varying concentrations in a buffer containing 100 mM NaAc (pH5.5), 1 mM EDTA, 100 mM NaCl, 0.01% Brij-35 for 20 minutes at room temperature. Control reactions in the absence of inhibitor are performed in replicates of 24. The reactions are initiated by adding the substrate, acetyl-histidine-proline-valine-lysine-amino carbamoyl coumarin, to a final concentration of 10 μM. The rate of substrate hydrolysis is measured by monitoring the increase in fluorescence at an excitation wavelength of 380 nm and an emission wavelength of 450 nm that results from cleavage of the aniline bond in the substrate by the enzyme. The apparent inhibition constants for the compounds are determined from the enzyme progress curves (Kuzmic, P., K. C. Elrod, et al. *Anal Biochem* 2000, 286(1), 45–50) and are then used to calculate the inhibition constants for competitive inhibitors.

Preferred cathepsin S inhibition constants for compounds of the present invention are less than 10 μM. More preferred inhibition constants for compounds of the present invention are less than 1.0 μM. Most preferred inhibition constants for compounds of the present invention are less than 0.1 μM.

Selectivity for cathepsin S in the presence of cathepsin isozymes was determined by the ratio of the cathepsin isozyme inhibition constant of a compound of the present invention to the cathepsin S inhibition constant of the same compound. Preferred compounds of the present invention selective for cathepsin S have ratios of greater than 10. More preferred compounds of the present invention selective for cathepsin S have ratios of greater than 100. Most preferred compounds of the present invention selective for cathepsin S have ratios of greater than 1000.

TABLE II

Assay Data for Inhibitors of Cathepsin S

| Example | $K_i$ Cat. S[a] |
|---|---|
| 1 | ++ |
| 2 | +++ |

TABLE II-continued

Assay Data for Inhibitors of Cathepsin S

| Example | $K_i$ Cat. S[a] |
|---|---|
| 3 | ++ |
| 4 | +++ |
| 5 | +++ |
| 6 | +++ |
| 7 | +++ |
| 8 | +++ |
| 9 | +++ |
| 10 | +++ |
| 11 | +++ |
| 12 | +++ |
| 13 | +++ |
| 14 | ++ |
| 15 | +++ |
| 16 | ++ |
| 17 | +++ |
| 18 | + |
| 19 | +++ |
| 20 | + |
| 21 | ++ |
| 22 | +++ |
| 23 | ++ |
| 24 | +++ |
| 25 | + |
| 26 | +++ |
| 27 | +++ |
| 28 | ++ |
| 29 | +++ |
| 30 | +++ |
| 31 | +++ |
| 32 | +++ |
| 33 | ++ |
| 34 | +++ |
| 35 | +++ |
| 36 | +++ |
| 37 | +++ |
| 38 | +++ |
| 39 | +++ |
| 40 | +++ |
| 41 | +++ |
| 42 | +++ |
| 43 | +++ |
| 44 | +++ |
| 45 | +++ |

[a]Cathepsin S inhibition constant for compounds of Formula I: +, <10 μM; ++, <1.0 μM; +++, <0.1 μM.
[b]Selectivity of compounds of Formula I for cathepsin S over another cathepsin: +, >10; ++, >100; +++, >1000.

TABLE III

Assay Data for Inhibitors of Cathepsin S over Cathepsin L, B, and K

| Example | Selectivity for Cat. S over Cat. L[b] | Selectivity for Cat. S over Cat. B[b] | Selectivity for Cat. S over Cat. K[b] |
|---|---|---|---|
| 1 | + | ++ | ++ |
| 2 | ++ | +++ | +++ |
| 3 | ++ | ++ | ++ |
| 4 | +++ | +++ | ++ |
| 5 | +++ | +++ | + |
| 6 | +++ | +++ | + |
| 7 | +++ | +++ | + |
| 8 | ++ | +++ | ++ |
| 9 | ++ | +++ | ++ |
| 10 | ++ | +++ | +++ |
| 11 | ++ | ++ | ++ |
| 12 | +++ | +++ | ++ |
| 13 | + | +++ | ++ |
| 14 | + | ++ | ++ |
| 15 | + | +++ | ++ |
| 16 | + | ++ | ++ |
| 17 | ++ | +++ | +++ |
| 18 | + | + | + |
| 19 | + | +++ | − |
| 20 | − | + | + |
| 21 | + | ++ | + |
| 22 | ++ | +++ | ++ |
| 23 | + | ++ | ++ |
| 26 | +++ | +++ | +++ |
| 27 | ++ | +++ | +++ |
| 28 | ++ | ++ | ++ |
| 30 | ++ | +++ | +++ |
| 45 | ++ | +++ | +++ |

[b]Selectivity of compounds of Formula I for cathepsin S over another cathepsin: +, >10; ++, >100; +++, >1000.

Although the foregoing invention has been described in some detail by way of illustration and example for purposes of clarity of understanding, it will be obvious that certain changes and modifications may be practiced within the scope of the appended claims. In addition, each reference provided herein is incorporated by reference in its entirety to the same extent as if each reference was individually incorporated by reference.

What is claimed is:
1. A compound of Formula I:

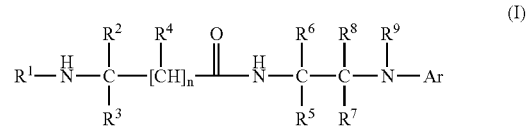

or a pharmaceutically acceptable salt or prodrug thereof, wherein:

$R^1$ is a member selected from the group consisting of a 5- to 6-membered monocyclic or 8- to 10-membered bicyclic heteroaryl containing 1 to 4 heteroatoms each independently a member selected from the group consisting of N, O and S, wherein said heteroaryl is substituted with 0–3 $R^{1a}$;

each $R^{1a}$ is independently a member selected from the group consisting of F, Cl, Br, CN, $NO_2$, $OR^{10}$, $SCH_3$, $S(=O)CH_3$, $S(=O)_2CH_3$, $NR^{11}R^{12}$, acetyl $C(=O)$ $OR^{18}$, $C(=O)NR^{18}R^{19}$, $S(=O)_2NR^{18}R^{19}$, $CF_3$, $OCF_3$, phenyl substituted with 0–3 $R^{14}$, a 5- to 6-membered heteroaryl containing 1 to 4 heteroatoms each independently a member selected from the group consisting of N, O and S, wherein said heteroaryl is substituted with 0–3 $R^{14}$, and a $C_1$–$C_4$ alkyl;

$R^2$ is a member selected from the group consisting of tert-butyl-$CH_2$—, tert-butyl-$CH_2$—$CH_2$—, a $C_1$–$C_4$ alkyl substituted with 1 $R^{2a}$, wherein said $C_1$–$C_4$ alkyl may optionally contain a heteroatom selected from the group consisting of —O—, —S—, —S(=O)— and —S(=O)$_2$—, a $C_3$–$C_7$ cycloalkyl substituted with 0–2 $R^{1b}$, and a $C_6$–$C_{11}$ bicycloalkyl substituted with 0–2 $R^{1b}$;

each $R^{1b}$ is independently a member selected from the group consisting of H, OH, F, Cl, acetyl, =O, $C_1$–$C_6$ alkyl, $C_1$–$C_6$ alkoxy, $CF_3$ and $OCF_3$;

each $R^{2a}$ is independently a member selected from the group consisting of a $C_6$–$C_{10}$ aryl substituted with 0–3 $R^{1a}$, a perfluorophenyl, a 5- to 6-membered monocyclic or 8- to 10-membered bicyclic heteroaryl containing 1 to 4 heteroatoms each independently a member selected from the group consisting of N, O and S, wherein said heteroaryl is substituted with 0–3 $R^{1a}$, a $C_3$–$C_8$ cycloalkyl substituted with 0–2 $R^{1b}$, and a $C_6$–$C_{11}$ bicycloalkyl substituted with 0–2 $R^{1b}$;

$R^3$ is a member selected from the group consisting of H and $C_1$–$C_6$ alkyl;

alternatively, $R^2$ and $R^3$ are taken together to form a 5–7 membered ring containing 0–2 heteroatoms each independently a member selected from the group consisting of N, O and S;

subscript n is 0 or 1;

$R^4$ is a member selected from the group consisting of H and $C_1$–$C_6$ alkyl;

alternatively, $R^2$ and $R^4$ are taken together to form a $C_5$–$C_7$ cycloalkyl;

$R^5$ is a member selected from the group consisting of H, $C(=O)OR^{24}$, $C(=O)NR^{25}R^{26}$, phenyl substituted with 0–2 $R^{21}$, 5- to 6-membered heteroaryl containing 1 to 4 heteroatoms each independently a member selected from the group consisting of N, O and S, wherein said heteroaryl is substituted with 0–2 $R^{21}$, $C_3$–$C_7$ cycloalkyl, $C_3$–$C_6$ alkenyl and $C_1$–$C_6$ alkyl substituted with 0–2 $R^{23}$, wherein a methylene of said $C_1$–$C_6$ alkyl may optionally be replaced by a heteroatom selected from the group consisting of —O—, —S—, —S(O)—, —S(=O)$_2$— and —NR$^{22}$—;

each of $R^6$, $R^7$ and $R^8$ is independently a member selected from the group consisting of H and $C_1$–$C_6$ alkyl;

alternatively, $R^5$ and $R^7$ are taken together to form a $C_5$–$C_7$ cycloalkyl;

$R^9$ is a member selected from the group consisting of H and $C_1$–$C_6$ alkyl;

each $R^{10}$ is independently a member selected from the group consisting of H, $C_3$–$C_7$ cycloalkyl, $C_1$–$C_4$ alkyl, a phenyl substituted with 0–3 $R^{14}$, and beuzyl substituted with 0–3 $R^{14}$;

each $R^{10}$ is independently a member selected from the group consisting of H, $^tBOC$, Cbz, $C_3$–$C_8$ cycloalkyl, ($C_1$–$C_6$ alkyl)-C(=O)—, ($C_1$–$C_6$ alkyl)-S(=O)$_2$—, $C_1$–$C_6$ alkyl, a phenyl substituted with 0–3 $R^{14}$ and a 5- to 6-membered heteroaryl containing 1 to 4 heteroatoms each independently a member selected from the group consisting of N, O and S, wherein said 5- to 6-membered heteroaryl is substituted with 0–3 $R^{14}$;

each $R^{12}$ is independently a member selected from the group consisting of H and $C_1$–$C_4$ alkyl;

each $R^{13}$ is independently a member selected from the group consisting of H, $C_3$–$C_8$ cycloalkyl, a phenyl substituted with 0–3 $R^{14}$, a 5- to 6-membered heteroaryl containing 1 to 4 heteroatoms each independently a member selected from the group consisting of N, O and S, wherein said 5- to 6-membered heteroaryl is substituted with 0–3 $R^{14}$, and a $C_1$–$C_6$ alkyl substituted with 0–1 $R^{17}$;

each $R^{14}$ is independently a member selected from the group consisting of H, OH, F, Cl, Br, CN, NO$_2$, COOR$^{18}$, C(=O)NR$^{18}$R$^{19}$, S(=O)$_2$NR$^{18}$R$^{19}$, acetyl, —SCH$_3$, —S(=O)CH$_3$, —S(=O)$_2$CH$_3$, NR$^{15}$R$^{16}$ $C_1$–$C_6$ alkoxy, $C_1$–$C_3$ perfluoroalkyl, $C_1$–$C_3$ perfluoroalkoxy and a $C_1$–$C_6$ alkyl;

each $R^{15}$ is independently a member selected from the group consisting of H, $C_1$–$C_4$ alkyl, ($C_1$–$C_4$ alkyl)-C(=O)— and ($C_1$–$C_4$ alkyl)-S(=O)$_2$—;

each $R^{16}$ is independently a member selected from the group consisting of H and $C_1$–$C_4$ alkyl;

each $R^{17}$ is independently a member selected from the group consisting of H, $C_3$–$C_7$ cycloalkyl, a phenyl substituted with 0–3 $R^{14}$ and a 5- to 6-membered heteroaryl containing 1 to 4 heteroatoms each independently a member selected from the group consisting of N, O and S, wherein said 5- to 6-membered heteroaryl is substituted with 0–3 $R^{14}$;

each of $R^{18}$ and $R^{19}$ is independently a member selected from the group consisting of H, and $C_1$–$C_4$ alkyl;

Ar is a member selected from the group consisting of phenyl substituted with 0–3 $R^{20}$, and 5- to 6-membered heteroaryl containing 1 to 4 heteroatoms each independently a member selected from the group consisting of N, O and S, wherein said heteroaryl is substituted with 0–3 $R^{20}$;

each $R^{20}$ is independently a member selected from the group consisting of H, F, Cl, Br, CN, OR$^{13}$, SCH$_3$, S(=O)CH$_3$, S(=O)$_2$CH$_3$, S(=O)$_2$NR$^{18}$R$^{19}$, NR$^{15}$R$^{16}$, acetyl, C(=O)NR$^{18}$R$^{19}$, CO$_2$R$^{18}$, C(=NH)NH$_2$, $C_1$–$C_6$ alkyl, CF$_3$, OCF$_3$ and a 5- to 6-membered heteroaryl containing 1 to 4 heteroatoms each independently a member selected from the group consisting of N, O and S, wherein said heteroaryl is substituted with 0–3 $R^{14}$;

alternatively, $R^9$ and an $R^{20}$ are taken together to form a 5- to 7-membered heterocyclic ring containing 1–2 heteroatoms each independently a member selected from the group consisting of N, O and S, substituted with 0–2 $R^{28}$, wherein said 5- to 7-membered heterocyclic ring is ortho-fused to Ar;

each $R^{21}$ is a member selected from the group consisting of H, F, Cl, Br, I, CN, NO$_2$, COOR$^{18}$, C(=O)NR$^{18}$R$^{19}$, S(=O)$_2$NR$^{18}$R$^{19}$, acetyl, —SCH$_3$, —S(=O)CH$_3$, —S(=O)$_2$CH$_3$, NR$^{15}$R$^{16}$, $C_1$–$C_4$ alkoxy, $C_1$–$C_4$ alkyl, $C_1$–$C_3$ perfluoroalkyl and $C_1$–$C_3$ perfluoroalkoxy;

$R^{22}$ is independently a member selected from the group consisting of H, $^tBOC$, Cbz, $C_3$–$C_8$ cycloalkyl, ($C_1$–$C_6$ alkyl)-C(=O)—, ($C_1$–$C_6$ alkyl)-S(=O)$_2$—, a $C_1$–$C_6$ alkyl substituted with 0–1 $R^{17}$, a phenyl substituted with 0–3 $R^{14}$ and a 5- to 6-membered heteroaryl containing 1 to 4 heteroatoms each independently a member selected from the group consisting of N, O and S, wherein said 5- to 6-membered heteroaryl is substituted with 0–3 $R^{14}$;

each $R^{23}$ is independently a member selected from the group consisting of H, OR$^{24}$, F, Cl, CN, NO$_2$, C(=O) OR$^{24}$, C(=O)NR$^{25}$R$^{26}$, NR$^{22}$R$^{27}$, $C_1$–$C_3$ perfluoroalkyl, $C_1$–$C_3$ perfluoroalkoxy, $C_2$–$C_4$ alkenyl, $C_2$–$C_4$ alkynyl, phenyl substituted with 0–3 $R^{21}$, 5- to 6-membered heteroaryl containing 1 to 4 heteroatoms each independently a member selected from the group consisting of N, O and S, wherein said heteroaryl is substituted with 0–3 $R^{21}$, $C_3$–$C_8$ heterocycle containing 1 to 2 heteroatoms each independently a member selected from the group consisting of N, O and S, wherein said heterocycle is substituted with 0–2 $R^{21}$ and is saturated or partially unsaturated, and $C_3$–$C_8$ cycloalkyl;

each $R^{24}$ is independently a member selected from the group consisting of H, $C_3$–$C_7$ cycloalkyl, $C_1$–$C_4$ alkyl substituted with 0–1 $R^{17}$, a phenyl substituted with 0–3 $R^{14}$, and a 5- to 6-membered heteroaryl containing 1 to 4 heteroatoms each independently a member selected from the group consisting of N, O and S, wherein said heteroaryl is substituted with 0–3 $R^{14}$;

each $R^{25}$ is independently a member selected from the group consisting of H, $C_3$–$C_8$ cycloalkyl, a phenyl substituted with 0–3 $R^{14}$, a 5- to 6-membered heteroaryl containing 1 to 4 heteroatoms each independently a member selected from the group consisting of N, O and S, wherein said 5- to 6-membered heteroaryl is substituted with 0–3 $R^{14}$, and a $C_1$–$C_6$ alkyl substituted with 0–1 $R^{17}$;

each $R^{26}$ is independently a member selected from the group consisting of H and $C_1$–$C_4$ alkyl;

alternatively, $R^{25}$ and $R^{26}$ on the same N atom are taken together to form a $C_5$–$C_7$ heterocycle containing 1–2 hetero atoms each independently a member selected from the group consisting of N, O and S;

each $R^{27}$ is independently a member selected from the group consisting of H and $C_1$–$C_4$ alkyl;

alternatively, $R^{22}$ and $R^{27}$ on the same N atom are taken together to form a $C_5$–$C_7$ heterocycle containing 1–2 heteroatoms each independently a member selected from the group consisting of N, O and S; and each $R^{28}$ is independently a member selected from the group consisting of $C_1$–$C_4$ alkyl, F, Cl and $C_1$–$C_4$ alkoxy, $CF_3$ and $OCF_3$;

alternatively, two $R^{28}$ may be combined to form $C_3$–$C_6$ cycloalkyl.

2. The compound of claim 1, wherein:

$R^1$ is a member selected from the group consisting of pyridyl substituted with 0–3 $R^{1a}$, pyrazolyl substituted with 0–2 $R^{1a}$, thiazolyl substituted with 0–2 $R^{1a}$, isothiazolyl substituted with 0–2 $R^{1a}$, benzothiazolyl substituted with 0–3 $R^{1a}$, indolyl substituted with 0–3 $R^{1a}$, quinolinyl substituted with 0–3 $R^{1a}$, isoquinolinyl substituted with 0–3 $R^{1a}$, quinoxalinyl substituted with 0–3 $R^{1a}$, quinazolinyl substituted with 0–3 $R^{1a}$, phthalazinyl substituted with 0–3 $R^{1a}$, cinnolinyl substituted with 0–3 $R^{1a}$, pteridinyl substituted with 0–3 $R^{1a}$, furazanyl substituted with 0–1 $R^{1a}$, pyrrolyl substituted with 0–3 $R^{1a}$, oxazolyl substituted with 0–2 $R^{1a}$, isoxazolyl substituted with 0–2 $R^{1a}$, benzooxazolyl, substituted with 0–3 $R^{1a}$, indazolyl substituted with 0–3 $R^{1a}$, pyrimidinyl substituted with 0–3 $R^{1a}$, pyrazinyl substituted with 0–3 $R^{1a}$, pyridazinyl=substituted with 0–3 $R^{1a}$, purinyl substituted with 0–3 $R^{1a}$, naphthpyridinyl substituted with 0–3 $R^{1a}$, imidazolyl substituted with 0–3 $R^{1a}$, oxazolo[4,5-b]pyridinyl substituted with 0–3 $R^{1a}$, oxazolo[4,5-c]pyridinyl substituted with 0–3 $R^{1a}$, oxazolo[5,4-b]pyridinyl substituted with 0–3 $R^{1a}$ and oxazolo[5,4-c]pyridinyl substituted with 0–3 $R^{1a}$.

3. The compound of claim 2, wherein:

$R^1$ is a member selected from the group consisting of benzooxazolyl substituted with 0–3 $R^{1a}$, benzothiazolyl substituted with 0–3 $R^{1a}$, thiazolyl substituted with 0–2 $R^{1a}$, isoquinolinyl substituted with 0–3 $R^{1a}$, quinolinyl substituted with 0–3 $R^{1a}$, and pyrazinyl substituted with 0–3 $R^{1a}$.

4. The compound of claim 1, wherein:

$R^2$ is a member selected from the group consisting of a $C_1$–$C_4$ alkyl substituted with 1 $R^{2a}$, wherein said $C_1$–$C_4$ alkyl may optionally contain a heteroatom selected from the group consisting of —O—, —S—, —S(=O)— and —S(=O)$_2$—, a $C_3$–$C_7$ cycloalkyl substituted with 0–2 $R^{1b}$, a $C_6$–$C_{11}$ bicycloalkyl substituted with 0–2 $R^{1b}$, tert-butyl-CH$_2$— and tert-butyl-CH$_2$—CH$_2$—; and each $R^{2a}$ is independently a member selected from the group consisting of a $C_6$–$C_{10}$ aryl substituted with 0–3 $R^{1a}$, a $C_3$–$C_8$ cycloalkyl substituted with 0–2 $R^{1b}$, and a $C_6$–$C_{11}$ bicycloalkyl substituted with 0–2 $R^{1b}$.

5. The compound of claim 4, wherein:

$R^2$ is a member selected from the group consisting of a $C_1$–$C_2$ alkyl substituted with 1 $R^{2a}$, tert-butyl-CH$_2$—, and tert-butyl-CH$_2$—CH$_2$—; and each $R^{2a}$ is a $C_3$–$C_8$ cycloatkyl substituted with 0–2 $R^{1b}$.

6. The compound of claim 1, wherein:

$R^5$ is a member selected from the group consisting of H, $C(=O)OR^{24}$, $C(=O)NR^{25}R^{26}$, phenyl substituted with 0–2 $R^{21}$, $C_3$–$C_7$ cycloalkyl, and $C_1$–$C_6$ alkyl substituted with 0–1 $R^{23}$, wherein said $C_1$–$C_6$ alkyl may optionally contain a heteroatom selected from the group consisting of —O—, —S—, —S(=O)—, —S(=O)$_2$— and —NR$^{22}$—; and each $R^{23}$ is independently a member selected from the group consisting of H, $C(=O)OR^{24}$, $C(=O)NR^{25}R^{26}$, $NR^{22}R^{27}$, $C_1$–$C_4$ alkoxy, phenyl substituted with 0–3 $R^{21}$, $C_3$–$C_8$ heterocycle containing 1 to 2 heteroatoms each independently a member selected from the group consisting of N, O and S, wherein said heterocycle is substituted with 0–2 $R^{21}$ and is saturated or partially unsaturated, and $C_3$–$C_8$ cycloalkyl.

7. The compound of claim 6, wherein said compound has Formula Ib:

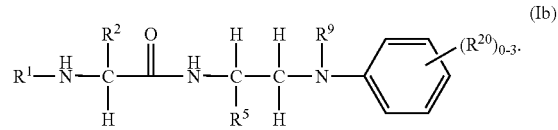

(Ib)

8. The compound of claim 7, wherein said compound has Formula Ic:

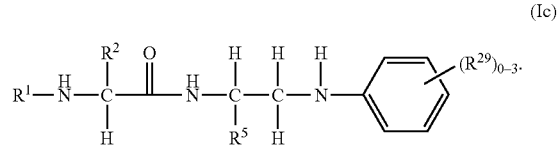

(Ic)

9. The compound of claim 7, wherein said compound has Formula Id:

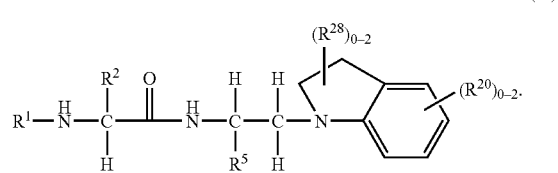

(Id)

10. The compound of claim 1, wherein $R^2$ is a member selected from the group consisting tert-butyl-CH$_2$— and tert-butyl-CH$_2$—CH$_2$— and at least one of $R^5$, $R^6$, $R^7$, $R^8$ and $R^9$ is not H.

11. The compound of claim 1, wherein
  R$^1$ is a member selected from the group consisting of benzooxazolyl substituted with 0–2 R$^{1a}$, benzothiazolyl substituted with 0–2 R$^{1a}$, thiazolyl substituted with 0–2 R$^{1a}$, isoquinolinyl substituted with 0–2 R$^{1a}$, quinolinyl substituted with 0–3 R$^{1a}$ and pyrazinyl substituted with 0–2 R$^{1a}$;
  each R$^{1a}$ is independently a member selected from the group consisting of F, Cl, Br, C$_1$–C$_4$ alkoxy, SCH$_3$, S(=O)CH$_3$, S(=O)$_2$CH$_3$, acetyl, C(=O)OCH$_3$, CF$_3$, OCF$_3$, phenyl substituted with 0–1 R$^{14}$, and a C$_1$–C$_4$ alkyl;
  R$^2$ is a C$_1$–C$_2$ alkyl substituted with 1 R$^{2a}$,
  each R$^{2a}$ is independently a member selected from the group consisting of a C$_3$–C$_8$ cycloalkyl;
  each of R$^3$, R$^6$, R$^7$, R$^8$ is H;
  n is 0;
  R$^5$ is a member selected from the group consisting of H, and C$_1$–C$_6$ alkyl substituted with 0–1 R$^{23}$, wherein said C$_1$–C$_6$ alkyl may optionally contain a heteroatom selected from the group consisting of —O—, —S—, and —S(=O)$_2$—;
  R$^9$ is a member selected from the group consisting of H and C$_1$–C$_6$ alkyl,
  Ar is a member selected from the group consisting of phenyl substituted with 0–3 R$^{20}$, and 5-membered heteroaryl containing 1 to 2 heteroatoms each independently a member selected from the group consisting of N, O and S, wherein said heteroaryl is substituted with 0–2 R$^{20}$;
  each R$^{20}$ is independently a member selected from the group consisting of H, F, Cl, Br, CN, C$_1$–C$_4$ alkoxy, OPh, OBn, SCH$_3$, S(=O)CH$_3$, S(=O)$_2$CH$_3$, S(=O)$_2$NR$^{18}$R$^{19}$, NR$^{15}$R$^{16}$, acetyl, C(=O)NR$^{18}$R$^{19}$, CO$_2$R$^{18}$, C(=NH)NH$_2$, C$_1$–C$_6$ alkyl, CF$_3$, OCF$_3$ and
  alternatively, R$^{20}$ and R$^9$ are taken together to form a 5-membered heterocyclic ring containing 1 nitrogen atom, wherein said heterocyclic ring is substituted with 0–2 R$^{28}$;
  each R$^{23}$ is independently a member selected from the group consisting of H, OH, F, Cl, CN, C(=O)OR$^{24}$, C(=O)NR$^{25}$R$^{26}$, NR$^{22}$R$^{27}$, phenyl substituted with 0–3 R$^{21}$, C$_3$–C$_8$ heterocycle containing 1 to 2 heteroatoms each independently a member selected from the group consisting of N, O and S, wherein said heterocycle is substituted with 0–2 R$^{21}$ and is saturated or partially unsaturated, and C$_3$–C$_8$ cycloalkyl;
  R$^{22}$ is independently a member selected from the group consisting of H, $^t$BOC, Cbz, (C$_1$–C$_6$ alkyl)-C(=O)—, (C$_1$–C$_6$ alkyl)-S(=O)$_2$—, a C$_1$–C$_6$ alkyl;
  each R$^{24}$ is independently a member selected from the group consisting of H, C$_1$–C$_4$ alkyl, a phenyl substituted with 0–3 R$^{14}$, and a benzyl substituted with 0–3 R$^{14}$; and
  each R$^{28}$ is independently a member selected from the group consisting of F and C$_1$–C$_2$ alkyl, alternatively, two R$^{28}$ on the same carbon may be combined to form C$_3$–C$_4$ cycloalkyl.

12. The compound of claim 1, wherein said compound is selected from the group consisting of: (S)-2-(Benzooxazol-2-ylamino)-3-cyclohexyl-N-[2-(5-fluoro-2,3-dihydro-indol-1-yl)-ethyl]-propionamide; (S)-2-(Benzooxazol-2-ylamino)-3-cyclohexyl-N-[2-(4-methoxy-phenylamino)-ethyl]-propionamide; 3-(S)-[2-(S)-(Benzooxazol-2-ylamino)-4,4-dimethyl-pentanoylamino]-4-(5-fluoro-2,3-dihydro-indol-1-yl)-butyric acid tert-butyl ester; 3-(S)-[2-(S)-(Benzooxazol-2-ylamino)-4,4-dimethyl-pentanoylamino]-4-(5-fluoro-2,3-dihydro-indol-1-yl)-butyric acid; 2-(S)-(Benzooxazol-2-ylamino)-4,4-dimethyl-pentanoic acid [1-(S)-(5-fluoro-2,3-dihydro-indol-1ylmethyl)-3-methanesulfonyl-propyl]-amide; 2-(S)-(Benzooxazol-2-ylamino)-4,4-dimethyl-pentanoic acid (R)-[1-benzyloxymethyl-2-(5-fluoro-2,3-dihydro-indol-1-yl)-ethyl]-amide; 2-(S)-(Benzooxazol-2-ylamino)-4,4-dimethyl-pentanoic acid [2-(5-fluoro-2,3-dihydro-indol-1-yl)-1-(R)-hydroxymethyl-ethyl]-amide; 2-(S)-(Benzooxazol-2-ylamino)-3-cyclohexyl-N-[2-(5-fluoro-2,3-dihydro-indol-1-yl)-1-(S)-methyl-ethyl]-propionamide; 3-(S)-[2-(S)-(Benzooxazol-2-ylamino)-3-cyclohexyl-propionylamino]-4-(5-fluoro-2,3-dihydro-indol-1-yl)-butyric acid tert-butyl ester; 2-(S)-(Benzooxazol-2-ylamino)-N-[1-(R)-(benzyloxymethyl-2-(5-fluoro-2,3-dihydro-indol-1-yl)-ethyl]-3-cyclohexyl-propionamide; 2-(S)-(Benzooxazol-2-ylamino)-N-[1-(R)-benzyloxymethyl-2-(4-fluoro-phenylamino)-ethyl]-3-cyclohexyl-propionamide; (S)-2-(Benzooxazol-2-ylamino)-4,4-dimethyl-pentanoic acid (R)-[2-(5-fluoro-2,3-dihydro-indol-1-yl)-1-methanesulfonylmethyl-ethyl]-amide; 2-(S)-(5-Chloro-benzooxazol-2-ylamino)-3-cyclohexyl-N-[2-(4-fluoro-phenylamino)-ethyl]-propionamide; 2-(S)-(6-Chloro-benzooxazol-2-ylamino)-3-cyclohexyl-N-[2-(4-fluoro-phenylamino)-ethyl]-propionamide; 2-(S)-(7-Chloro-benzooxazol-2-ylamino)-3-cyclohexyl-N-[2-(4-fluoro-phenylamino)-ethyl]-propionamide; 2-(S)-(Benzothiazol-2-ylamino)-3-cyclohexyl-N-[2-(5-fluoro-2,3-dihydro-indol-1-yl)-ethyl]-propionamide; 2-(S)-(Benzotbiazol-2-ylamino)-3-cyclohexyl-N-[2-(4-methoxy-phenylamino)-ethyl]-propionamide; (S)-4,4-Dimethyl-2-(pyrazin-2-ylamino)-pentanoic acid [2-(5-fluoro-2,3-dihydro-indol-1-yl)-ethyl]-amide; 2-(S)-(Isoquinolin-1-ylamino)-4,4-dimethyl-pentanoic acid [2-(5-fluoro-2,3-dihydro-indol-1-yl)-ethyl]-amide; (S)-3-Cyclohexyl-N-[2-(5-fluoro-2,3-dihydro-indol-1-yl)-ethyl]-2-(5-methyl-4-phenyl-thiazol-2-ylamino)-propionamide; 2-(S)-(6-Chloro-benzothiazol-2-ylamino)-3-cyclohexyl-N-[2-(4-fluoro-phenylamino)-ethyl]-propionamide; 3-Cyclohexyl-2-(S)-(6-fluoro-benzooxazol-2-ylamino)-N-[2-(4-fluoro-phenylamino)-ethyl]-propionamide; 3-Cyclohexyl-2-(S)-(5-fluoro-benzooxazol-2-ylamino)-N-[2-(4-fluoro-phenylamino)-ethyl]-propionamide; (S,S)2-{2-Cyclohexyl-1-[2-(4-fluoro-phenylamino)-1-methyl-ethylcarbamoyl]-ethylamino}-benzooxazole-6-carboxylic acid methyl ester; 2-(S)-(7-Chloro-benzooxazol-2-ylamino)-3-cyclohexyl-N-[1-(S)-methyl-2-(5-methyl-isoxazol-3-ylamino)-ethyl]-propionamide; 3-(S)-([2-(S)-(6-Chloro-benzooxazol-2-ylamino)-3-cyclohexyl-propionylamino]-4-(5-fluoro-2,3-dihydro-indol-1-yl)-butyric acid; 3-(S)-[2-(S)-(6-Chloro-benzooxazol-2-ylamino)-3-cyclohexyl-propionylamino]-4-(5-fluoro-2,3-dihydro-indol-1-yl)-butyric acid ethyl ester; 3-(S)-[2-(S)-(6-Chloro-benzooxazol-2-ylamino)-3-cyclohexyl-propionylamino]-4-(5-fluoro-2,3-dihydro-indol-1-yl)-butyric acid tert-butyl ester; 3-(S)-[2-(S)-(6-Chloro-benzothiazol-2-ylamino)-3-cyclohexyl-propionylamino]-4-(5-fluoro-2,3-dihydro-indol-1-yl)-butyric acid; 3-(S)-[2-(S)-(6-Chloro-benzotbiazol-2-ylamino)-3-cyclohexyl-propionylamino]-4-(5-fluoro-2,3-dihydro-indol-1-yl)-butyric acid ethyl ester; (S,S)-2-(6-Chloro-benzooxazol-2-ylamino)-3-cyclohexyl-N-[1-(5-fluoro-2,3-dihydro-indol-1-ylmethyl)-3-methanesulfonyl-propyl]-propionamide; 2-(S)-(7-Chloro-benzooxazol-2-ylamino)-3-cyclohexyl-N-[2-(5-fluoro-2,3-dihydro-indol-1-yl)-1-(S)-methyl-ethyl]-propionamide; 2-(S)-(6-Chloro-benzooxazol-2-ylamino)-3-cyclohexyl-N-[2-(5-fluoro-2,3-dihydro-indol-1-yl)-1-(S)-methyl-ethyl]-propionamide; 2-(S)-(6-Chloro-benzothiazol- 2-ylamino)-3-cyclohexyl-N-[2-(5-fluoro-2,3-dihydro-indol-1-yl)-1-(S)-methyl-ethyl]-propionamide; 2-(S)-(7-Chloro-benzooxazol-2-ylamino)-3-cyclohexyl-N-[2-(4-methoxy-phenylamino)-1-(S)-methyl-ethyl]-propionamide; 2-(S)-(7-Chloro-benzooxazol-2-ylamino)-3-cyclohexyl-N-[2-(4-methanesulfonyl-phenylamino)-1-(S)-methyl-ethyl]-propionamide; 2-(S)-(7-Chloro-benzooxazol-2-ylamino)-3-cyclohexyl-N-[2-(3-methanesulfonyl-phenylamino)-1-(S)-methyl-ethyl]-propionamide; 3-(S)-[2-(S)-(Benzooxazol-2-ylamino)-3-cyclohexyl-propionylamino]-4-(5-fluoro-2,3-dihydro-indol-1-yl)-butyric acid; 2-(S)-(7-Chloro-benzooxazol-2-ylamino)-3-cyclopentyl-N-[1-(S)-methyl-2-(4-trifluoromethoxy-phenylamino)-ethyl]-propionamide; 2-{2-Cyclohexyl-1-(S)-[2-(4-fluoro-phenylamino)-ethylcarbamoyl]-ethylamino}-benzooxazole-6-carboxylic acid methyl ester; 2-(S)-(7-Chloro-benzooxazol-2-ylamino)-4,4-dimethyl-pentanoic acid [1-(S)-methyl-2-(4-trifluoromethoxy-phenylamino)-ethyl]-amide; 2-(S)-(Benzooxazol-2-ylamino)-3-cyclohexyl-N-[2-(4-fluoro-phenylamino)-ethyl]-propionamide; 2-(S)-(7-Chloro-benzooxazol-2-ylamino)-3-cyclopropyl-N-[1-(S)-methyl-2-(4-trifluoromethoxy-phenylamino)-ethyl]-propionamide; 2-(S)-(7-Chloro-benzooxazol-2-ylamino)-3-cyclohexyl-N-[2-(5-fluoro-3,3-dimethyl-2,3-dihydro-indol-1-yl)-1-(S)-methyl-ethyl]-propionamide; and 2-(S)-(7-Chloro-benzooxazol-2-ylamino)-3-cyclohexyl-N-[2-(5-fluoro-2,2-dimethyl-2,3-dihydro-indol-1-yl)-1-(S)-methyl-ethyl]-propionamide.

13. A pharmaceutical composition, said composition comprising a compound of claim 1.

14. A pharmaceutical composition, said composition comprising a compound of claim 2.

15. A pharmaceutical composition, said composition comprising a compound of claim 3.

16. A pharmaceutical composition, said composition comprising a compound of claim 4.

17. A pharmaceutical composition, said composition comprising a compound of claim 5.

18. A pharmaceutical composition, said composition comprising a compound of claim 6.

19. A pharmaceutical composition, said composition comprising a compound of claim 7.

20. A pharmaceutical composition, said composition comprising a compound of claim 8.

21. A pharmaceutical composition, said composition comprising a compound of claim 9.

22. A pharmaceutical composition, said composition comprising a compound of claim 10.

23. A pharmaceutical composition, said composition comprising a compound of claim 11.

24. A pharmaceutical composition, said composition comprising a compound of claim 12.

* * * * *